(12) United States Patent
Sahin et al.

(10) Patent No.: US 11,712,437 B2
(45) Date of Patent: Aug. 1, 2023

(54) INHIBITORS OF LYSYL OXIDASES

(71) Applicant: University of South Carolina, Columbia, SC (US)

(72) Inventors: Ozgur Sahin, Lexington, SC (US); Campbell McInnes, Irmo, SC (US); Ozge Saatci, Columbia, SC (US); Chad Beneker, Irmo, SC (US); Abdol-Hossein Rezaeian, Lexington, SC (US); Metin Cetin, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 17/693,371

(22) Filed: Mar. 13, 2022

(65) Prior Publication Data

US 2022/0378753 A1  Dec. 1, 2022

Related U.S. Application Data

(60) Provisional application No. 63/187,979, filed on May 13, 2021.

(51) Int. Cl.
*A61K 31/427* (2006.01)
*A61K 45/06* (2006.01)

(52) U.S. Cl.
CPC ............ *A61K 31/427* (2013.01); *A61K 45/06* (2013.01)

(58) Field of Classification Search
None
See application file for complete search history.

(56) References Cited

FOREIGN PATENT DOCUMENTS

EP          3811940          4/2021
WO      WO2020232255      11/2020

OTHER PUBLICATIONS

Ngoei, Kevin, et al., Identification and characterization of bi-thiazole-2,2'-diamines as kinase inhibitory scaffolds, Biochimica et Bioohysica Acta, Proteins & Proteomics, vol. 1834, No. 6, Jun. 1, 2013, pp. 1570-9639, Netherlands.

Piala, Alexander T., et al., Discovery of novel TAOK2 inhibitor scaffolds from high-throughput screening, Bioorganic & Medicinal Chemistry Letters, vol. 26, No. 16, Jul. 6, 2016, pp. 3923-3927, Elsevier, Amsterdam, Netherlands.

Brvar, Matjaz, et al., Sturcture-Based Discovery of Substituted 4,5'Bithiazoles as Novel DNA Gyrase Inhibitors, Journal of Medicinal Chemistry, vol. 55, No. 14, Jul. 26, 2012, pp. 6413-6426.

Hutchinson, John H., et al., Small Molecule Lysyl Oxidase-like 2 (LOXL2) Inhibitors: The Identification of an Inhibitor Selective for LOXL2 over LOX, ACS Medicinal Chemistry Letters, vol. 8, No. 4, Mar. 6, 2017, pp. 423-427.

Database Registry [Online] Chemical Abstracts Service, Jan. 22, 2001, Columbus, OH.

*Primary Examiner* — Jeffrey S Lundgren
*Assistant Examiner* — Michael J Schmitt
(74) *Attorney, Agent, or Firm* — Dority & Manning, P.A.

(57) ABSTRACT

Described herein are novel compounds that block the activity of LOX family members having good IC50 values, no cellular toxicity below 10 µM, induce sensitization of the cells to doxorubicin, strong activity in a recombinant LOX/LOXL2 activity, and a chemical structure that is drug-like and does not have a PAINS flag, as well as, methods of treatment using the compounds with respect to cancer, organ fibrosis, neurodegenerative and cardiovascular diseases.

20 Claims, 49 Drawing Sheets

Table 1. Structure-Activity Relationship of 4'-methyl-N2-phenyl-[4,5'-bithiazole]-2,2'-diamine Lox Inhibitors

| ID | R1 | R2 | R3 | R4 | R5 | R6 | % LOX cellular activity | LOX cell IC$_{50}$ |
|---|---|---|---|---|---|---|---|---|
| 6232 | H | H | H | NO$_2$ | H | H | 40 | 5 |
| 6402 | CH$_3$CO | H | H | NO$_2$ | H | H | 100 | >10 |
| 6409 | H | H | H | NH$_2$ | H | H | 100 | ND |
| 6411 | H | H | H | N(CH$_3$)$_2$ | H | H | 80 | 10 |
| 6403 | H | H | H | NHCOCH$_3$ | H | H | 20 | 2.5 |
| 6407 | H | H | H | OH | H | H | 100 | 10 |
| 6410 | H | H | H | OCH$_3$ | H | H | 60 | 7.5 |
| 6404 | H | H | H | OCH$_2$CH$_3$ | H | H | 55 | 12.5 |
| 6405 | H | H | H | SO$_2$NH$_2$ | H | H | 5 | 3.5 |
| 6415 | H | H | H | OH | H | CH$_3$ | 10 | 3.5 |
| 6406 | H | H | OH | H | H | H | 35 | ND |
| 6414 | H | H | OCH$_3$ | H | H | H | 70 | ND |
| 6408 | H | OCH$_3$ | H | H | H | H | 75 | ND |

FIG. 13

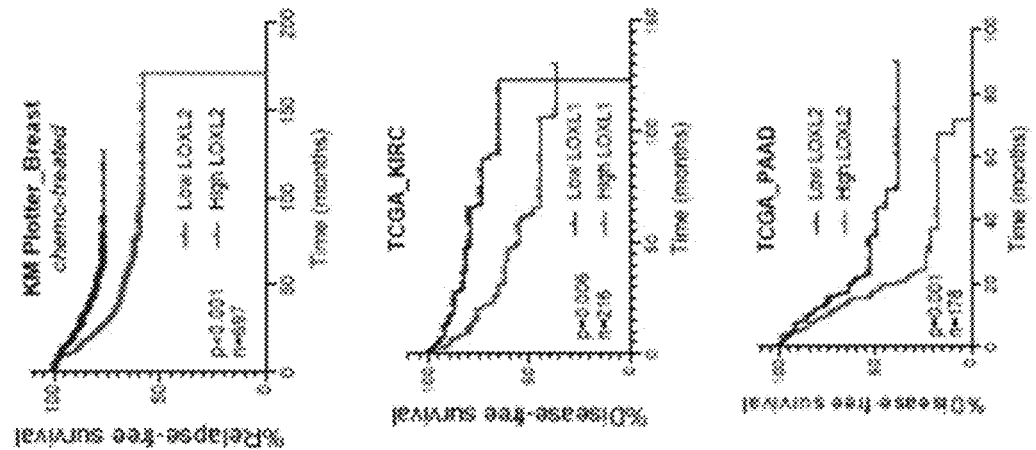
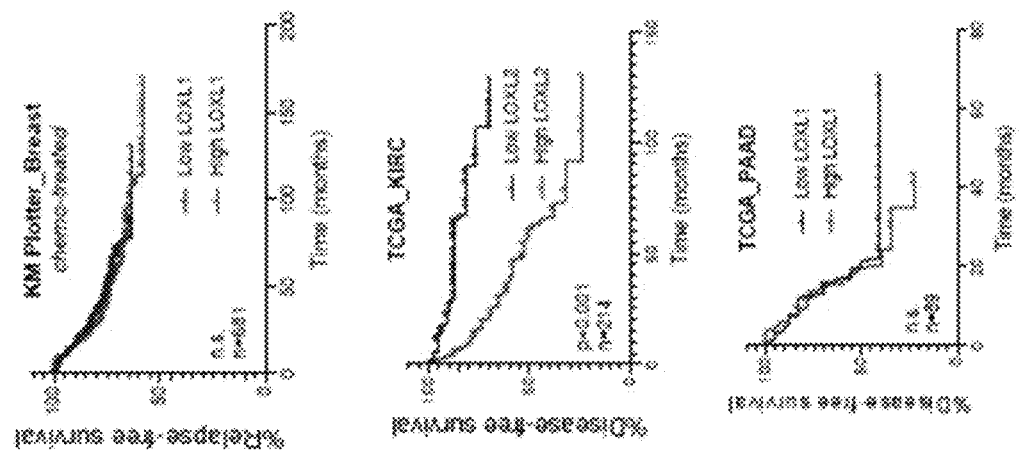
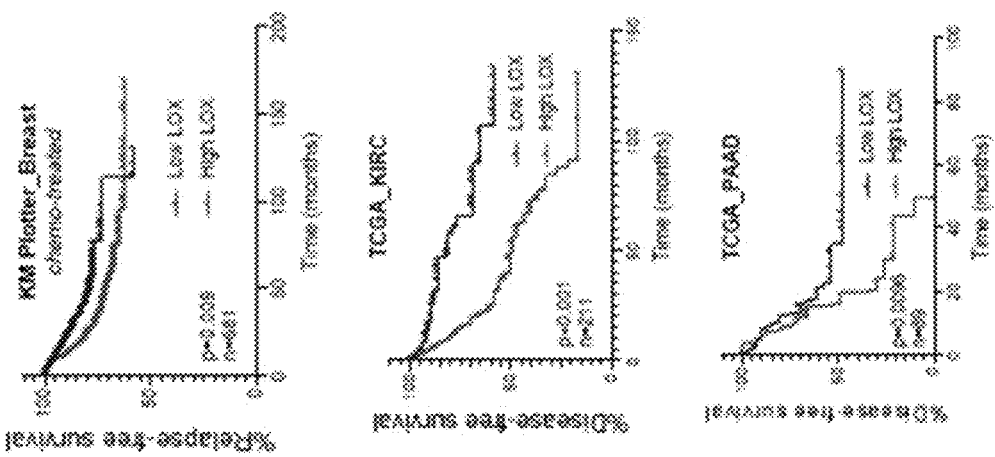
FIG. 23

| DDBS ID | Structure |
|---|---|
| 6232 | 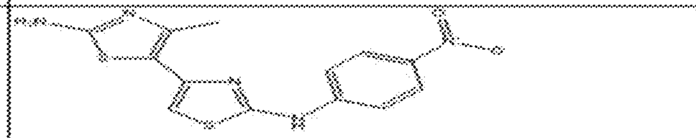 |
| 6398 | 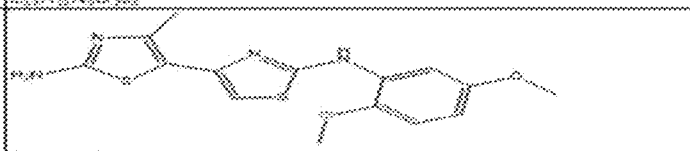 |
| 6399 | 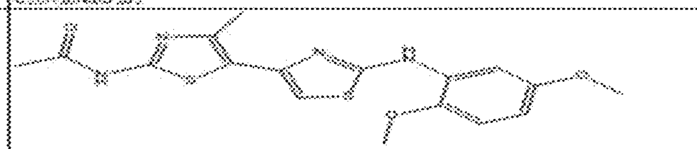 |
| 6400 | 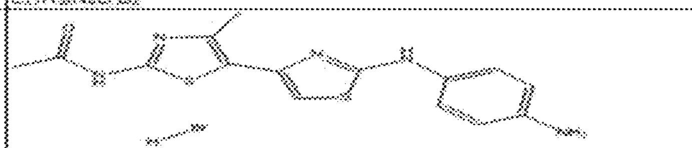 |
| 6401 | 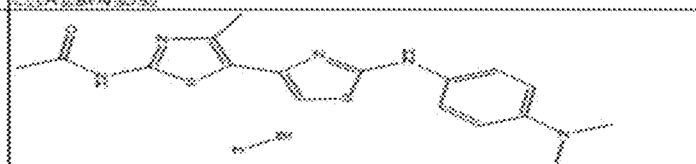 |
| 6402 | 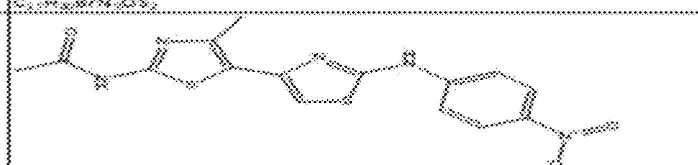 |
| 6403 | 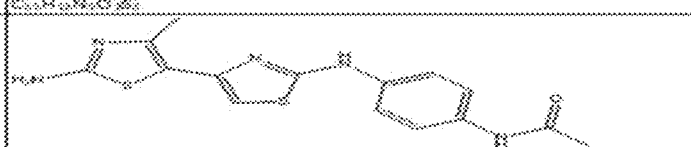 |
| 6404 | 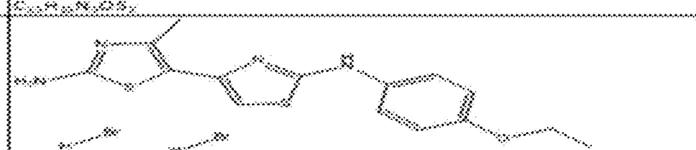 |
| 6405 | 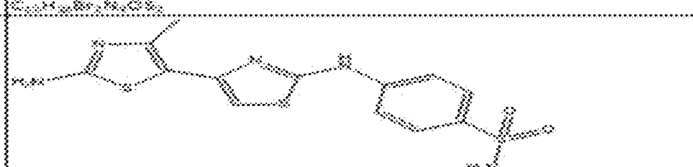 |

FIG. 30

| DDBS ID | Structure |
|---|---|
| 6406 | 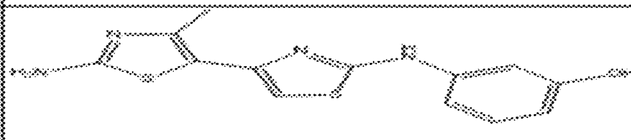 |
| 6407 | 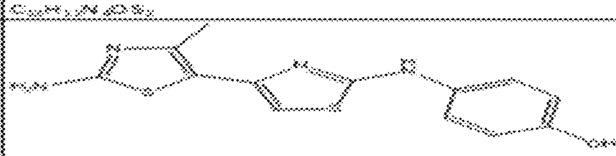 |
| 6408 | 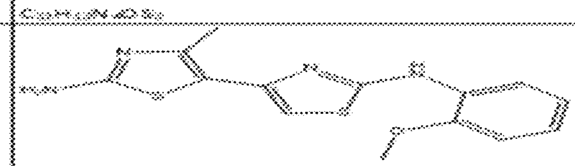 |
| 6409 | 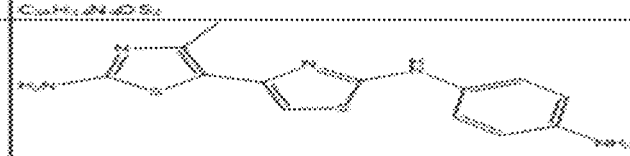 |
| 6410 | 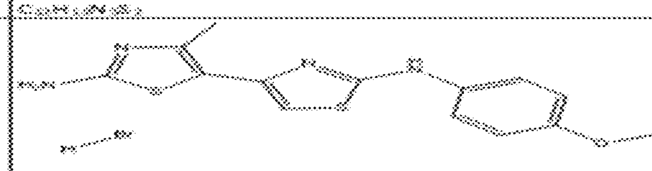 |
| 6411 | 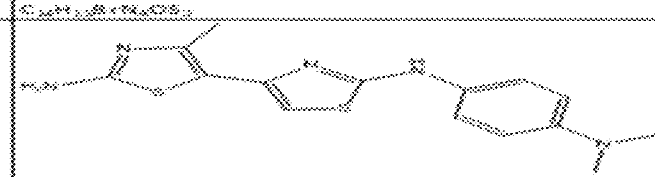 |
| 6412 | 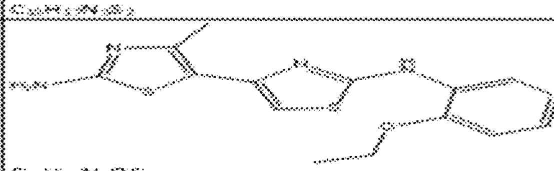 |
| 6413 | 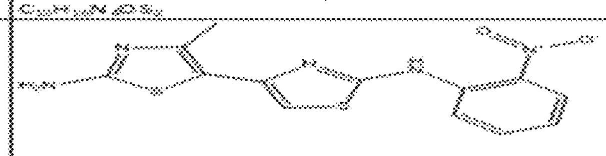 |
| 6414 | 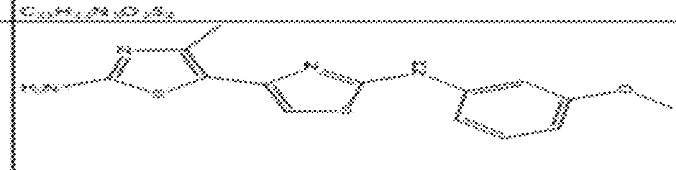 |

FIG. 30 (CONT.)

| DDBS ID | Structure |
|---|---|
| 6415 | 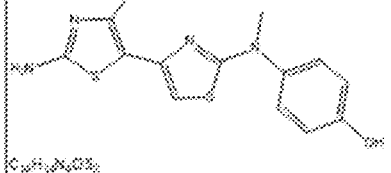 |
| 6424 | 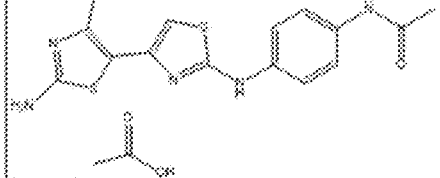 |
| 6425 | 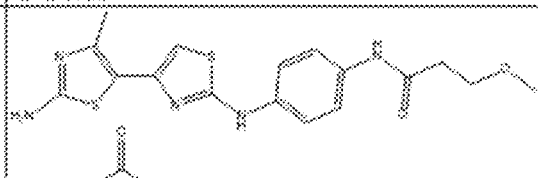 |
| 6426 | 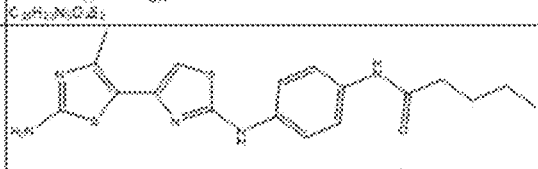 |
| 6432 | 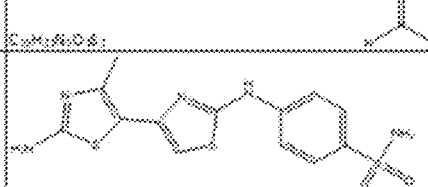 |
| 6433 | 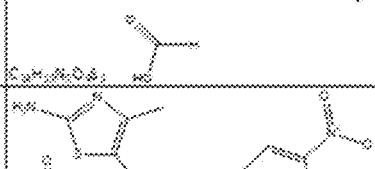 |
| 6439 | 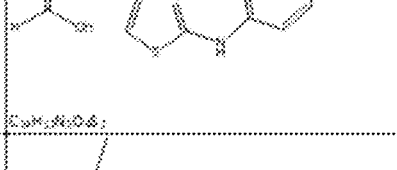 |
FIG. 30 (CONT.)

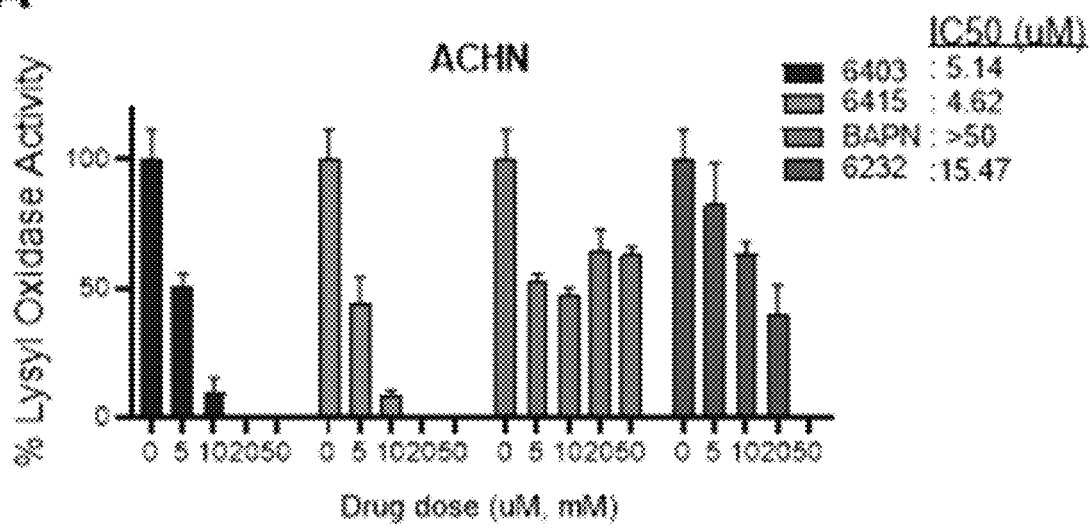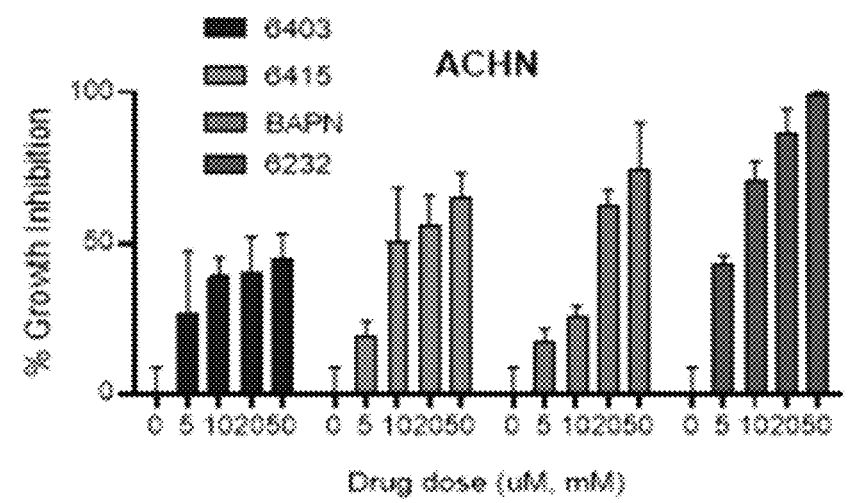
FIG. 38

TABLE 2 Structure-Activity Relationship of 4'-methyl-N2-phenyl-[4,5'-bithiazole]-2,2'-diamine Lox Inhibitors

| ID | R1 | R2 | R3 | R4 | R5 | R6 | % LOX cellul | LOX cell IC$_{50}$ |
|---|---|---|---|---|---|---|---|---|
| 6232 | H | H | H | NO$_2$ | H | H | 40 | 5 |
| 6398 | H | OCH3 | H | H | OCH3 | H | 50 | 5 |
| 6399 | CH3CO | OCH3 | H | H | OCH3 | H | 80 | >10 |
| 6400 | CH3CO | H | H | NH2 | H | H | 90 | >10 |
| 6401 | CH3CO | H | H | N(CH3)2 | H | H | 45 | 4 |
| 6402 | CH$_3$CO | H | H | NO$_2$ | H | H | 100 | >10 |
| 6409 | H | H | H | NH$_2$ | H | H | 100 | >10 |
| 6411 | H | H | H | N(CH$_3$)$_2$ | H | H | 80 | 10 |
| 6403 | H | H | H | NHCOCH$_3$ | H | H | 20 | 1.3 |
| 6425 | H | H | H | NHCO(CH$_2$)$_2$OCH$_3$ | H | H | ND | 7.5 |
| 6426 | H | H | H | NHCO(CH$_2$)$_2$CH$_3$ | H | H | 36 | 2 |
| 6407 | H | H | H | OH | H | H | 100 | 10 |
| 6410 | H | H | H | OCH$_3$ | H | H | 60 | 7.5 |
| 6404 | H | H | H | OCH$_2$CH$_3$ | H | H | 55 | 12.5 |
| 6405 | H | H | H | SO$_2$NH$_2$ | H | H | 5 | 3.5 |
| 6415 | H | H | H | OH | H | CH$_3$ | 10 | 3.5 |
| 6406 | H | H | OH | H | H | H | 35 | >10 |
| 6414 | H | H | OCH$_3$ | H | H | H | 70 | >10 |
| 6408 | H | OCH$_3$ | H | H | H | H | 75 | >20 |

*FIG. 44*

INHIBITORS OF LYSYL OXIDASES

STATEMENT REGARDING FEDERALLY SPONSORED RESEARCH

This invention was made with government support under National Institutes of Health grant number P20 GM109091 and National Institutes of Health grant number RO1 CA267101. The government has certain rights in the invention.

TECHNICAL FIELD

The subject matter disclosed herein is generally directed to pharmaceutically acceptable compositions, and pharmaceutically acceptable salts thereof, and treatment regimens for inhibitions of LOX or LOX family activity wherein the compounds of the present disclosure are useful for treating a variety of diseases, disorders, or conditions, associated with LOX activity and the compounds are also useful for the study of LOX enzymes in biological and pathological phenomena.

BACKGROUND

Lysyl oxidase (LOX) family are copper-dependent amine oxidases. There are five (5) different members of the LOX family proteins (LOX, LOXL1, LOXL2, LOXL3 and LOXL4) that share a high degree of homology at the catalytic carboxy terminal end. See, Barker, H. E., Cox, T. R. & Erler, J. T. The rationale for targeting the LOX family in cancer. *Nat Rev Cancer* 12, 540-552, doi:10.1038/nrc3319 (2012). Importantly, LOX and LOXL1 are synthesized as propeptides and cleaved by bone morphogenic protein 1 (BMP1) metalloprotease to obtain functional enzymes. See, Trackman, P. C., Bedell-Hogan, D., Tang, J. & Kagan, H. Post-translational glycosylation and proteolytic processing of a lysyl oxidase precursor. *Journal Of Biological Chemistry* 267, 8666-8671 (1992). LOX family of proteins mediate conversion of lysine residues in collagen I and elastin precursors into highly reactive aldehydes; thereby triggering crosslinking and stabilization of ECM proteins that regulate cell adhesion, motility, and invasion. See, Kagan, H. M. & Li, W. Lysyl oxidase: properties, specificity, and biological roles inside and outside of the cell. *Journal of Cellular Biochemistry* 88, 660-672, doi:10.1002/jcb.10413 (2003). LOX family members play key roles during embryogenesis and organ development. See, Maki, J. M. et al. Lysyl oxidase is essential for normal development and function of the respiratory system and for the integrity of elastic and collagen fibers in various tissues. *The American Journal of Pathology* 167, 927-936 (2005), Brody, J. S., Kagan, H. & Manalo, A. Lung lysyl oxidase activity: relation to lung growth. *American Review of Respiratory Disease* 120, 1289-1295 (1979), and Wei, S., Gao, L., Wu, C., Qin, F. & Yuan, J. Role of the lysyl oxidase family in organ development. *Experimental and Therapeutic Medicine* 20, 163-172 (2020). While all the LOX family members have a wide distribution in organs; all of them are expressed in the heart and colon. See, Yang, N., Cao, D.-F., Yin, X.-X., Zhou, H.-H. & Mao, X.-Y. Lysyl oxidases: emerging biomarkers and therapeutic targets for various diseases. *Biomedicine & Pharmacotherapy* 131, 110791 (2020), Martins, R. P., Leach, R. E. & Krawetz, S. A. Whole-body gene expression by data mining. *Genomics* 72, 34-42 (2001), Jourdan-Le Saux, C., Tomsche, A., Ujfalusi, A., Jia, L. & Csiszar, K. Central nervous system, uterus, heart, and leukocyte expression of the LOXL3 gene, encoding a novel lysyl oxidase-like protein. *Genomics* 74, 211-218 (2001), Asuncion, L. et al. A novel human lysyl oxidase-like gene (LOXL4) on chromosome 10q24 has an altered scavenger receptor cysteine rich domain. *Matrix Biology* 20, 487-491 (2001), Kim, Y., Boyd, C. D. & Csiszar, K. A New Gene with Sequence and Structural Similarity to the Gene Encoding Human Lysyl Oxidase (*). *Journal of Biological Chemistry* 270, 7176-7182 (1995), and Maki, J. M., Tikkanen, H. & Kivirikko, K. I. Cloning and characterization of a fifth human lysyl oxidase isoenzyme: the third member of the lysyl oxidase-related subfamily with four scavenger receptor cysteine-rich domains. Matrix biology 20, 493-496 (2001). Importantly, all members have so far been associated with cancer, particularly with metastasis and recently with chemoresistance, with LOX (first identified member) and LOXL2 being the most intensely studied members of the family See, Xiao, Q. & Ge, G. Lysyl oxidase, extracellular matrix remodeling and cancer metastasis. *Cancer Microenviron* 5, 261-273, doi: 10.1007/s 12307-012-0105-z (2012).

The inventors have reported that the hypoxia-induced LOX expression is a driver of TNBC chemoresistance. See, Saatci, O. et al. Targeting lysyl oxidase (LOX) overcomes chemotherapy resistance in triple negative breast cancer. *Nat Commun* 11, 2416, doi:10.1038/s41467-020-16199-4 (2020). The inventors demonstrated that LOX not only enhances ECM crosslinking and generates a barrier to chemotherapy, but also fuels cell proliferation and therapy resistance via activating pro-survival integrin signaling in TNBC. See, Id. Inhibition of LOX activity via β-aminopropionitrile (BAPN, a LOX family inhibitor) or shRNA-mediated knockdown of LOX reduced collagen cross-linking, leading to accumulation of doxorubicin in TNBC cells, reduced FAK/Src signaling and led to chemosensitization both in vitro and in vivo. In gastric cancer, LOX expression has been shown to be increased, and it is correlated with the invasion depth and lymph node metastasis while inhibition of LOX via siRNA suppressed the hypoxia-induced EMT of gastric cancer cells. See, Kasashima, H. et al. Lysyl oxidase-like 2 (LOXL2) from stromal fibroblasts stimulates the progression of gastric cancer. *Cancer Letters* 354, 438-446 (2014). High LOX expression is also associated with EMT markers and predicts early recurrence and poor survival in HCC patients. See, Umezaki, N. et al. Lysyl oxidase induces epithelial-mesenchymal transition and predicts intrahepatic metastasis of hepatocellular carcinoma. Cancer science 110, 2033-2043 (2019). Another study showed that LOX expression is required for the mutant p53 driven invasion in pancreatic cancer, and combination of gemcitabine with LOX inhibition led to the tumor necrosis. See, Miller, B. W. et al. Targeting the LOX/hypoxia axis reverses many of the features that make pancreatic cancer deadly: inhibition of LOX abrogates metastasis and enhances drug efficacy. *EMBO Molecular Medicine* 7, 1063-1076 (2015). Furthermore, LOX mRNA is increased in human clear cell renal cell carcinoma (ccRC), and the ectopic expression of LOX resulted in migration and collagen stiffness. See, Di Stefano, V. et al. Major action of endogenous lysyl oxidase in clear cell renal cell carcinoma progression and collagen stiffness revealed by primary cell cultures. *The American Journal of Pathology* 186, 2473-2485 (2016) and Takahashi, M. et al. Gene expression profiling of clear cell renal cell carcinoma: gene identification and prognostic classification. *Proceedings of the National Academy of Sciences* 98, 9754-9759 (2001).

Among the other members of the LOX family, LOXL1 is the least studied member in the cancer context. A few studies showed its oncogenic potential in different cancers. Elevated expression of LOXL1 was found in primary lung cancer tissues, and LOXL1-overexpression in mice led to greater number of lung metastatic nodules. See, Lee, G.-H. et al. Lysyl oxidase-like-1 enhances lung metastasis when lactate accumulation and monocarboxylate transporter expression are involved. *Oncology Letters* 2, 831-838 (2011). In pancreatic cancer patients, LOXL1 mRNA was shown to be increased when compared to normal pancreatic tissue. See, Le Calve, B. et al. Lysyl oxidase family activity promotes resistance of pancreatic ductal adenocarcinoma to chemotherapy by limiting the intratumoral anticancer drug distribution. *Oncotarget* 7, 32100 (2016).

The role of LOXL2 is extensively studied in cancer and fibrosis. In breast cancer, high expression of both LOX and LOXL2 shows a strong correlation with invasive potential of metastatic mammary tumors. See, Kirschmann, D. A. et al. A molecular role for lysyl oxidase in breast cancer invasion. *Cancer Research* 62, 4478-4483 (2002). A high level of LOXL2 expression was also detected in HCC cells and tissues that is associated with the poor disease-free survival and overall survival of HCC patients. See, Ninomiya, G. et al. Significance of Lysyl oxidase-like 2 gene expression on the epithelial-mesenchymal status of hepatocellular carcinoma. *Oncology Reports* 39, 2664-2672 (2018). Higher expression of LOXL2 enhances the invasion ability of pancreatic cancer cells, and a higher distant recurrent rate was found in LOXL2-positive tumors in pancreatic cancer patients. See, Park, J. S. et al. Emerging role of LOXL2 in the promotion of pancreas cancer metastasis. *Oncotarget* 7, 42539 (2016). In primary gastric tumors, higher LOXL2 expression is correlated with higher tumor invasion, higher lymph node metastasis and poorer overall patient survival. See, Peng, L. et al. Secreted LOXL2 is a novel therapeutic target that promotes gastric cancer metastasis via the Src/FAK pathway. *Carcinogenesis* 30, 1660-1669 (2009).

LOXL3 overexpression is observed in gastric cancer, and the oncogenic role of LOXL3 with respect to increasing invasion has been shown in gastric cancer. See, Kasashima, supra. In melanoma, LOXL3 regulates genome integrity by binding several key members of the DNA damage response and promotes tumor growth in vivo. See, Santamaria, P. G. et al. Lysyl oxidase-like 3 is required for melanoma cell survival by maintaining genomic stability. *Cell Death & Differentiation* 25, 935-950 (2018). In addition to the gastric cancer and melanoma, LOXL3 expression was also upregulated in breast cancer, see Jeong, Y. J. et al. Association between lysyl oxidase and fibrotic focus in relation with inflammation in breast cancer. *Oncology Letters* 15, 2431-2440 (2018), myeloproliferative neoplasm, see Tadmor, T. et al. The expression of lysyl-oxidase gene family members in myeloproliferative neoplasms. *American Journal of Hematology* 88, 355-358 (2013), and ovarian carcinoma. See, Dufresne, J. et al. The plasma peptides of ovarian cancer. *Clinical Proteomics* 15, 1-19 (2018). High LOXL4 expression is associated with the poor prognosis of HCC patients, and it induces the intrahepatic and pulmonary metastasis of HCC in in vivo. See, Li, R. et al. Exosome-mediated secretion of LOXL4 promotes hepatocellular carcinoma cell invasion and metastasis. *Molecular cancer* 18, 1-19 (2019). LOXL4 overexpression is associated with poor overall survival in breast cancer patients, see Choi, S. K., Kim, H. S., Jin, T. & Moon, W. K. LOXL4 knockdown enhances tumor growth and lung metastasis through collagen-dependent extracellular matrix changes in triple-negative breast cancer. *Oncotarget* 8, 11977 (2017), and LOXL4 inhibition inhibited the migration and invasion of lung adenocarcinoma cells. See, Xie, S., Liu, G., Huang, J., Hu, H. B. & Jiang, W. miR-210 promotes lung adenocarcinoma proliferation, migration, and invasion by targeting lysyl oxidase-like 4. *Journal of Cellular Physiology* 234, 14050-14057 (2019). Another study in head and neck squamous cell carcinomas (HNSCC) showed that high LOXL4 expression was correlated with tumor stage and lymph node metastasis. See, Weise, J. B. et al. LOXL4 is a selectively expressed candidate diagnostic antigen in head and neck cancer. *European journal of cancer* 44, 1323-1331 (2008).

Human fibrotic diseases are composed of idiopathic pulmonary fibrosis, liver fibrosis, cardiovascular fibrosis and renal fibrosis that share the common feature of excessive deposition of ECM fibrillar proteins, such as collagen in damaged tissues, leading to disrupted ECM homeostasis and organ failure. See, Kim, Y.-M., Kim, E.-C. & Kim, Y. The human lysyl oxidase-like 2 protein functions as an amine oxidase toward collagen and elastin. *Molecular Biology Reports* 38, 145-149 (2011), Chen, L., Li, S. & Li, W. LOX/LOXL in pulmonary fibrosis: potential therapeutic targets. *Journal of Drug Targeting* 27, 790-796 (2019), Yang, J. et al. Targeting LOXL2 for cardiac interstitial fibrosis and heart failure treatment. *Nature Communications* 7, 1-15 (2016), Chien, J. W. et al. Serum lysyl oxidase-like 2 levels and idiopathic pulmonary fibrosis disease progression. *European Respiratory Journal* 43, 1430-1438 (2014), Steppan, J. et al. Lysyl oxidase-like 2 depletion is protective in age-associated vascular stiffening. *American Journal of Physiology-Heart and Circulatory Physiology* 317, H49-H59 (2019), Nave, A. H. et al. Lysyl oxidases play a causal role in vascular remodeling in clinical and experimental pulmonary arterial hypertension. *Arteriosclerosis, Thrombosis, and Vascular Biology* 34, 1446-1458 (2014), and Martinez-Revelles, S. et al. Lysyl oxidase induces vascular oxidative stress and contributes to arterial stiffness and abnormal elastin structure in hypertension: role of p38MAPK. *Antioxidants & Redox Signaling* 27, 379-397 (2017). In addition to role of the LOX family members in cancer, their upregulation and increased activity have fundamental roles in fibrosis. For example, the expression of both LOX and LOXL1 is increased upon TGF-β stimulation and they promote fibrogenesis in hepatic stellate cell and cardiac fibroblast. See, Lu, M., Qin, Q., Yao, J., Sun, L. & Qin, X. Induction of LOX by TGF-β1/Smad/AP-1 signaling aggravates rat myocardial fibrosis and heart failure. *IUBMB Life* 71, 1729-1739 (2019) and Ma, L. et al. Knockdown of LOXL1 inhibits TGF-β1-induced proliferation and fibrogenesis of hepatic stellate cells by inhibition of Smad2/3 phosphorylation. *Biomedicine & Pharmacotherapy* 107, 1728-1735 (2018). Furthermore, LOX expression is increased in myocardial fibrosis which directly contributes to adverse myocardial remodeling in cardiac diseases. See, Spurney, C. F. et al. Dystrophin-deficient cardiomyopathy in mouse: expression of Nox4 and Lox are associated with fibrosis and altered functional parameters in the heart. *Neuromuscular Disorders* 18, 371-381 (2008). In physiological conditions, LOX family members contribute to the integrity and stabilization of a healthy vessel wall. See, Kumari, S., Panda, T. K. & Pradhan, T. Lysyl oxidase: its diversity in health and diseases. *Indian Journal of Clinical Biochemistry* 32, 134-141 (2017). However, early induction and overexpression of LOX led to arterial stiffening in Hutchinson-Gilford Progeria Syndrome. Furthermore, LOX is strongly upregulated in young mice and inhibition of LOX led to improved arterial mechanics and cardiac function. See, von Kleeck, R. et al. Arterial stiffness in Hutchinson-Gilford Progeria Syndrome corrected by inhibition of Lysyl Oxidase. Moreover, both cardiac hypertrophy and disfunction are associated with LOX overexpression which may be targeted for the clinical management of hypertrophy and heart failure. See, Galán, M. et al. Lysyl oxidase overexpression accelerates cardiac remodeling and aggravates angiotensin II—induced hypertrophy. *The FASEB Journal* 31, 3787-3799 (2017). Overall, these studies show the key roles of LOX and other LOX family members in fibrosis.

In addition to the role of LOX family members in cancer and fibrotic diseases, aberrant lysyl oxidase activity has also been shown in other pathological conditions, including diabetes, neurodegeneration and adipose tissue dysfunction. See, Wilhelmus, M. M., Bol, J. G., van Duinen, S. G. & Drukarch, B. Extracellular matrix modulator lysyl oxidase colocalizes with amyloid-beta pathology in Alzheimer's disease and hereditary cerebral hemorrhage with amyloidosis—Dutch type. *Experimental Gerontology* 48, 109-114 (2013) and Pastel, E. et al. Lysyl oxidase and adipose tissue dysfunction. *Metabolism* 78, 118-127 (2018). For example, LOX overexpression is induced by hypoxia and inflammation in adipose tissue with obesity. See, Pastel, supra. In addition LOX expression is induced in diabetes and led to apoptosis in rat retinal endothelial cells while siRNA knockdown of LOX reduced diabetes-induced LOX expression and prevented vascular leakage associated with diabetic retinopathy. See, Chronopoulos, A., Tang, A., Beglova, E., Trackman, P. C. & Roy, S. High glucose increases lysyl oxidase expression and activity in retinal endothelial cells: mechanism for compromised extracellular matrix barrier function. *Diabetes* 59, 3159-3166 (2010). High LOX and LOXL2 level were observed in choroid neovascularization and the inhibition of LOX and LOXL2 through neutralizing anti-LOX and LOXL2 antibodies showed the functional contribution of LOX and LOXL2 in diabetic retinopathy. See, Roy, S., Ha, J., Trudeau, K. & Beglova, E. Vascular basement membrane thickening in diabetic retinopathy. *Current eye research* 35, 1045-1056 (2010). Under physiological conditions, the LOX expression is low in rat brain; however, it accumulates in the lesion after brain injury. See, Gilad, G. M., Kagan, H. M. & Gilad, V. H. Lysyl oxidase, the extracellular matrix-forming enzyme, in rat brain injury sites. *Neuroscience letters* 310, 45-48 (2001). Interestingly, high LOX activity is observed during the plaque formation in Alzheimer's disease (AD) through ECM modulation. See, Gilad, G. M., Kagan, H. M. & Gilad, V. H. Evidence for increased lysyl oxidase, the extracellular matrix-forming enzyme, in Alzheimer's disease brain. *Neuroscience Letters* 376, 210-214 (2005).

Given the multifaceted functions of the LOX family members in fibrosis, cancer and other diseases, there is huge interest to identify and develop potent and tolerable LOX or LOX family inhibitors. BAPN is the earliest and most commonly used research tool to inhibit LOX; it inhibits all LOX family members and showed toxicity in the clinic. See, Keiser, H. R. & Sjoerdsma, A. Studies on beta-aminopropionitrile in patients with scleroderma. *Clin Pharmacol Ther* 8, 593-602, doi:10.1002/cpt196784593 (1967) and Spencer, P. & Schaumburg, H. Lathyrism: a neurotoxic disease. *Neurobehavioral toxicology and teratology* 5, 625-629 (1983). Simtuzumab, a humanized monoclonal antibody binding LOXL2, was tested for patients with fibrosis in three different clinical trials; however, these studies either terminated due to lack of efficacy (NCT01769196) or resulted in no benefit (NCT01672866 and NCT01672879). Furthermore, no clinical benefit has been reported with Simtuzumab in combination with chemotherapy in the first and second-line settings in pancreatic and colorectal adenocarcinoma patients, respectively. See, Benson, A. B., 3rd et al. A Phase II Randomized, Double-Blind, Placebo-Controlled Study of Simtuzumab or Placebo in Combination with Gemcitabine for the First-Line Treatment of Pancreatic Adenocarcinoma. *Oncologist* 22, 241-e215, doi:10.1634/theoncologist.2017-0024 (2017) and Hecht, J. R. et al. A Phase II, Randomized, Double-Blind, Placebo-Controlled Study of Simtuzumab in Combination with FOLFIRI for the Second-Line Treatment of Metastatic KRAS Mutant Colorectal Adenocarcinoma. *Oncologist* 22, 243-e223, doi:10.1634/theoncologist.2016-0479 (2017). More recently, a phenoxypyricline-containing small molecule, PAT-1251, an inhibitor of LOXL2/LOXL3, showed promising results as an anti-fibrotic agent in pre-clinical models, see Rowbottom, M. W. et al. Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2). *J Med Chem* 60, 4403-4423, doi:10.1021/acs.jmedchem.7b00345 (2017), and it is currently in Phase IIa clinical trial for myelofibrosis (NCT04679870). The haloallylamine-based small molecule inhibitors, PXS-S1A and PXS-S2A were potent against LOX/LOXL2 and LOXL2, respectively, and the former one inhibited lung and liver metastasis. See, Chang, J. et al. Pre-clinical evaluation of small molecule LOXL2 inhibitors in breast cancer. *Oncotarget* 8, 26066-26078, doi:10.18632/oncotarget.15257 (2017). An orally bioavailable aminomethylenethiophene (AMT)-based inhibitor, CCT365623 is active against LOX/LOXL2 and led to significant reduction in metastasis in a breast cancer animal model. See, Leung, L. et al. Anti-metastatic Inhibitors of Lysyl Oxidase (LOX): Design and Structure-Activity Relationships. *J Med Chem* 62, 5863-5884, doi:10.1021/acs.jmedchem.9b00335 (2019). A pan-lysyl oxidase inhibitor PXS-5505 was well-tolerated in healthy volunteers and is now being tested in patients with primary, postpolycythemia vera (a myeloproliferative neoplasm) or post-essential thrombocythemia myelofibrosis. See, How, J. et al. Evaluation of a Pan-Lysyl Oxidase Inhibitor, Pxs-5505, in Myelofibrosis: A Phase I, Randomized, Placebo Controlled Double Blind Study in Healthy Adults. *Blood* 136, doi:10.1182/blood-2020-139223 (2020). Recently, the FDA cleared the test of PXS-5505 in combination with a PD-L1 inhibitor and an anti-VEGF drug as first line therapy in newly diagnosed patients with unresectable HCC carcinoma (NCT05109052). In addition, Cyclosporin (CsA) is one of the most commonly used drugs after the solid organ transplantation and also it is the main cause of uremia. Importantly, combinatorial treatment with CsA and Pan-LOX inhibitor, PXS-5505 attenuated uremia and progressive nephropathy. See, Nguyen, L. T. et al. Lysyl oxidase inhibitors attenuate cyclosporin A-induced nephropathy in mouse. *Scientific reports* 11, 1-12 (2021). Despite the presence of several on-going clinical trials using LOX family inhibitors in several diseases, there is still no LOX inhibitor approved by the FDA, showing the necessity of developing novel, efficacious and tolerable inhibitors against LOX or LOX family members.

According to the American Cancer Society, there will be an estimated 1.8 million new cancer cases diagnosed and 606,520 cancer deaths in the United States. This number may be multiplied by at least eight to estimate the world cancer incidence/death numbers. Heart diseases are the leading cause of death followed by cancer. Neurodegenerative diseases and fibrosis are also very common. Cancer is worldwide problem, and different therapy options are available e.g., chemotherapy, immunotherapy and an antibody-drug conjugate are available for patients. See www.cancer.org.

Accordingly, it is an object of the present disclosure to provide novel compounds that block the activity of lysyl oxidases family members, with a potential to be developed further as cancer drugs to inhibit resistance to conventional therapies and metastasis, or as drugs to treat fibrotic disease.

Citation or identification of any document in this application is not an admission that such a document is available as prior art to the present disclosure.

SUMMARY

The above objectives are accomplished according to the present disclosure by providing a method for inhibiting lysyl oxidases. The method may include administering a therapeutically effective amount of a compound or its pharmaceutically acceptable salt having formula I;

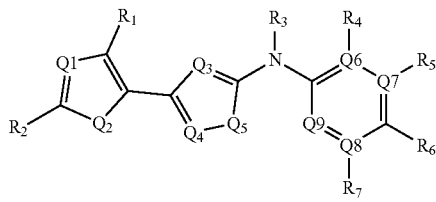

wherein: R1 is $CH_3$, $R_2$ is H, $NH_2$ and NHR, $R_3$ is H or $CH_3$, $R_4$ is H, $R_5$ is H, $R_6$ is $NO_2$, $C_2OH$, $NHCOCH_3$, or OH, $R_7$ is H, Q1 is N, Q2 is S, Q3 is N, Q4 is CH, Q5 is S, Q6 is CH, Q7 is CH, Q8 is C; and Q9 is CH wherein the compound or its pharmaceutically acceptable salt inhibits cell-based lysyl oxidase activity and/or recombinant protein based lysyl oxidase activity assays.

Further, the therapeutically effective amount of the compound or its pharmaceutically acceptable salt may be administered to treat a neurodegenerative disease, an angiogenesis-related disease, Alzheimer's disease, fibrosis including: liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis, diabetes, cerebral hemorrhage with amyloidosis, cardiac hypertrophy, Hutchinson-Gilford Progeria Syndrome, retinopathy, chemoresistance, and/or a kidney disorder including: kidney fibrosis, renal fibrosis, acute kidney injury, chronic kidney disease, diabetic nephropathy, glomerulosclerosis, vesicoureteral reflux, tubulointerstitial renal fibrosis and/or glomerulonephritis. Still further, the cancer may be selected from the group comprising lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; myelofibrosis, kidney cancer; cancer of the head and neck; cancer of the stomach; multiple myeloma; testicular cancer; germ cell tumor; neuroendocrine tumor; cervical cancer; oral cancer, carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma and/or a leiomysarcoma. Again, the compound or its pharmaceutically acceptable salt may have formula:

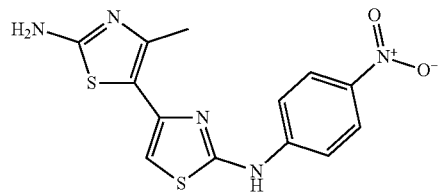

Moreover, the compound or its pharmaceutically acceptable salt may have formula:

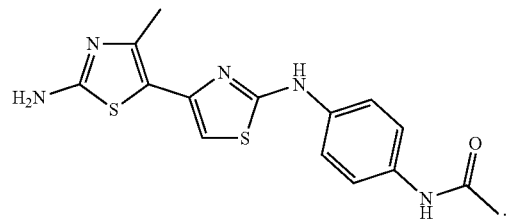 [SMILES: CC(=O)Nc1ccc(Nc2nc(-c3sc(N)nc3C)cs2)cc1]

Indeed, the compound or its pharmaceutically acceptable salt may have formula:

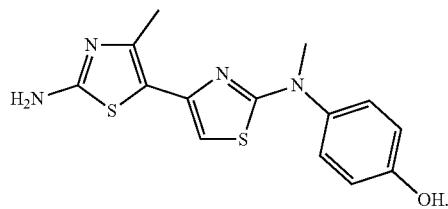 [SMILES: Cc1nc(N)sc1-c1csc(N(C)c2ccc(O)cc2)n1]

Still yet, the compound or its pharmaceutically acceptable salt may have formula:

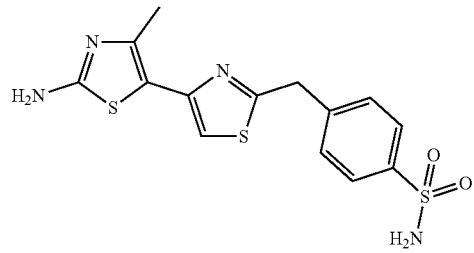 [SMILES: Cc1nc(N)sc1-c1csc(Cc2ccc(S(N)(=O)=O)cc2)n1]

Further yet, the therapeutically effective amount of a compound or its pharmaceutically acceptable salt may be employed as an anti-cancer agent wherein cancer is selected from the group comprising lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; myelofibrosis, kidney cancer; cancer of the head and neck; cancer of the stomach; multiple myeloma; testicular cancer; germ cell tumor; neuroendocrine tumor; cervical cancer; oral cancer, carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma and/or a leiomysarcoma. Again still, the therapeutically effective amount of the compound or its pharmaceutically acceptable salt may be administered to reduce cardiotoxicity side effects of chemotherapy and/or immunotherapy. Yet still again, the therapeutically effective amount of the compound or its pharmaceutically acceptable salt may be administered as a single agent or in combination with chemotherapy, immunotherapy and/or radiotherapy in both adjuvant and neo-adjuvant settings. Again further, the therapeutically effective amount of the compound or its pharmaceutically acceptable salt may be administered to induce metastasis inhibition. Furthermore, the therapeutically effective amount of the compound or its pharmaceutically acceptable salt may be administered with a second therapeutic agent selected from an anti-cancer agent, an anti-inflammatory agent, an anti-hypertensive agent, an anti-fibrotic agent, an anti-angiogenic agent, and/or an immunosuppressive agent.

The current disclosure also provides a novel compound for inhibiting lysyl oxidases having formula:

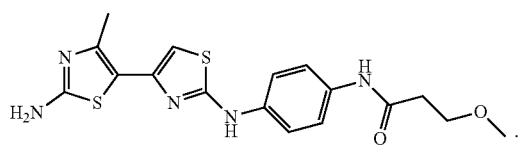 [SMILES: COCCC(=O)Nc1ccc(Nc2nc(-c3sc(N)nc3C)cs2)cc1]

Still further, the compound or its pharmaceutically acceptable salt may be administered in a therapeutically effective amount to treat a neurodegenerative disease, an angiogenesis-related disease, Alzheimer's disease, fibrosis including: liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis, diabetes, cerebral hemorrhage with amyloidosis, cardiac hypertrophy, Hutchinson-Gilford Progeria Syndrome, retinopathy, chemoresistance, and/or a kidney disorder including: kidney fibrosis, renal fibrosis, acute kidney injury, chronic kidney disease, diabetic nephropathy, glomerulosclerosis, vesicoureteral reflux, tubulointerstitial renal fibrosis and/or glomerulonephritis. Yet again, the novel compound or its pharmaceutically acceptable salt may be administered as a single agent or in combination with chemotherapy, immunotherapy and/or radiotherapy in both adjuvant and neo-adjuvant settings. Still yet again, the compound or its pharmaceutically acceptable salt may be administered with a second therapeutic agent selected from an anti-cancer agent, an anti-inflammatory agent, an anti-hypertensive agent, an anti-fibrotic agent, an anti-angiogenic agent, and/or an immunosuppressive agent.

The current disclosure further provides a novel compound for inhibiting lysyl oxidases having formula:

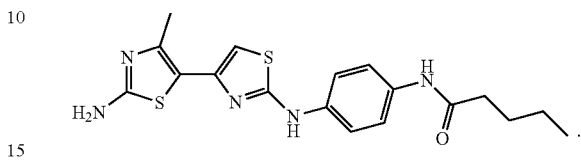

Further, the novel compound or its pharmaceutically acceptable salt may be administered in a therapeutically effective amount to treat a neurodegenerative disease, an angiogenesis-related disease, Alzheimer's disease, fibrosis including: liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis, diabetes, cerebral hemorrhage with amyloidosis, cardiac hypertrophy, Hutchinson-Gilford Progeria Syndrome, retinopathy, chemoresistance, and/or a kidney disorder including: kidney fibrosis, renal fibrosis, acute kidney injury, chronic kidney disease, diabetic nephropathy, glomerulosclerosis, vesicoureteral reflux, tubulointerstitial renal fibrosis and/or glomerulonephritis. Even further, the compound or its pharmaceutically acceptable salt may be administered as a single agent or in combination with chemotherapy, immunotherapy and/or radiotherapy in both adjuvant and neo-adjuvant settings. Still yet again, the compound or its pharmaceutically acceptable salt may be administered with a second therapeutic agent selected from an anti-cancer agent, an anti-inflammatory agent, an anti-hypertensive agent, an anti-fibrotic agent, an anti-angiogenic agent, and/or an immunosuppressive agent.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which:

FIG. 13 shows Table 1, Structure-Activity Relationship of 4'-methyl-N2-phenyl-[4,5'-bithiazole]-2,2'-diamine Lox Inhibitors.

FIG. 23 shows association of the expression of LOX, LOXL1 and LOXL2 with survival in breast, pancreatic and kidney cancer patients.

FIG. 30 shows LOX inhibitors generated based on SAR analysis.

FIG. 38 shows dose dependent inhibition of cellular LOX activity and growth inhibition in 3D upon treatment with 6232 and its analogs, 6403 and 6415.in ACHN cancer cell line.

FIG. 44 shows Table 2, structure-activity relationship of 4'-methyl-N2-phenyl-[4,5'-bithiazole]-2,2'-diamine Lox inhibitors.

Figure 1:
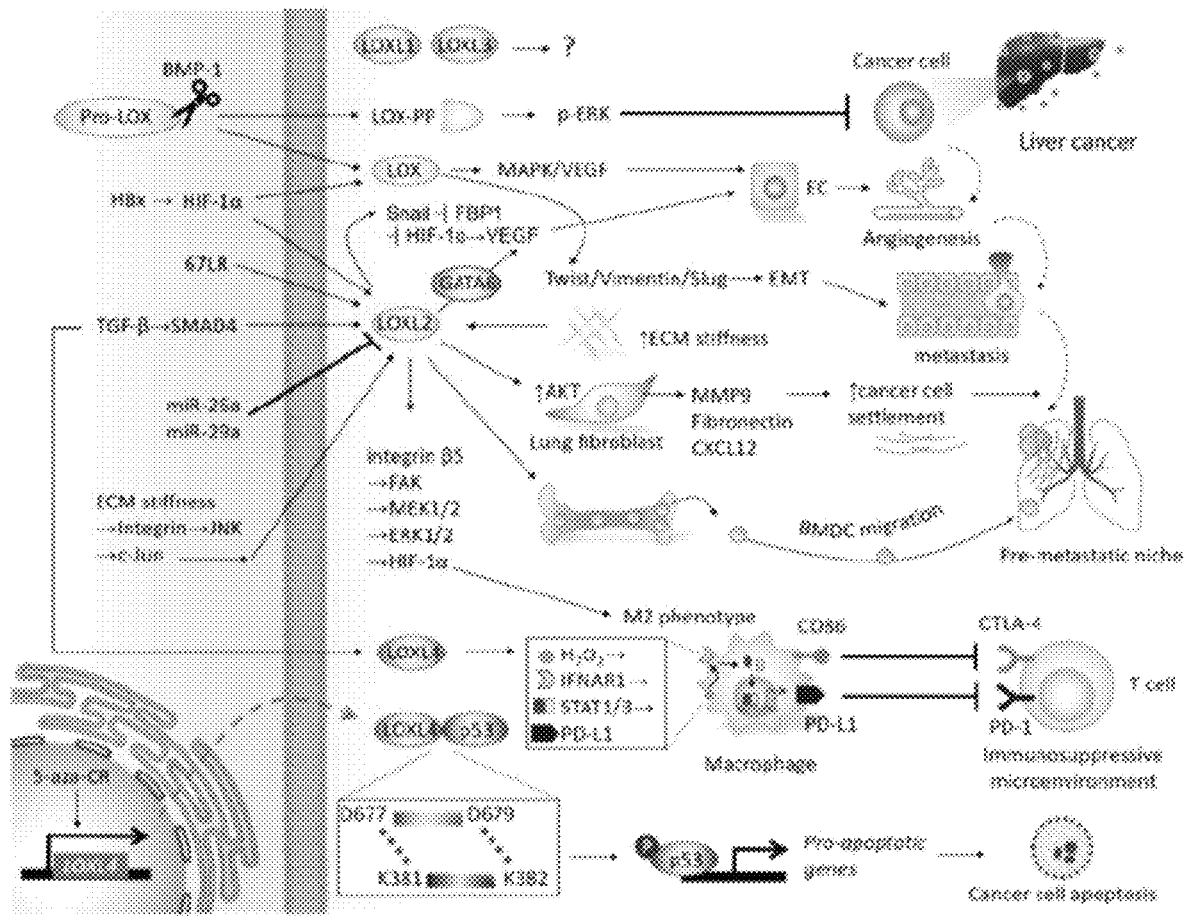
FIG. 1 shows a diagram of extracellular matrix remodeling.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g., given data set, art accepted standard, and/or with e.g., a given confidence interval (e.g., 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g., by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, sub arachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basal cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, Hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sezary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "polymer" refers to molecules made up of monomers repeat units linked together. "Polymers" are understood to include, but are not limited to, homopolymers, copolymers, such as for example, block, graft, random and alternating copolymers, terpolymers, etc. and blends and modifications thereof. "A polymer" can be a three-dimensional network (e.g., the repeat units are linked together left and right, front and back, up and down), a two-dimensional network (e.g., the repeat units are linked together left, right, up, and down in a sheet form), or a one-dimensional network (e.g., the repeat units are linked left and right to form a chain). "Polymers" can be composed, natural monomers or synthetic monomers and combinations thereof. The polymers can be biologic (e.g., the monomers are biologically important (e.g., an amino acid), natural, or synthetic.

As used herein, the term "radiation sensitizer" refers to agents that can selectively enhance the cell killing from irradiation in a desired cell population, such as tumor cells, while exhibiting no single agent toxicity on tumor or normal cells.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g., mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g., a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of a pharmaceutical formulation thereof such as any of the methods described in greater detail elsewhere herein.

While dramatic advances have been made in the treatment and curation of cancer, disease progression following first-line treatment, accompanied by the spread of cancer to distant organs is inevitable in many cases and associated with cancer mortality. Proteins that re-model the extracellular matrix (ECM) which surrounds the tumors and helps them grow and invade distant organs are attractive therapeutic targets not only for cancer but also for other diseases involving excessive ECM deposition such as fibrotic diseases, neurodegenerative and cardiovascular diseases.

Lysyl oxidase family proteins are composed of five members (LOX and four related enzymes, LOXL1-4). The main function of lysyl oxidases is to catalyze the crosslinking of extracellular matrix (ECM) components, mainly collagens and elastin, and thus re-modelling the ECM. Given the crucial roles they play in maintaining tissue homeostasis, deregulation of lysyl oxidases may lead to various diseases, including cancer, organ fibrosis, neurodegenerative and cardiovascular diseases. Each LOX enzyme has several overlapping as well as unique functions. LOX and LOXL2 proteins have been implicated in progression and metastasis of several types of cancers, such as breast, pancreas, and lung adenocarcinomas. Their role in promoting breast cancer metastasis has been associated with their ability to increase the stiffness of the tumors and to enhance collagen crosslinking at the metastatic site, thus preparing the required niche for metastatic out-growth. They can also stimulate endothelial cells and promote angiogenesis. In addition, published data from us and others have implicated a role of LOX proteins in therapy resistance of cancers. LOX/LOXLs can regulate cancer cell invasion by promoting epithelial-mesenchymal transition (EMT), stabilization of EMT transcription factors or repression of epithelial gene transcription. They also have non-canonical functions such as regulation of gene transcription. Most importantly, high expression of LOX/LOXLs is associated with poor prognosis in different cancers. In addition to cancer, LOX family proteins have also been linked to fibrotic disease, extending the applicability of LOX/LOXL targeting strategies. In an effort to identify novel compounds targeting LOX proteins, the inventors executed a high-throughput screening program and identified a number of initial hit compounds which reduced lysyl oxidase activity in a cellular assay with minimum cell toxicity. A fresh batch of the shortlisted compounds were then purchased, and the dose-dependent effects on cell viability and lysyl oxidase activity were validated. The inventors then tested the effects of compounds on chemotherapy sensitization and also tested the direct inhibitory effects on LOX and LOXL2 activity using recombinant proteins. A final filter was the assessment of the compounds drug-likeness and the ease of making new analogues through synthetic chemistry. One series based upon a 4'-methyl-N2-phenyl-[4,5'-bithiazole]-2,2'-diamine core structure fulfilled all of these criteria and our current lead inhibitor from this series is 4-((2'-amino-4'-methyl-[4,5'-bithiazol]-2-yl)(methyl)amino)phenol. This compound is a non-selective inhibitor of the LOX family of enzymes.

In cancer, ECM is frequently remodeled by cancer cells themselves or tumor-associated stromal cells, leading to increased tumor stiffness and thus, enhanced proliferation, migration and invasion. ECM remodeling at the metastatic site can also trigger colonization and metastatic outgrowth. Besides cancer, disruption of ECM homeostasis may also lead to organ fibrosis, neurodegenerative and cardiovascular diseases. FIG. 1 shows a diagram of extracellular matrix remodeling. See, Hung-Yu Lin et al, 2020, *International Journal of Molecular Sciences*.

Given the highly critical functions they have in ECM remodeling, targeting LOX/LOXLs is an attractive therapeutic strategy that will benefit the treatment of ECM-driven diseases. BAPN is the most widely used LOX family inhibitor. However, due to its simple chemical structure, it is highly unspecific leading to severe toxicity. It also lacks sites amenable for chemical modification, and thus precludes preclinical optimization. A few studies reported LOXL2-specific inhibitor and LOX/LOXL inhibitors. See Tang et al., Lysyl oxidase drives tumor progression by trapping EGF receptors at the cell surface (2017). Tang et al. developed an orally bioavailable LOX/LOXL2 inhibitor named CCT365623. This inhibitor is an aminomethylenethiophene (AMT) based inhibitor. Treatment with CCT365623, daily by oral gavage with 70 mg/kg dose decreased tumor growth and reduced metastasis in breast cancer models. See FIG. 2, which shows graphical and visual analysis of tumor cell growth after birth and metastasis data resulting from treatment with CCT365623. See, Tang et al., Lysyl Oxidase Drives Tumor Progression by Trapping EFT Receptors at the Cell Surface, DOI: 10.1038/ncomms14909.

Further, the non-competitive LOXL2 targeting humanized monoclonal antibody, Simtuzumab showed beneficial effects in various preclinical models of fibrosis and cancer. It has also been tested in several clinical trials in the context of fibrotic diseases as well as cancer. For cancer, a phase II clinical trial was conducted with Simtuzumab in combination with gemcitabine to treat pancreatic cancer patients (NCT01472198). Although the antibody was well-tolerated, the clinical benefit was minimal due to lack of efficacy. See FIG. 3, which shows an illustration of interaction between LOXL2, tumor cells and collagen fibers. See, Sandra Ferreira S. et al, *Antioxidants*, 2021. The lack of efficacy with LOXL2-targeting antibody may be attributed to the fact that Simtuzumab only targets extracellular LOXL2 which is apparently not effective enough owing to several intracellular functions of the LOX family proteins (Sandra Ferreira S. et al, *Antioxidants*, 2021).

Figure 4:
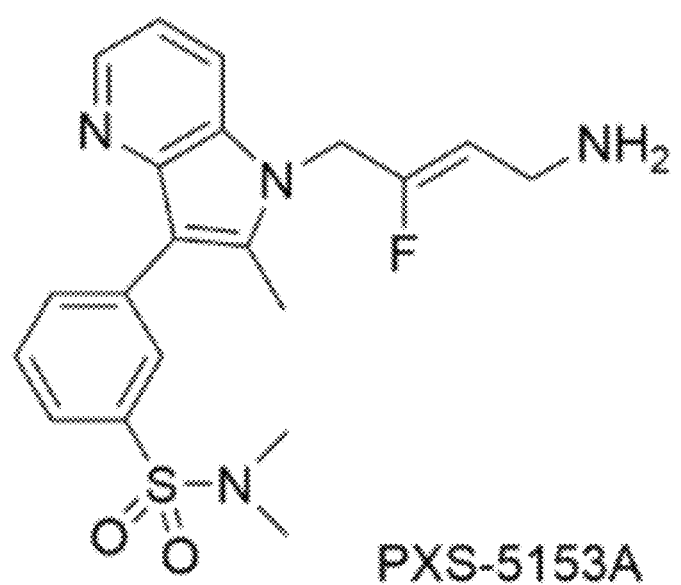
FIG. 4 shows the molecular structure of PXS-5153A.

Therefore, targeting LOX enzymes with small molecule inhibitors that will inhibit both the intracellular and extracellular LOX functions should be much more effective. FIG. 4 shows the molecular structure of PXS-5153A. See, (Schilter H et al., 2018, J. Cell. Mol. Med). The small molecule PXS-5153A demonstrated complete and irreversible enzyme inhibition for LOXL2 and LOXL3. PXS-5153A was shown to reduce LOXL2-mediated collagen oxidation and cross-linking, in a dose-dependent manner in vitro. This dual LOXL2/LOXL3 inhibitor has shown beneficial effects in models of liver fibrosis and myocardial infarction (Schilter H et al, 2018, *J. Cell. Mol. Med.*). Pharmaxis has developed an orally bioavailable pan-lysyl oxidase inhibitor PXS-5505, inhibiting all lysyl oxidase family members. The compound has shown significant reductions in fibrosis in in vivo models of kidney fibrosis, lung fibrosis, myelofibrosis (a rare type of blood cancer) and pancreatic cancer. It also demonstrated an excellent safety profile and was well tolerated in healthy male volunteers (How, J. et al, 2020, *Blood*). A Phase 1c/2a clinical trial in myelofibrosis patients is now planned whose results are expected by 2023.

Figure 5:
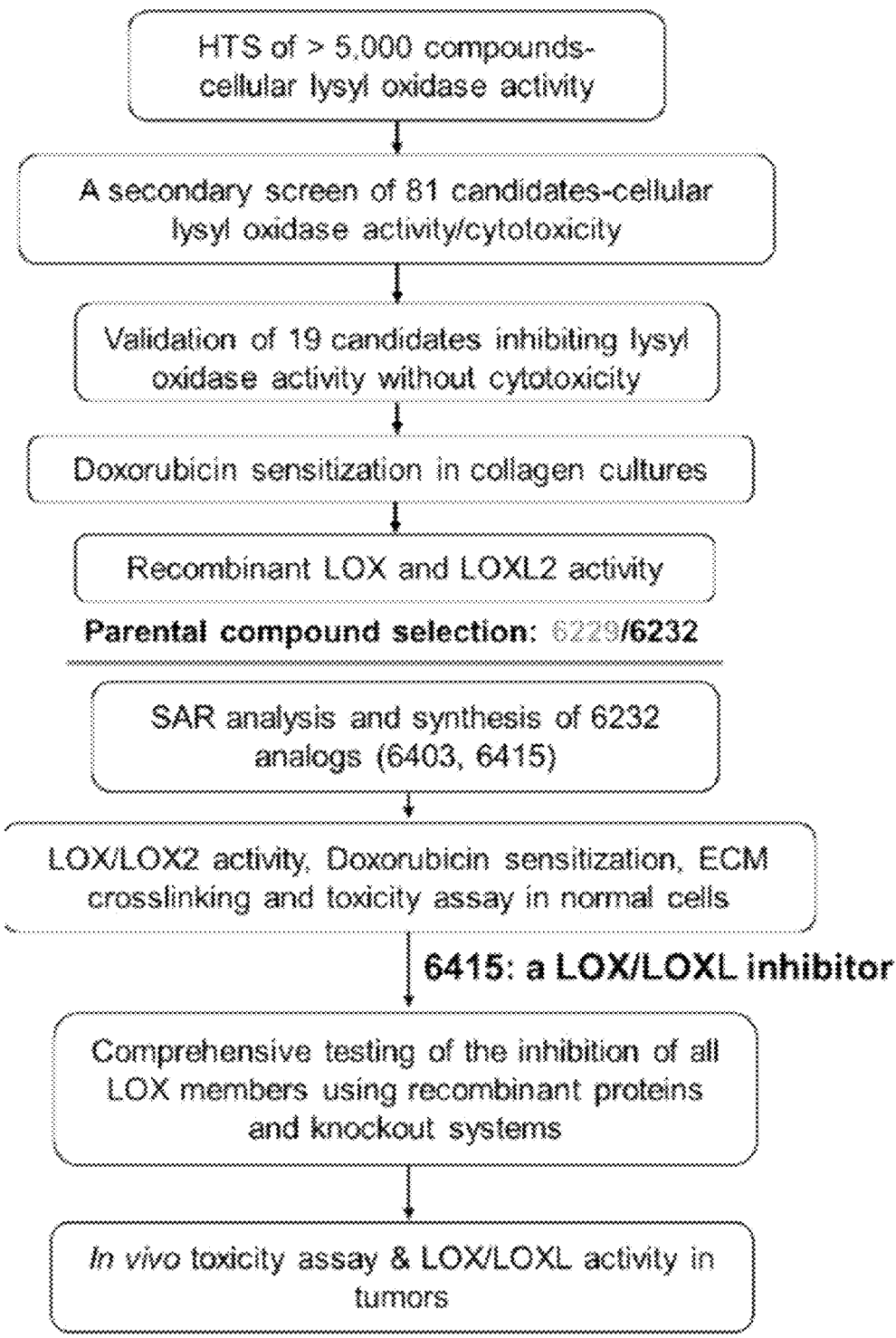
FIG. 5 shows one embodiment of a process for identification and characterization of novel LOX/LOXL inhibitors.
Figure 6:
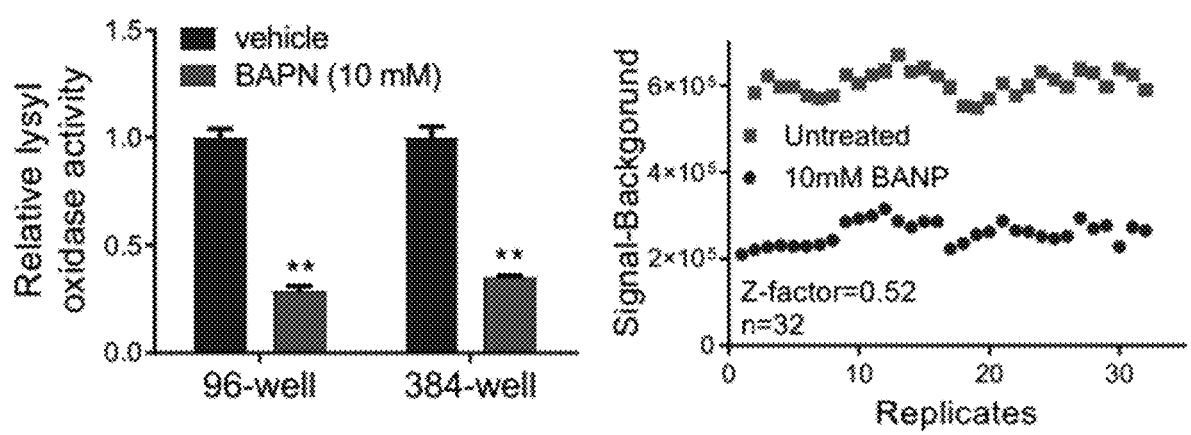
FIG. 6 shows relative lysyl oxidase activity and signal background for potential inhibitors.
Figure 7:
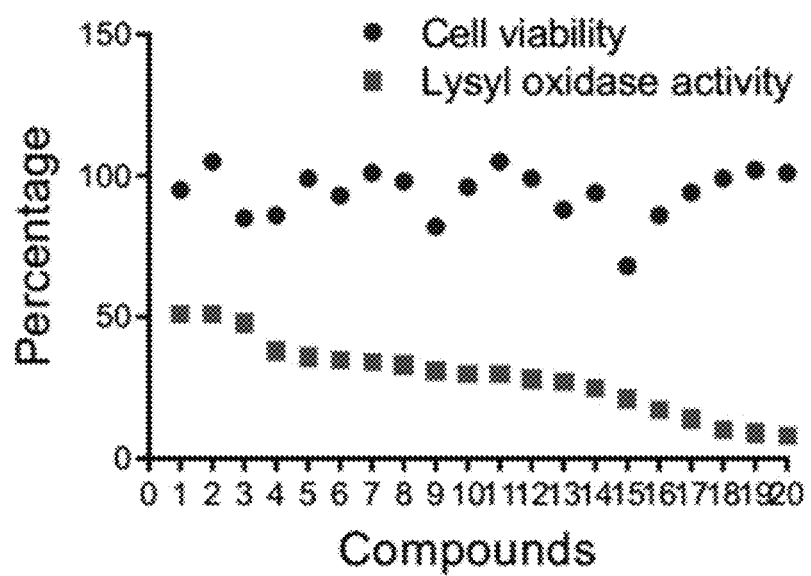
FIG. 7 shows a comparison of cell viability and lysyl oxidase activity for target compounds.
Figure 8:
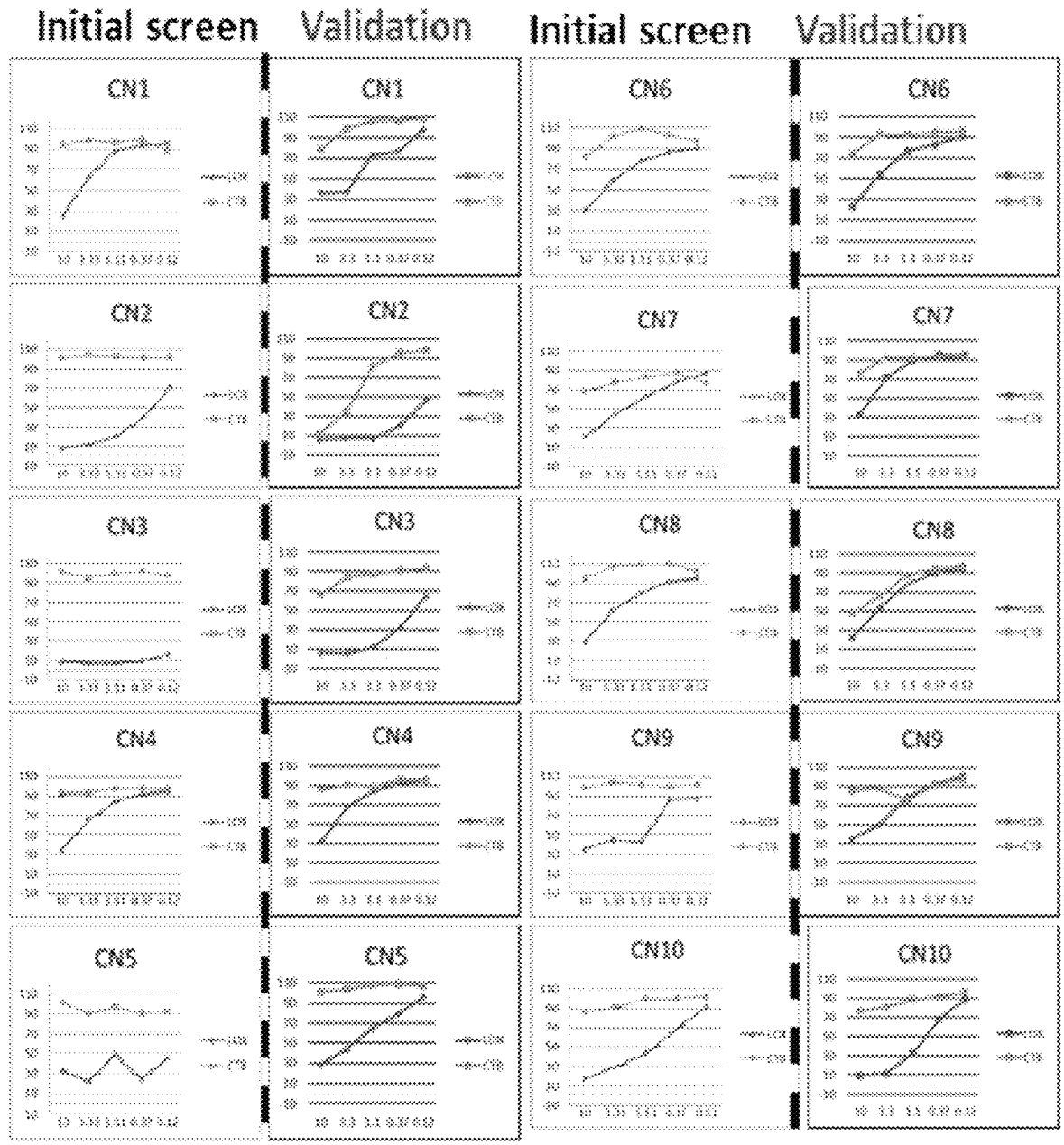
FIG. 8 shows cell viability and lysyl oxidase activity for twenty specific target compounds.
Figure 8:
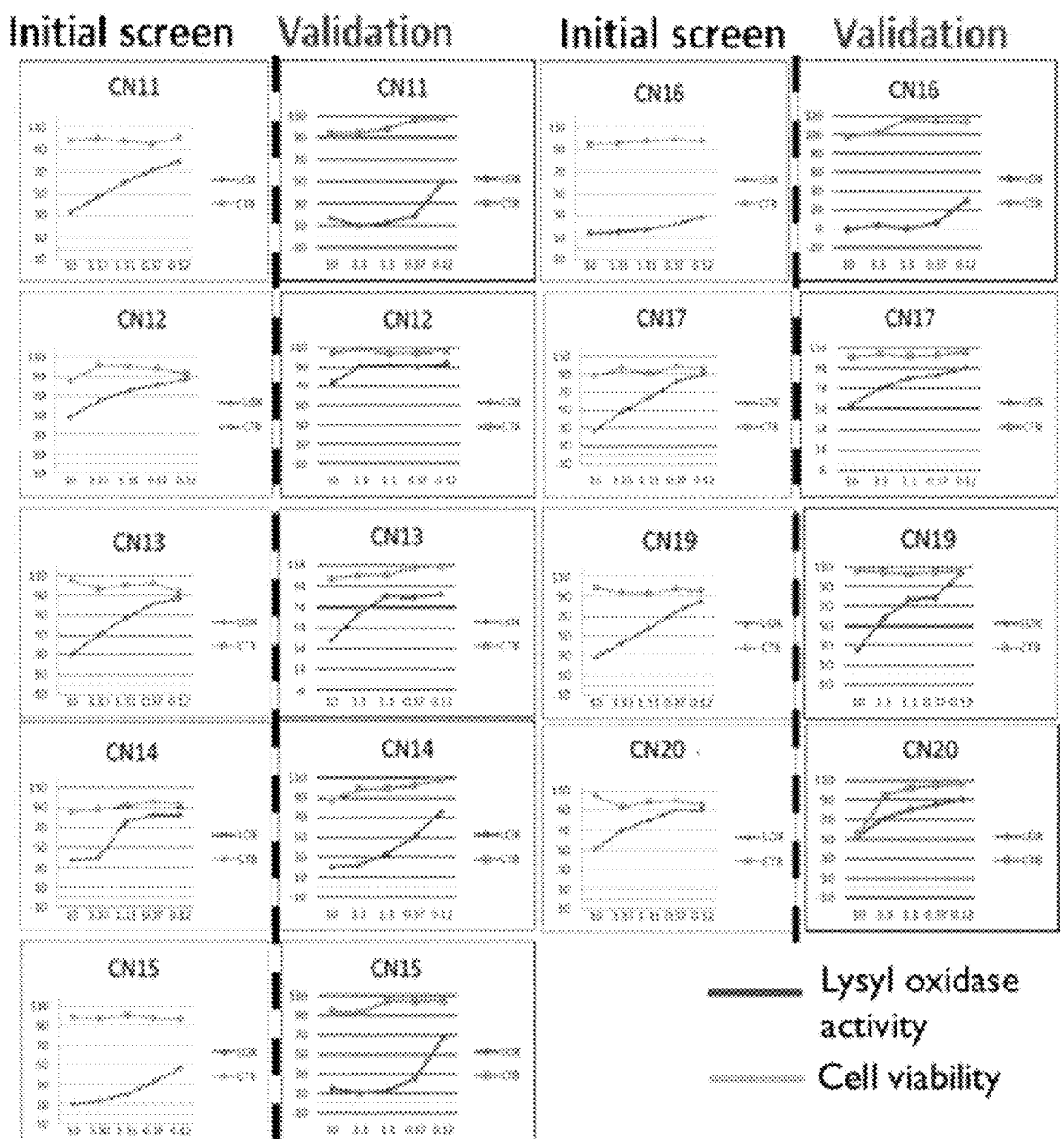
Figure 9:
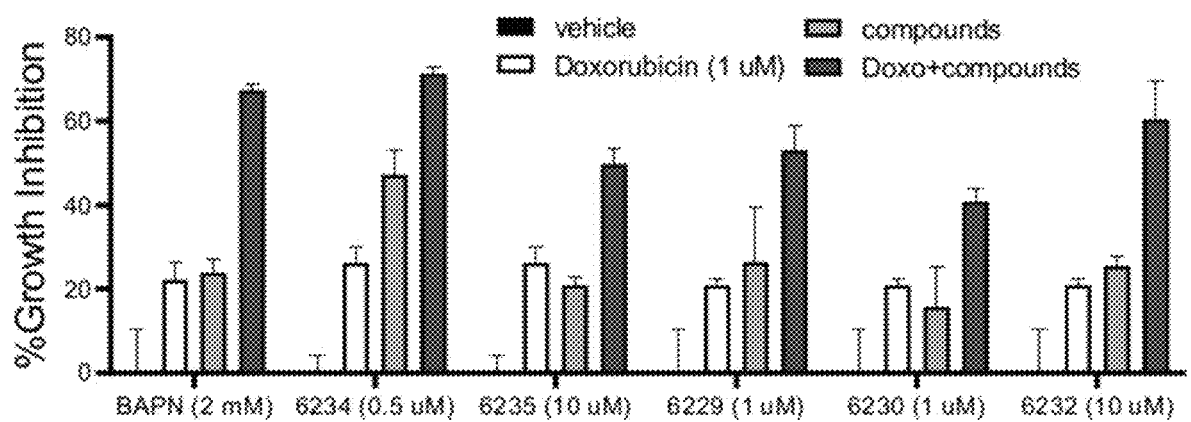
FIG. 9 shows a doxorubicin sensitization screen revealing five target compounds as doxorubicin sensitizers.
Figure 10:
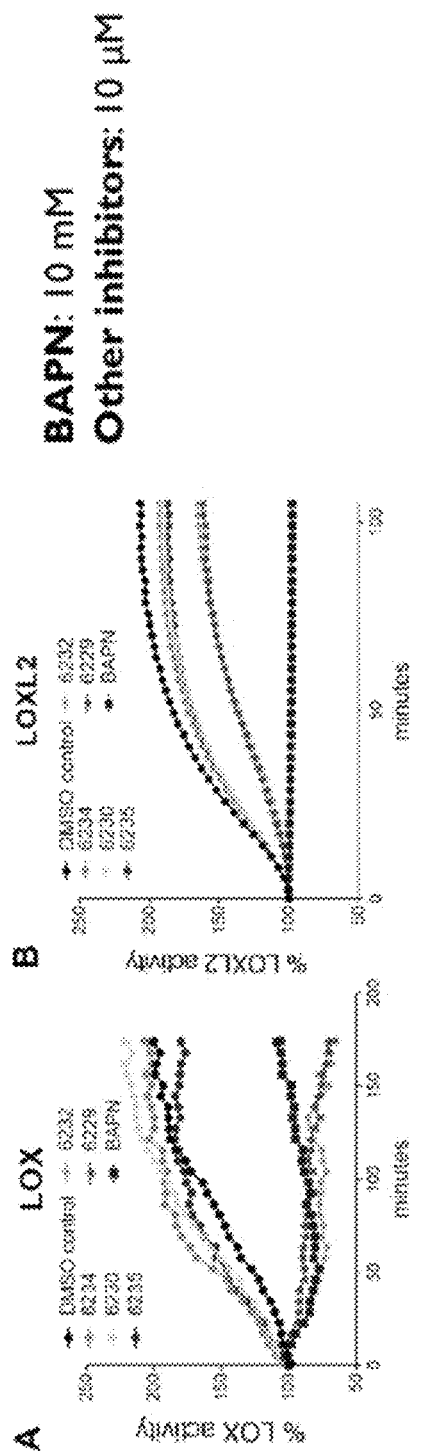
FIG. 10 shows LOX and LOX2 activity for compounds 6232 and 6229.
Figure 11:
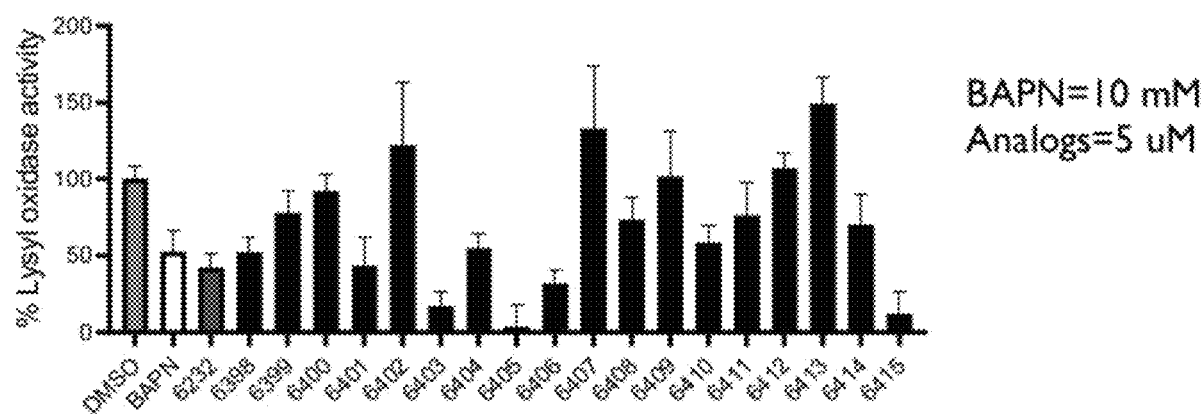
FIG. 11 shows SAR analysis of 6232 indicating further analog compounds.
Figure 12:
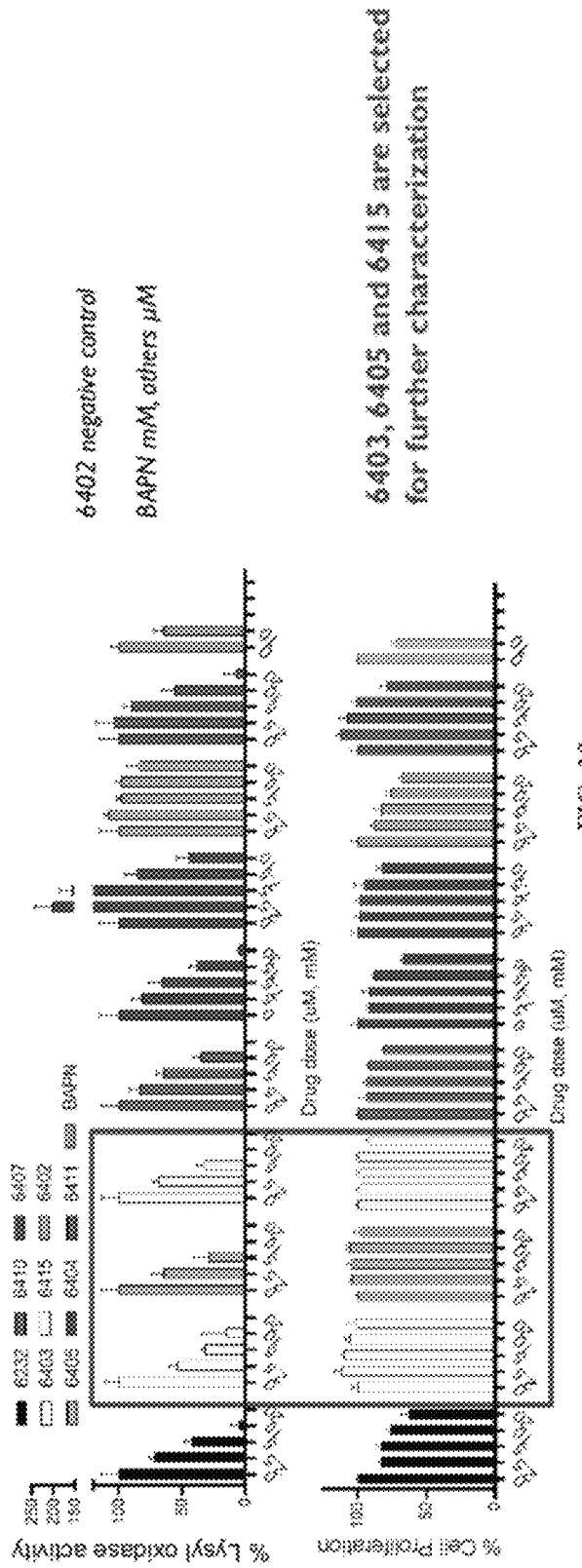
FIG. 12 shows testing of analogs for lysyl oxidase activity and cell proliferation vis-à-vis drug dose.
Figure 14:
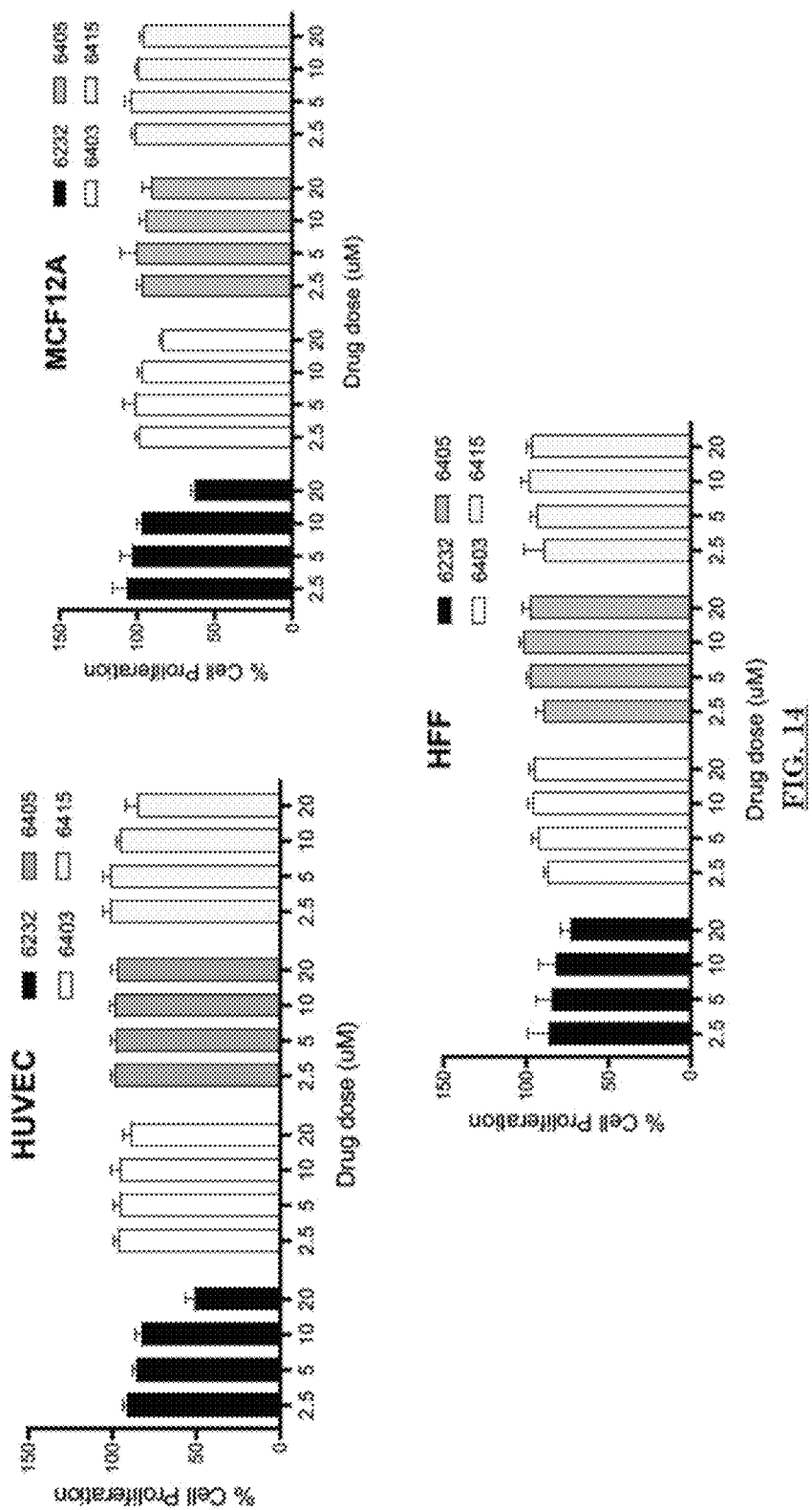
FIG. 14 shows testing of analogs 6403, 6405, and 6425 for toxicity in normal cells.
Figure 15:
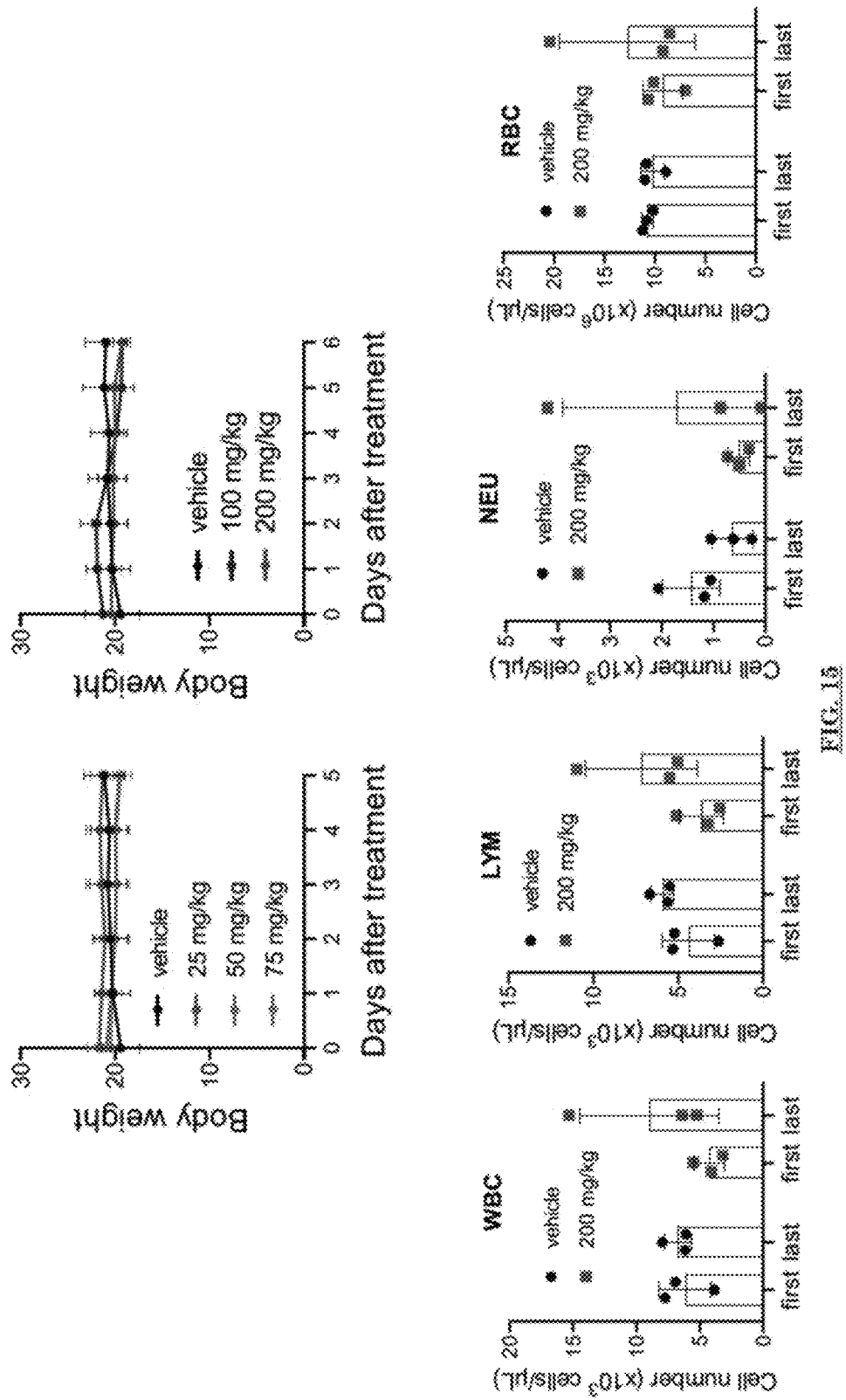
FIG. 15 shows in vivo toxicity testing for compound 6403.
Figure 16:
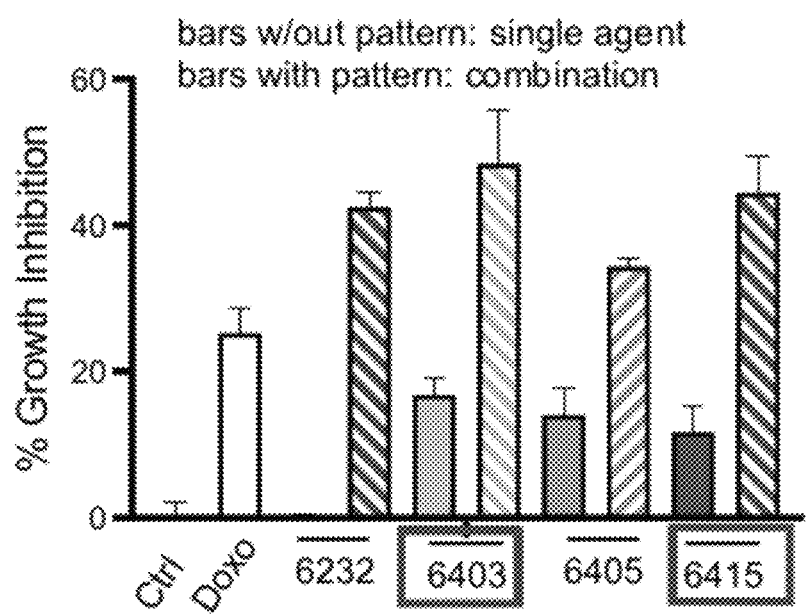
FIG. 16 shows a graphical representation of growth inhibition for compounds 6403 and 6415.
Figure 17:
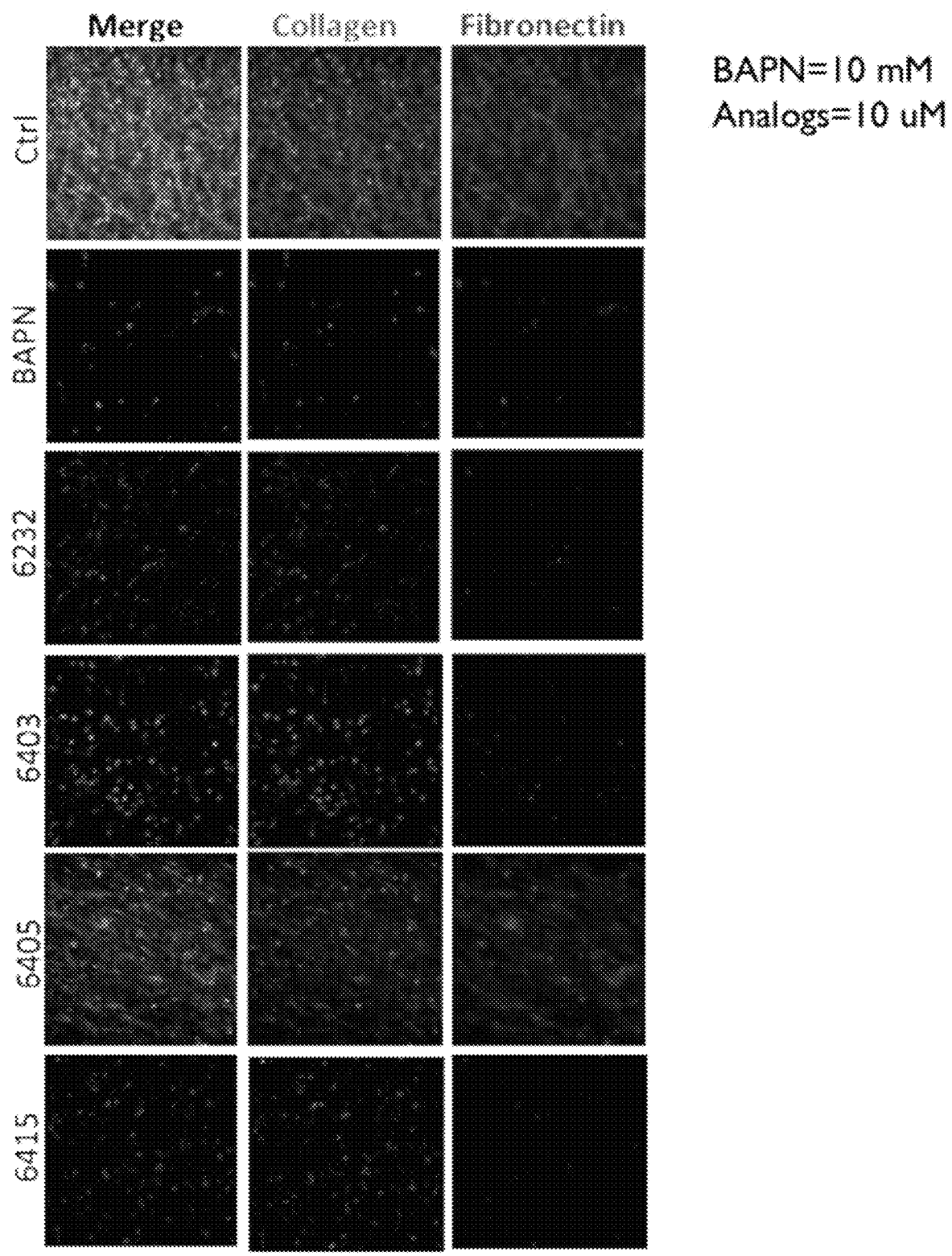
FIG. 17 shows reduced ECM crosslinking via use of compounds 6403 and 5415.
Figure 18:
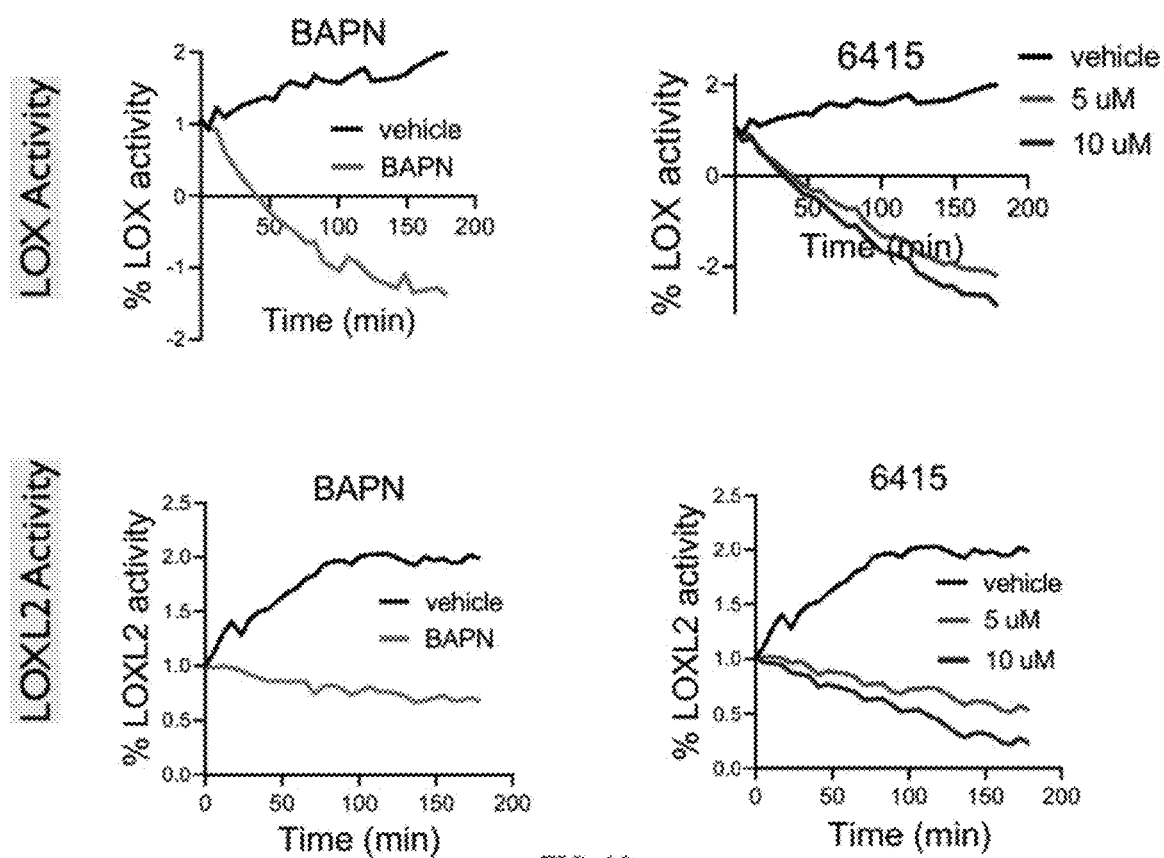
FIG. 18 shows graphs of LOX and LOXL2 activity for compound 6415.

The current disclosure, inter alia, provides methods for identification and characterization of novel LOX/LOXL inhibitors FIG. 5 shows one embodiment of a process for identification and characterization of novel LOX/LOXL inhibitors. Twenty compounds from a library of drug-like molecules and bioactive compounds were identified as potential lysyl oxidase inhibitors that cause no major cellular cytotoxicity. 4,480 small molecules from EXPRESS-Pick diversified library by ChemBridge and a Tocriscreen library of bioactive compounds by Tocris (1,280 compounds). FIG. 6 shows relative lysyl oxidase activity and signal background for potential inhibitors. FIG. 7 shows a comparison of cell viability and lysyl oxidase activity for target compounds. FIG. 8 shows cell viability and lysyl oxidase activity for twenty specific target compounds. Further, nineteen short-listed compounds were freshly obtained, and their effects on cell viability and lysyl oxidase activity were validated. A doxorubicin sensitization screen was performed with the shortlisted nineteen (19) candidates, and five (5) compounds were identified as doxorubicin sensitizers. FIG. 9 shows a doxorubicin sensitization screen revealing five target compounds as doxorubicin sensitizers. Among five (5) candidates, two (2) compounds (6232 and 6229) decreased the activity of both the recombinant LOX and LOXL2 proteins, although LOXL2 inhibition was weaker as compared to BAPN. FIG. 10 shows LOX and LOX2 activity for compounds 6232 and 6229. SAR analyses with 6232 led to several analogs: lysyl oxidase activity inhibition in cell-based assay. FIG. 11 shows SAR analysis of 6232 indicating further analog compounds. Six (6) of the promising analogs were further tested at multiple doses. FIG. 12 shows testing of analogs for lysyl oxidase activity and cell proliferation vis-à-vis drug dose. FIG. 13 shows Table 1, Structure-Activity Relationship of 4'-methyl-N2-phenyl-[4,5'-bithiazole]-2,2'-diamine Lox Inhibitors. Shortlisted analogs (6403, 6405 and 6425) were tested in terms of toxicity in normal cells. FIG. 14 shows testing of analogs 6403, 6405, and 6425 for toxicity in normal cells. No significant effect on the viability of three different normal cell lines. FIG. 15 shows in vivo toxicity testing for compound 6403. FIG. 16 shows a graphical representation of growth inhibition for compounds 6403 and 6415. No major change in body weight or blood cell count were observed even at higher doses. FIG. 17 shows reduced ECM crosslinking via use of compounds 6403 and 5415. FIG. 18 shows graphs of LOX and LOXL2 activity for compound 6415.

Figure 19:
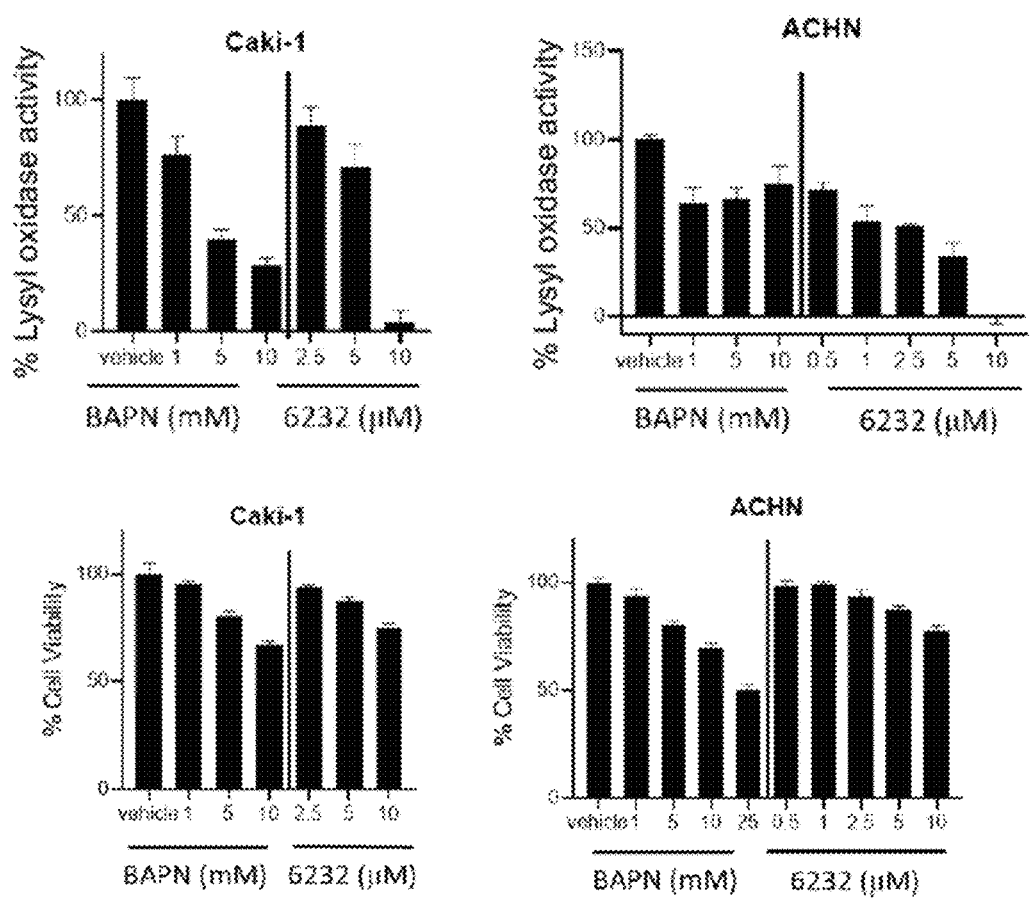
FIG. 19 shows graphical analysis of cell-based lysyl oxidase activity and cell viability assays in Caki-1 and ACHN cell lines treated with increasing doses of BAPN and 6232.
Figure 20:
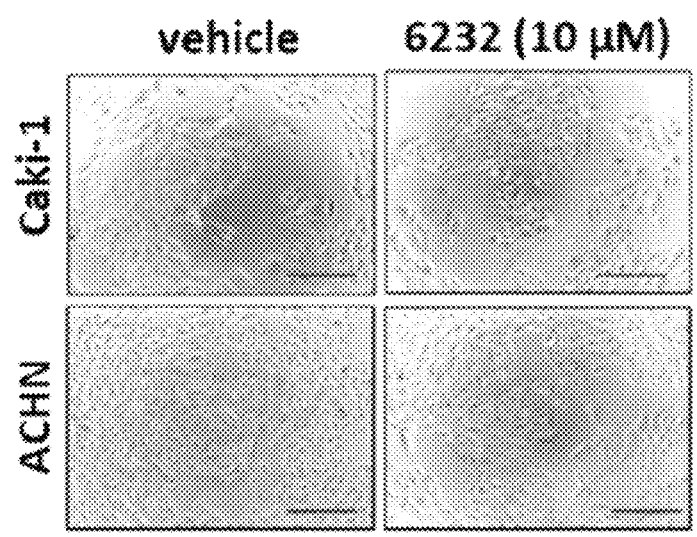
FIG. 20 shows effects of ECM crosslinking in ACHN and Caki-1 cell lines when treated with compound 6232.
Figure 21:
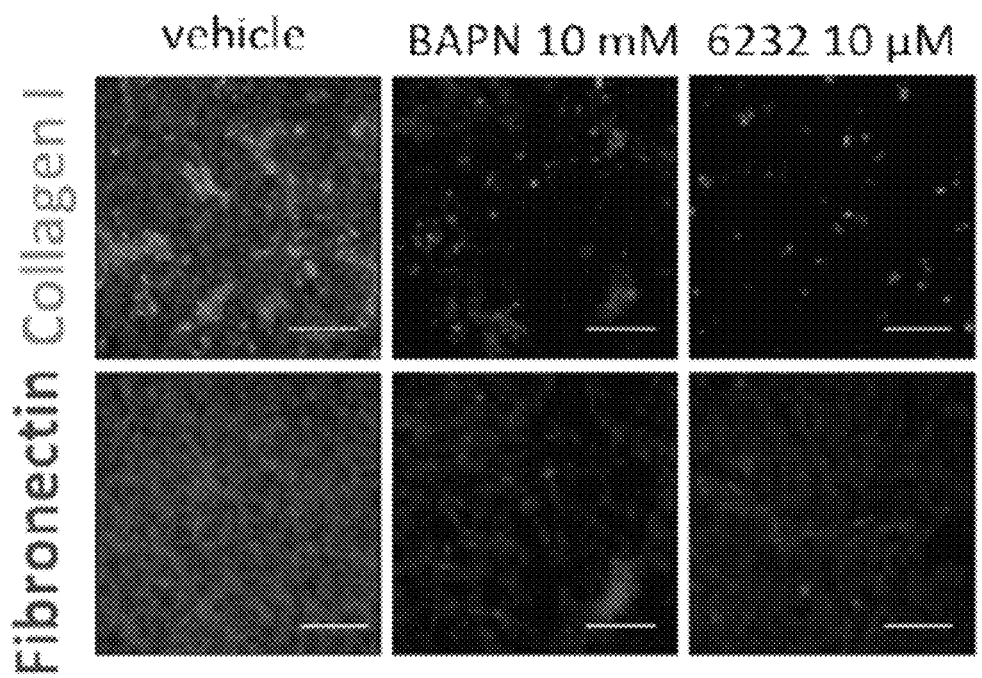
FIG. 21 shows decrease in ECM crosslinking upon treatment with compound 6232.

The inhibitory effect of our parental compound, 6232 has also been tested in ccRCCs having pseudo-hypoxia (i.e., constitutive activation of HIF1α and HIF2α independent of the oxygen level). Cell-based lysyl oxidase activity and cell viability assays in Caki-1 and ACHN cell lines treated with increasing doses of BAPN and 6232. FIG. 19 shows graphical analysis of cell-based lysyl oxidase activity and cell viability assays in Caki-1 and ACHN cell lines treated with increasing doses of BAPN and 6232. FIG. 20 shows effects of ECM crosslinking in ACHN and Caki-1 cell lines when treated with compound 6232. FIG. 21 shows decrease in ECM crosslinking upon treatment with compound 6232.

As the available LOX inhibitors are either not very potent or have toxicity issues, the inventors developed a robust screening pipeline to identify potent and safe LOX-specific and pan-LOX inhibitors. A high-throughput cell-based LOX activity (Abcam) screen was done for more than 5,000 drug-like compounds. The toxic molecules were counter screened with cell cytotoxicity assay and filtered out. Among the most potent hits (20 in total), 5 of them were shortlisted based on their ability to sensitize TNBC cells to doxorubicin, to cross-link collagen-I and tested in recombinant LOX and LOXL2 protein-based activity assays to determine their on-target activity and selectivity. One of the compounds (6232 (phenylbisthiazole diamine core structure)) was selected for SAR and lead optimization studies based on favorable chemistry towards drug-likeness, synthetic feasibility and potential for creating novel and chemically distinct LOX inhibitors. After the SAR analysis, several analogs showed similar or increased activity relative to 6232 and both 6403 and 6415, derivatives of 6232, led to doxorubicin sensitization. Lysyl oxidase activity assay with recombinant proteins revealed that 6403, a derivative of 6232 (NO2 replaced with acetamide), is a more potent and selective inhibitor against LOX compared to LOXL2, while 6415 is more like a LOX/LOXL2 dual inhibitor. Importantly, 6403 showed more potent cellular lysyl oxidase inhibition (IC50=1.3 uM for LOX inhibition) when compared to BAPN (IC50>100 uM). 6403, showed favorable pharmacokinetic (PK) properties in mice and did not lead to any observable organ damage. As a single agent, the inventors tested our LOX inhibitors on kidney cancer in vivo xenograft models. 6403 successfully reduced the tumor growth of LOX-expressing ACHN xenografts without impacting body weight. Finally, the inventors tested the chemosensitizer effect of 6403 in a syngeneic TNBC murine tumor model, 4T1 which has an intact immune system. Combination of 6403 with doxorubicin significantly reduced tumor growth in this LOX-expressing model compared to 6403 and doxorubicin alone groups with no significant change in body weights and blood counts after 21-day treatment. Overall, the inventors obtained both LOX-specific and broader LOX family inhibitors that are novel and have considerable potential for drug development.

Figure 22:
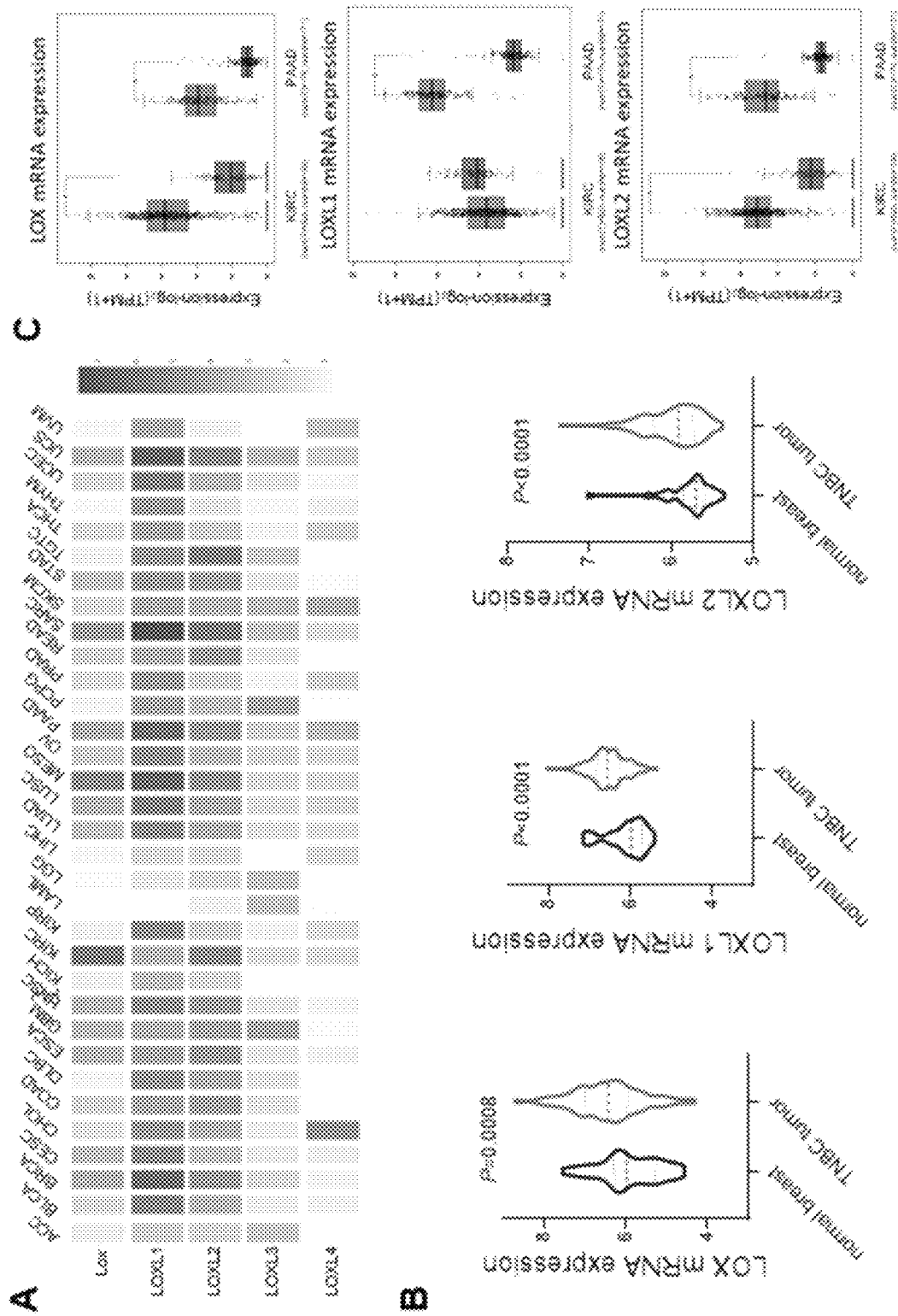
FIG. 22 shows Expression of LOX family members in cancer vs normal tissue by using TCGA dataset.

Among the LOX family members, expression of LOX, LOXL1 and LOXL2 was higher in broad spectrum of cancers compared to normal tissue in The Cancer Genome Atlas (TCGA) dataset, see FIG. 22 at A. LOX, LOXL1 and LOXL2 are highly expressed in TNBCs vs normal breast, see FIG. 22 at B, pancreatic tumors vs. normal tissue and kidney cancer vs. normal tissue, see FIG. 22 at C. These are the tumors known to be stroma-rich and fibrotic.

In the same TCGA dataset, higher expression of LOX, LOXL1 and LOXL2 associates with worse disease-free survival (DFS) in kidney renal cell carcinoma (KIRC). Furthermore, higher expression of LOX and LOXL2 associates with worse relapse-free survival (RFS) in pancreatic adenocarcinoma (PAAD) (in the TCGA dataset) and in chemotherapy-treated breast cancer (KM plotter database), see FIG. 23 at A, B and C. These results suggest that higher expression of LOX family members, especially LOX and LOXL2, is associated with worse disease progression in cancers, especially with stiff tumors.

Figure 24:
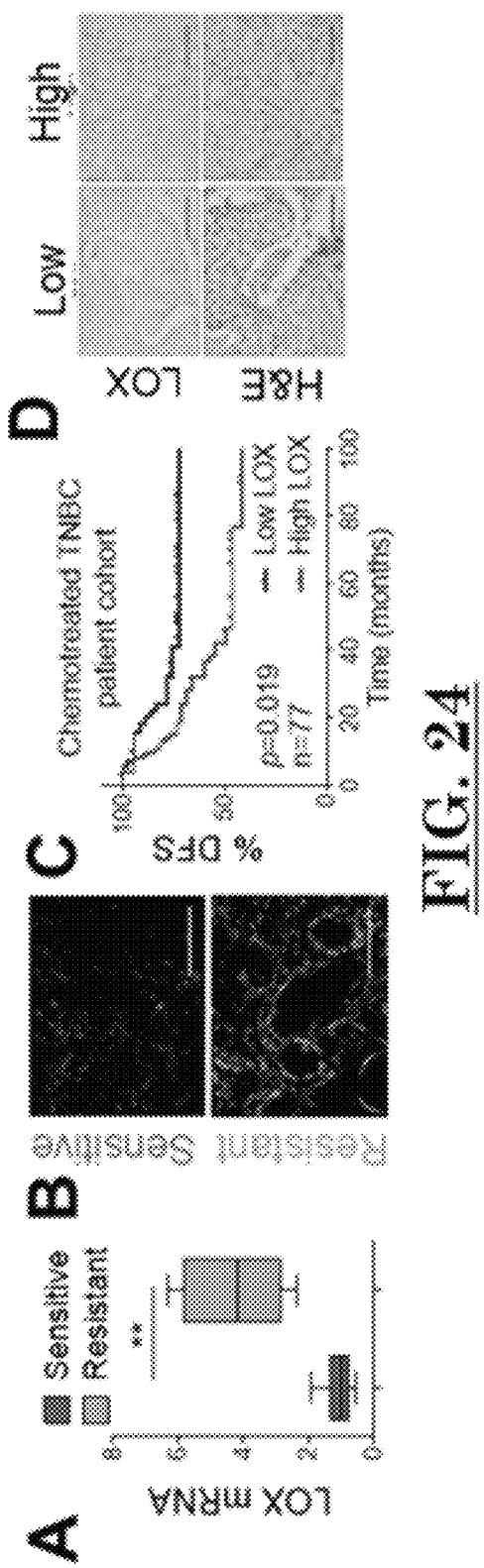
FIG. 24 shows LOX expression is increased in doxorubicin resistance and its high expression is associated with worse survival in chemotherapy treated TNBC patients.

The current inventors identified the hypoxia inducible factor alpha (HIF1α)-induced LOX as being significantly overexpressed, along with increased fibrillar collagen in tumors of our clinically relevant in vivo model of doxorubicin resistance, see FIG. 24 at A and B. the inventors demonstrated that higher LOX mRNA/protein levels are significantly associated with worse disease-free survival (DFS) in chemotherapy treated TNBC patients using multiple published datasets and our own patient cohort, see FIG. 24 at C and D.

The non-specific LOX family inhibitor, BAPN re-sensitized three different collagen I (LOX substrate)-embedded human TNBC cell lines (MDA-MB-231, FIG. 25 at A, MDA-MB-15714 and MDA-MB-43614) to doxorubicin. These results were also recapitulated by specific LOX inhibition upon siRNA-methated knockdown, See FIG. 25 at B. Immunofluorescence (IF) staining of collagen and fibronectin upon incubation of BAPN-treated MDA-MB-231 cells with rat tail collagen I or ECM produced by human foreskin fibroblast (HFF) cells demonstrated reduced ECM deposition and assembly, leading to enhanced drug penetration upon LOX inhibition, See FIG. 25 at C and D. This led to de-activation of downstream FAK/Src signaling, see FIG. 25 at E, and increased apoptosis, see FIG. 25 at F. Importantly, inhibiting FAK or Src kinases recapitulated LOX inhibition-mediated chemosensitization, see FIG. 25 at G.

To test the ability of LOX inhibition to overcome doxorubicin resistance in chemotherapy-refractory TNBC in vivo, the inventors first treated MDA-MB-231 xenografts with doxorubicin until an accelerated tumor growth was achieved. At this point, BAPN (100 mg/kg) was added to half of the doxorubicin-resistant tumors while the rest continued to receive doxorubicin alone (2.5 mg/kg). Strikingly, the addition of LOX inhibitor led to a significant decrease in tumor growth, see FIG. 26 at A, and improved survival. the inventors confirmed the reduction in LOX activity, see FIG. 26 at B, and fibrillar collagen, see FIG. 26 at C.

Figure 27:
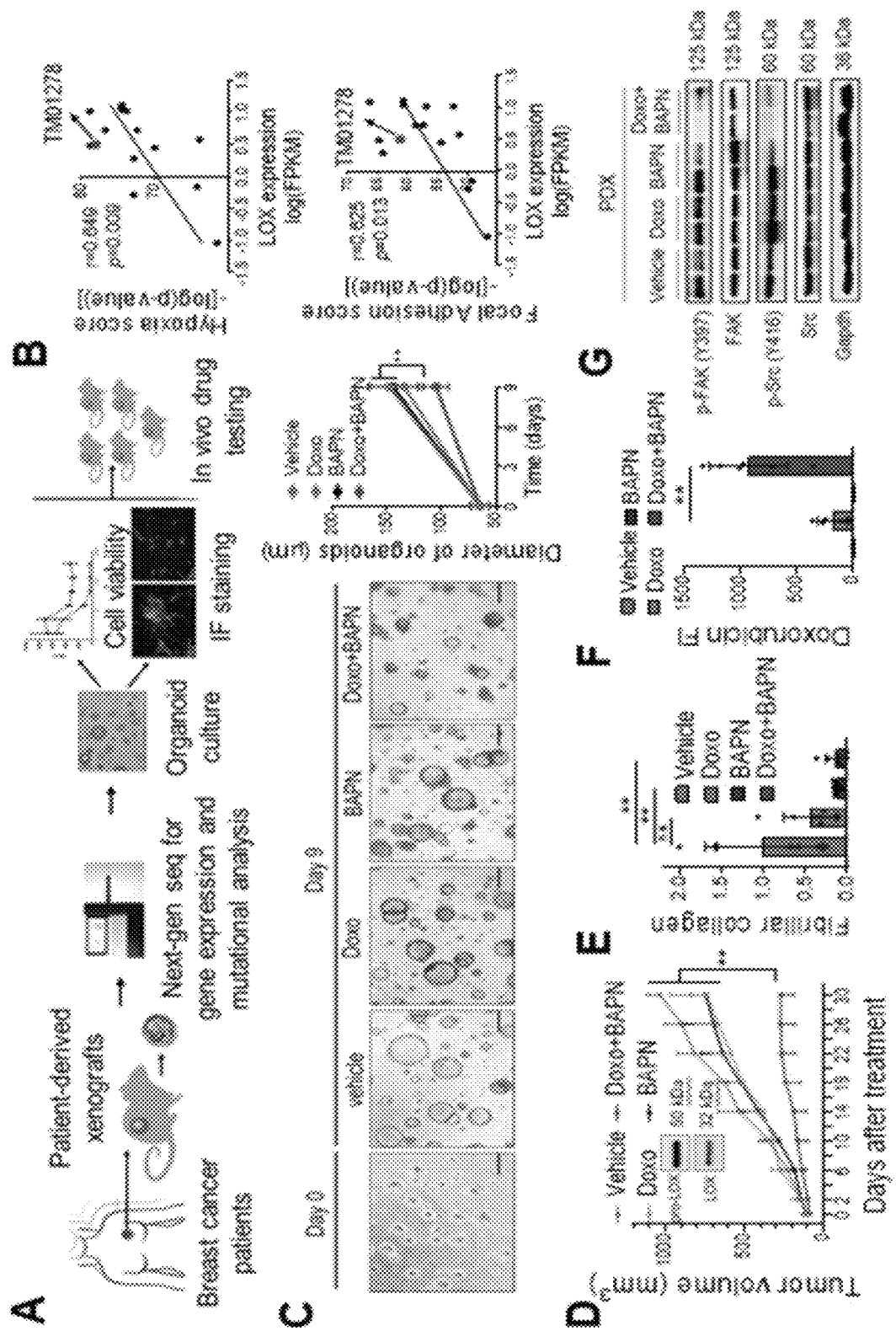
FIG. 27 shows targeting LOX in TNBC PDX organoids or tumors overcomes resistance.

To assess the clinical relevance of targeting LOX, the inventors obtained RNA-Seq data from 15 patient-derived xenograft (PDX) models of TNBC from Jackson Lab along with their drug response data, see FIG. 27 at A, and performed a gene expression-based assessment of hypoxia and focal adhesion (FA) scores for each model and correlated these scores with LOX expression, see FIG. 27 at B. Importantly, expression of LOX had a good correlation (r=0.649 and r=0.625) with both scores. Based on the RNA-Seq analysis and drug response data, the inventors selected one resistant model, TM01278 that is resistant to doxorubicin and expresses high levels of LOX with high hypoxia and focal adhesion scores, Combination of LOX inhibitor with doxorubicin significantly decreased tumor organoid size in 3D organoid culture with collagen I, see FIG. 27 at C, and reduced tumor growth, see FIG. 27 at D. Importantly, LOX activity and fibrillar collagen content were reduced upon LOX inhibition with BAPN, see FIG. 27 at E, which was accompanied by enhanced doxorubicin penetration, see FIG. 27 at F, and reduced FAK/Src signaling, see FIG. 27 at G.

Figure 28:
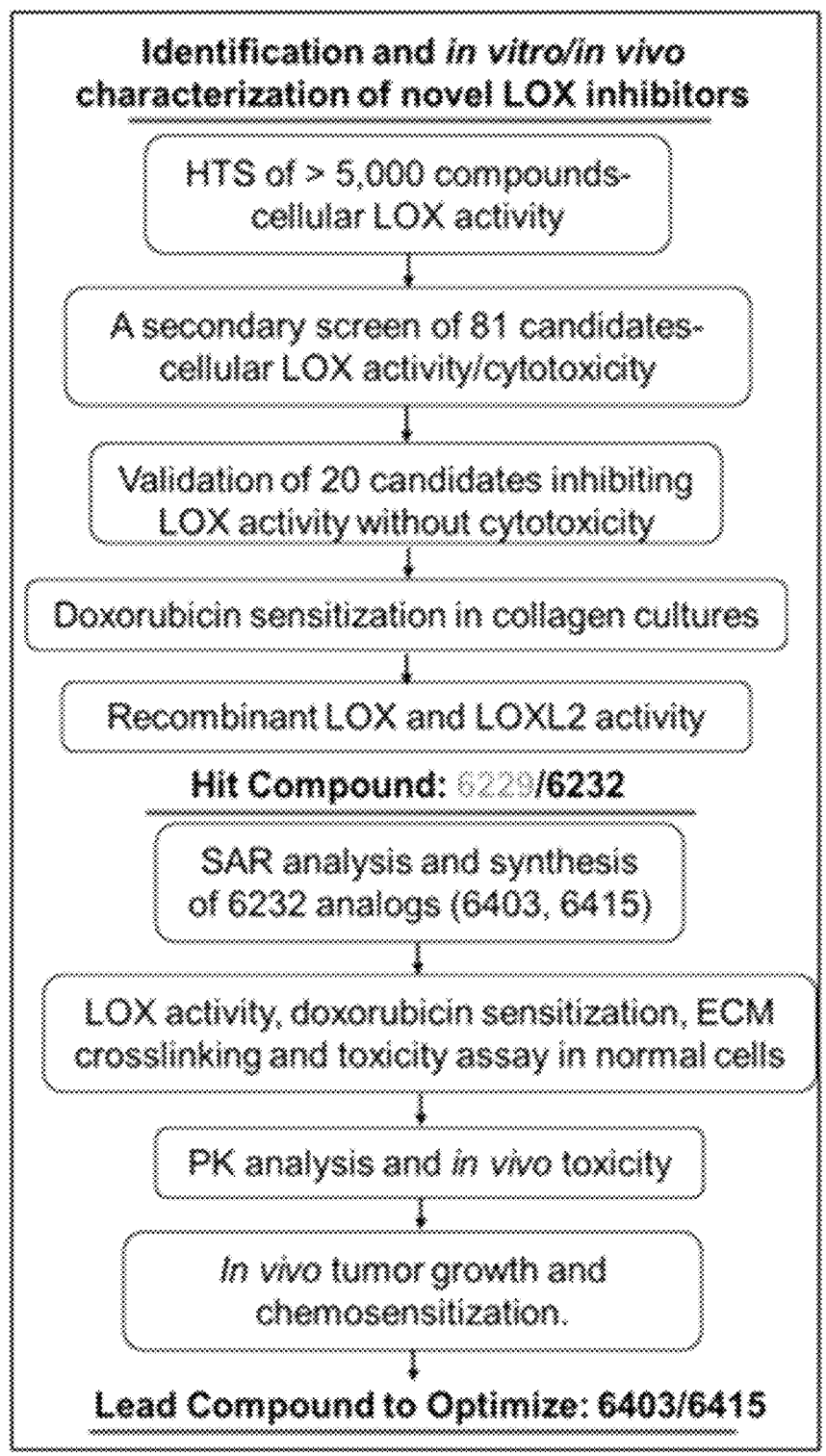
FIG. 28 shows summary of our LOX or LOX family inhibitor discovery pipeline.

As the available LOX inhibitors are either not very potent or have toxicity, the inventors developed a robust screening pipeline shown in FIG. 28 to identify potent and safe LOX-specific and pan-LOX inhibitors. Briefly, a high-throughput cell-based LOX activity (Abcam) screen (HTS) was done for more than 5,000 drug-like compounds from the EXPRESS-Pick diversified library (4,480 molecules, ChemBridge) and Tocriscreen library of bioactive compounds (1,280 compounds, Tocris), each at a single concentration of 10 μM. The screen identified 25 compounds from ChemBridge library and 56 hits from Tocris library that successfully inhibited >90% of LOX activity. The toxic molecules were counter screened with cell cytotoxicity assay and filtered out.

Figure 29:
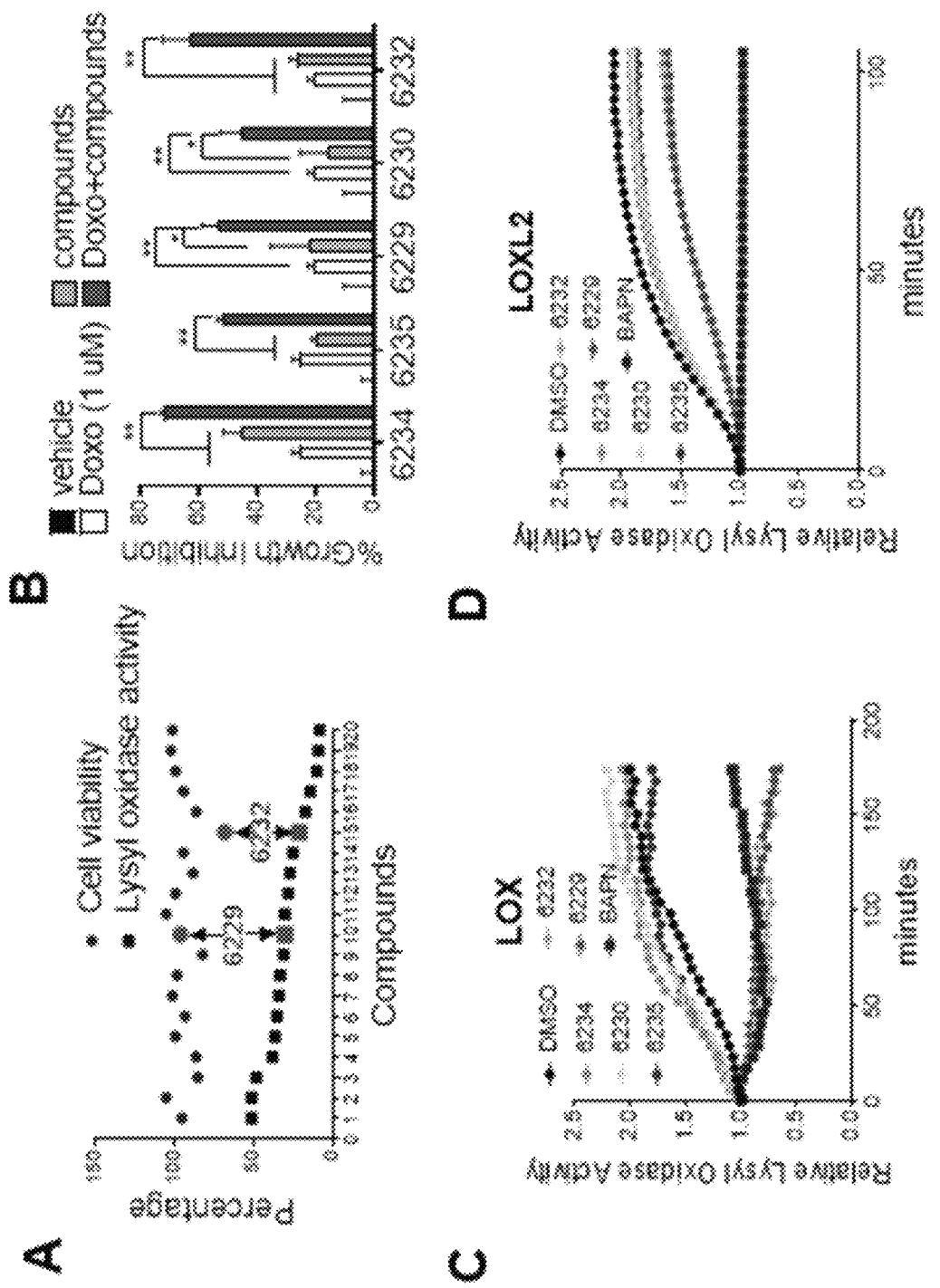
FIG. 29 shows characterization and selection of top hits from the high-throughput screen (HTS) of a diversified small-molecule library to identify novel LOX inhibitors.

The most potent hits (20 in total) were then verified by re-ordering fresh compounds and testing them in the LOX activity and cell viability assays, see FIG. 29 at A. Among these 20 compounds, 5 of them were shortlisted based on their ability to sensitize TNBC cells to doxorubicin, see FIG. 29 at B. These 5 compounds were further tested in recombinant LOX and LOXL2 protein-based activity assays to determine their on-target activity and selectivity. Two compounds (6229 and 6232) were shown to strongly inhibit recombinant LOX, and moderately inhibit LOXL2 at 10 μM, a concentration that is 1000× lower than required for LOX family inhibitor, BAPN, see FIG. 29 at C and D.

A diverse set of analogs of 6232 (phenylbisthiazole diamine core structure, see FIG. 30) were commercially available from ChemBridge and in total 19 compounds were sourced. The inventors found that several analogs possessed similar or increased activity relative to 6232 and provided initial insights into the SAR (see Table 2—FIG. 44, FIG. 30 and FIG. 31 at A). These data pointed to the importance of the free amino group on the terminal thiazole ring and suggested that a variety of substituents could be tolerated on the aniline ring without loss of activity. Of the 19 analogs tested, 6403 and 6415 were the most potent with cellular LOX activity of 1.3 μM and 3.5 μM respectively and therefore these analogs were considered preliminary lead compounds. The inventors also synthesized two new derivatives based on the phenylbisthiazole diamine core structure. Compounds 6425 and 6426 included additional variations of the $R_4$ group (6425 is methoxypropanamide, 6426 is pentamide) and showed high potency with cellular LOX activity of 7.5 μM and 2 μM, respectively. Both 6425 and 6426 are novel compounds and have not been reported in chemical abstracts.

Figure 31:
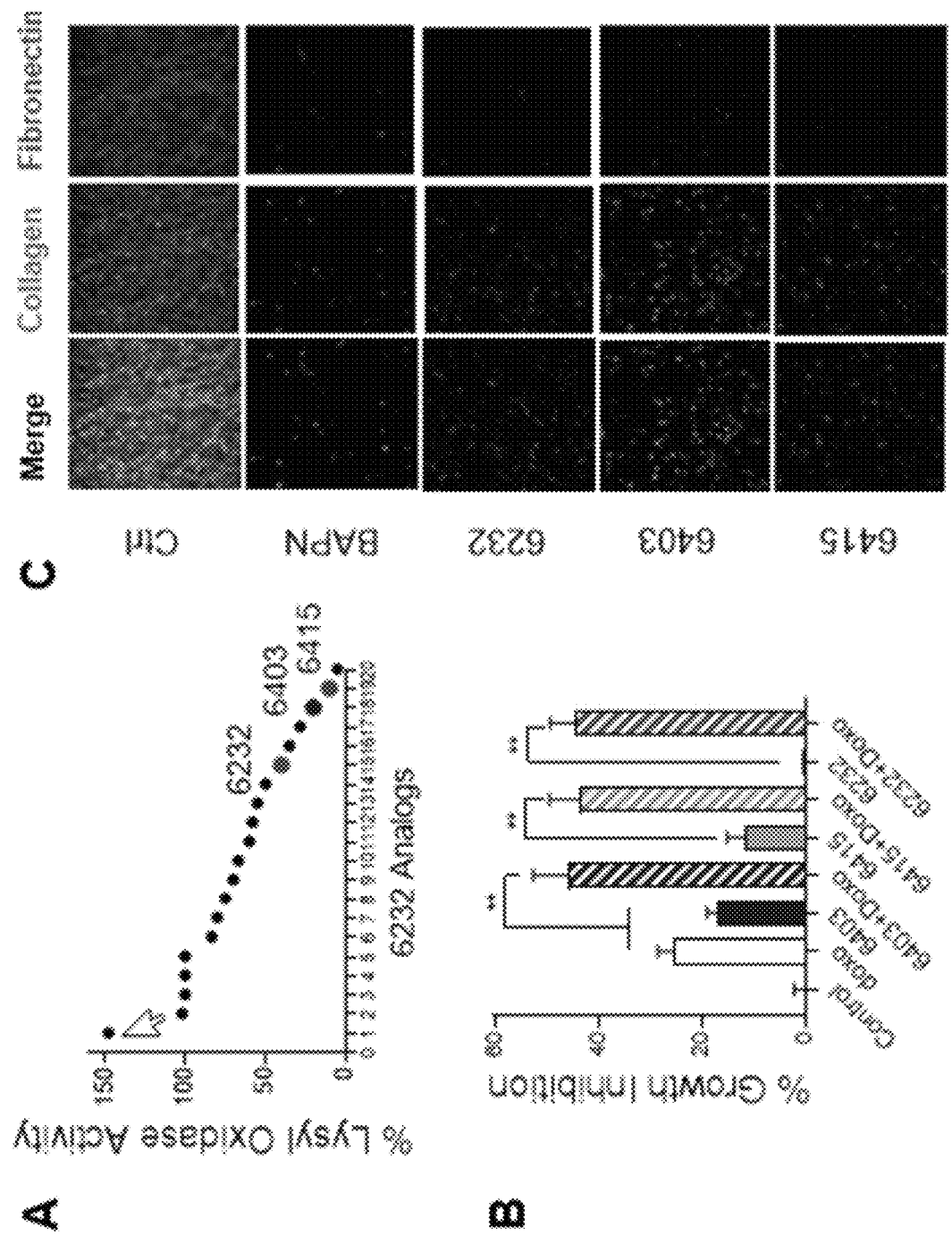
FIG. 31 shows novel 6232 analogs, 6403 and 6415, effectively inhibit lysyl oxidase activity, overcomes doxorubicin resistance and reduce collagen cross-linking and fibronectin assembly.

Treatment with both 6403 and 6415 led to doxorubicin sensitization, FIG. 31 at B, and reduced collagen crosslinking/fibronectin assembly, see FIG. 31 at C. Furthermore, cytotoxicity of 6403 and 6415 was tested on normal cell lines; MCF12A, HUVEC and HFF, see FIG. 32, and no significant change in cell viability was detected.

Figure 33:
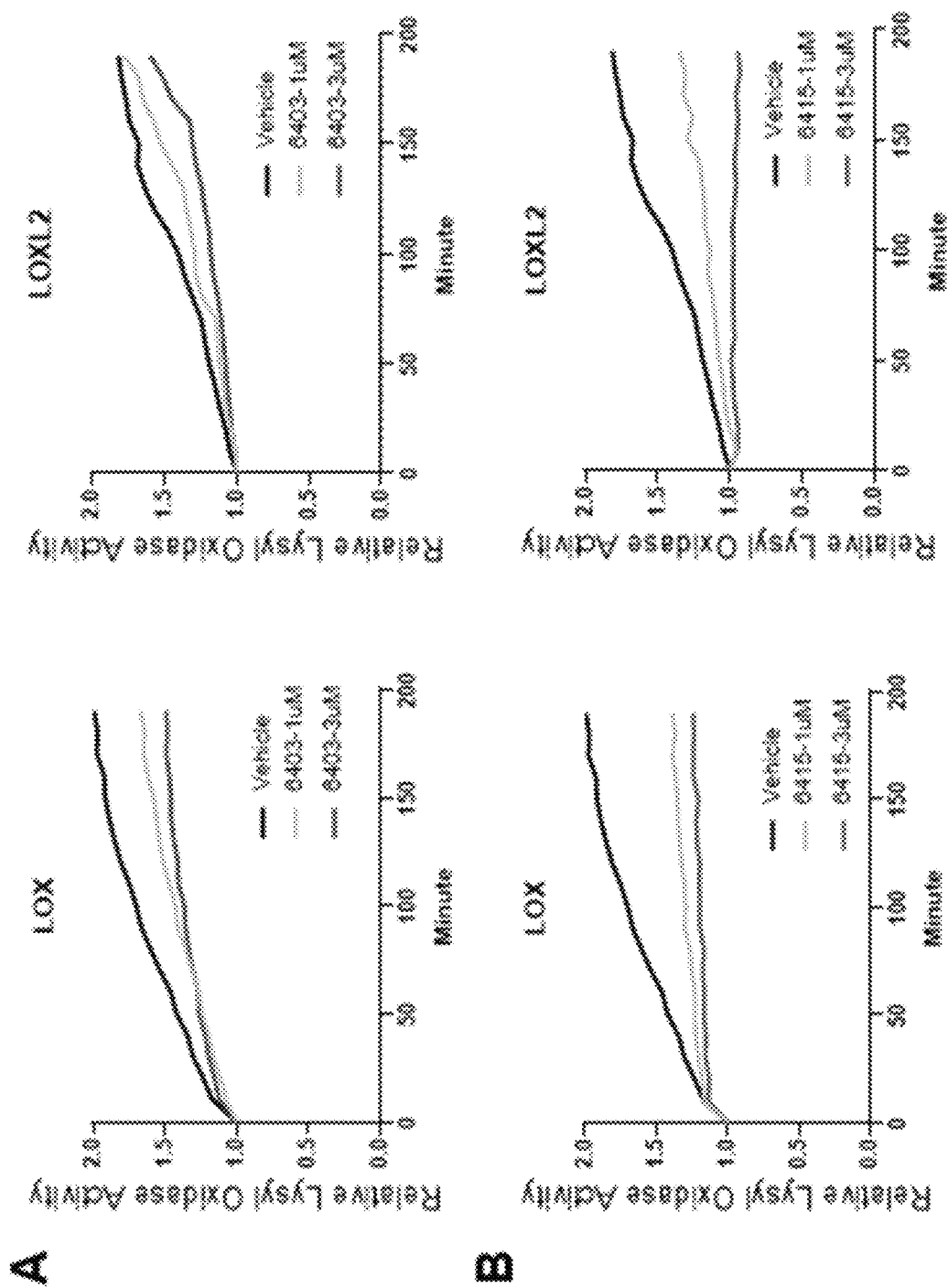
FIG. 33 shows while 6403 inhibits LOX recombinant protein, 6415 inhibits both LOX and LOXL2 recombinant proteins.

Lysyl oxidase activity assay with recombinant proteins revealed that 6403 is a more potent and selective inhibitor against LOX compared to LOXL2, meeting our requirement for LOX specificity, see FIG. 33 at A, while 6415 is more like a LOX/LOXL2 inhibitor, see FIG. 33 at B.

Figure 34:
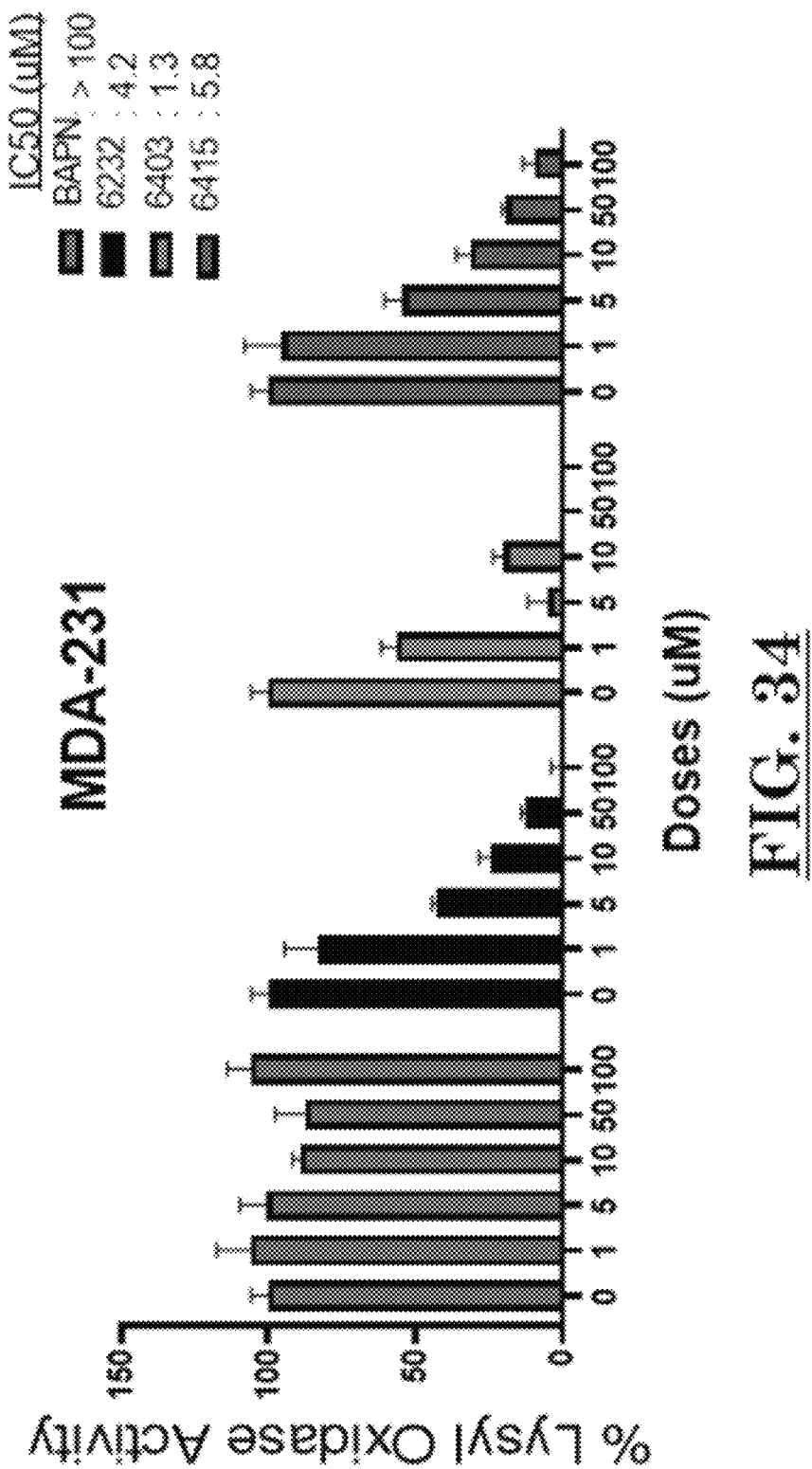
FIG. 34 shows 6232, 6403 and 6415 are more potent than LOX family inhibitor, BAPN.

6232, 6403 and 6415 showed more potent cellular lysyl oxidase inhibition (e.g., IC50=1.3 uM for 6403) when compared to BAPN (IC50>100 uM), see FIG. 34.

Figure 35:
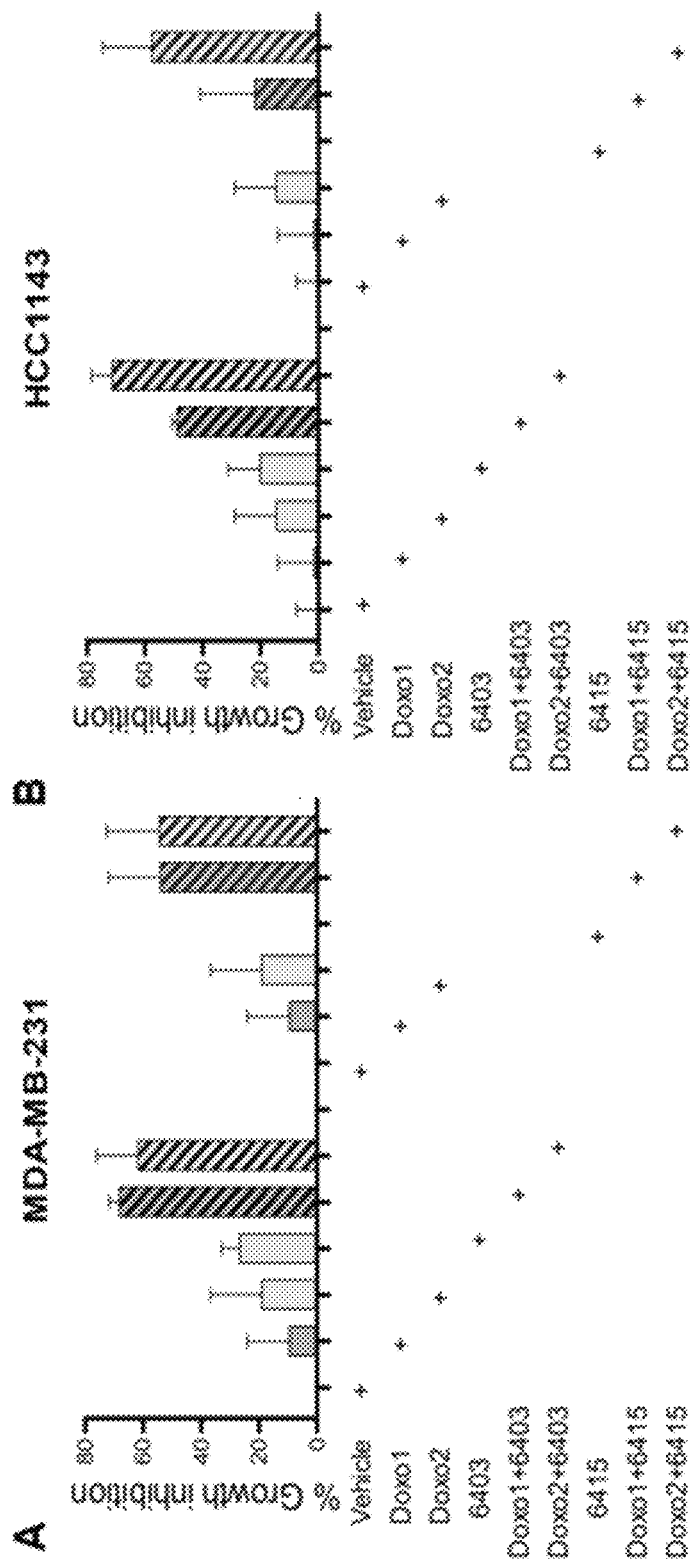
FIG. 35 shows 6403 and 6415 led to doxorubicin chemosensitization in 3D culture of TNBC cell lines.

Treatment with both 6403 and 6415 led to doxorubicin sensitization in collagen I-embedded MDA-MB-231 and HCC1143 TNBC cell lines, see FIG. 35.

Figure 36:
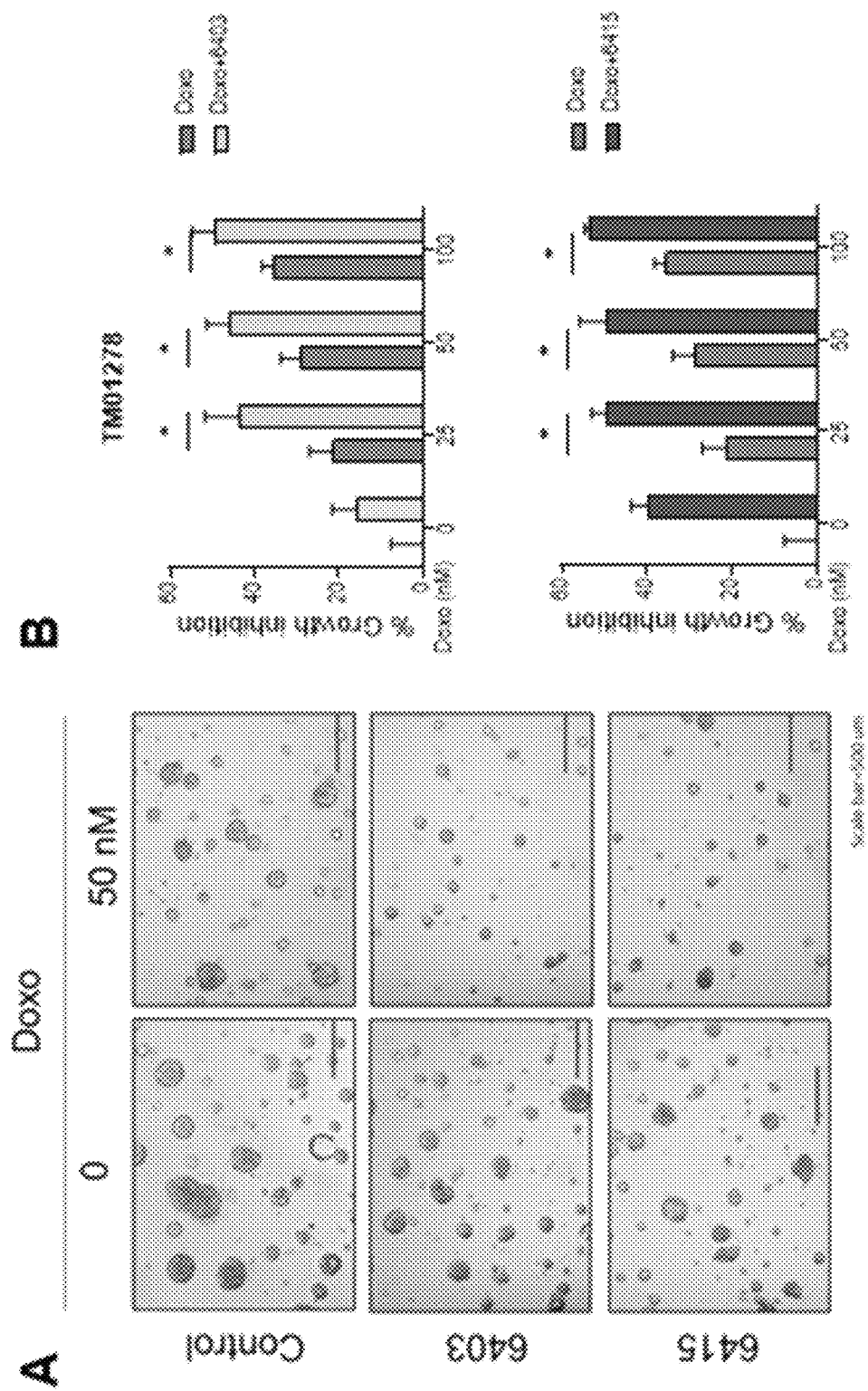
FIG. 36 shows combination of 6403 and 6415 with doxorubicin reduced the growth of the TNBC organoids.

Then, the inventors generated organoid cultures of this doxorubicin-resistant PDX tumors (TM01278) and demonstrated that combination of LOX inhibitors, 6403 and 6415, with doxorubicin significantly decreased organoid size, see FIG. 36 at A, and organoid viability, see FIG. 36 at B, compared to single agent treatments after 9 days of treatment.

The effects of LOX inhibitors, 6232, 6403 and 6415, were tested on cell migration by using RTCA-CIM plate (Roche, USA). All three compounds inhibited the migration capacity of MDA-MB-231 cells, 6403 being the most effective one in this cell line, see FIG. 37.

Previous studies showed that LOX is overexpressed in different cancers and strongly associated with poor outcome in patients with pancreatic, see Miller, B. W. et al. Targeting the LOX/hypoxia axis reverses many of the features that make pancreatic cancer deadly: inhibition of LOX abrogates metastasis and enhances drug efficacy. *EMBO Mol Med* 7, 1063-1076, doi:10.15252/emmm.201404827 (2015). and kidney, see Li, T. et al. Lysyl oxidase family members in urological tumorigenesis and fibrosis. *Oncotarget* 9, 20156-20164, doi:10.18632/oncotarget.24948 (2018), tumors, making it an attractive therapeutic target for these clinically challenging diseases. The inventors observed dose dependent cellular lysyl oxidase activity inhibition, see FIG. 38 at A, and decrease in cell viability in 3D culture, see FIG. 38 at B, upon treatment with 6232, 6403 and 6415 in ACHN kidney cancer cell line, see FIG. 38. In addition to ACHN, treatment with 6232, 6403 and 6415 inhibited cellular LOX activity of another kidney cancer cell line Caki-1 and pancreatic cancer cell lines, Mia-Paca-2 and PANC1, see FIG. 39. Inhibition of LOX activity via our new lead inhibitors will not only be beneficial for TNBC, but also other tumor types characterized by high stiffness and chemoresistance, such as pancreatic cancer, or LOX-driven cancers, such as kidney cancer in future.

The inventors tested the effects of our LOX inhibitors on the TGF-beta induced fibrosis. Immunofluorescence staining of fibrosis markers are substantially reduced upon treatment with LOX inhibitors, see FIG. 40. ALK5 inhibitor was used as a positive control.

Figure 41:
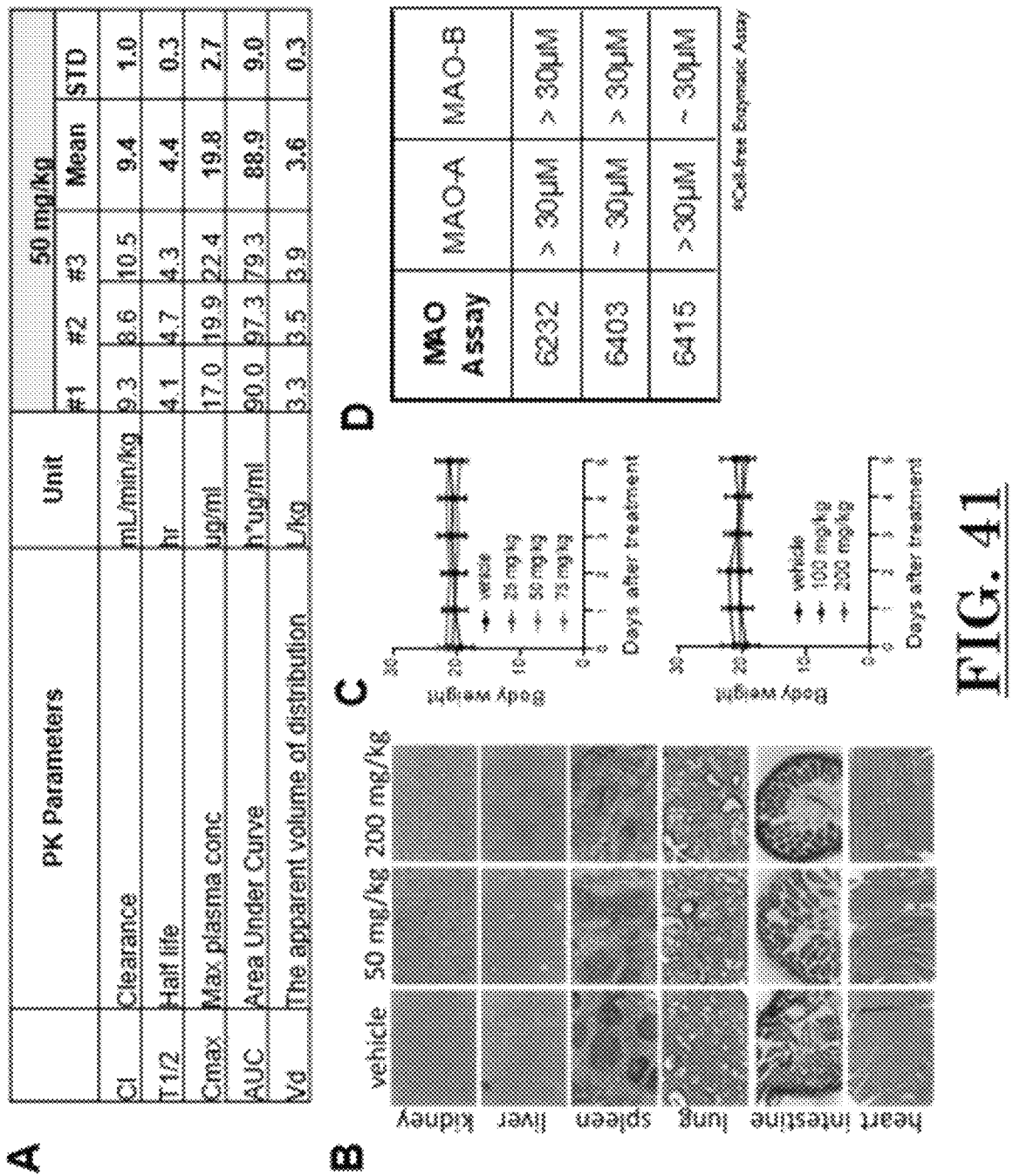
FIG. 41 shows in vivo testing of 6403 with respect to PK and toxicity.

Our lead LOX inhibitor 6403 showed favorable pharmacokinetic (PK) properties in mice, with a high Area Under the Curve (AUC), long half-life (T½), high maximum concentration (Cmax), and volume of distribution (Vd) while having low clearance (Cl), see FIG. 41 at A, and did not lead to any observable organ damage, see FIG. 41 at B or body weight change, see FIG. 41 at C. Importantly, our parental molecule 6232, and its derivatives 6403 and 6415, did not inhibit monoamine oxidase A or B (MAO-A/-B) activity, see FIG. 41 at D, in cell-free enzymatic activity assay, demonstrating its selectivity towards LOX enzymes.

Figure 42:
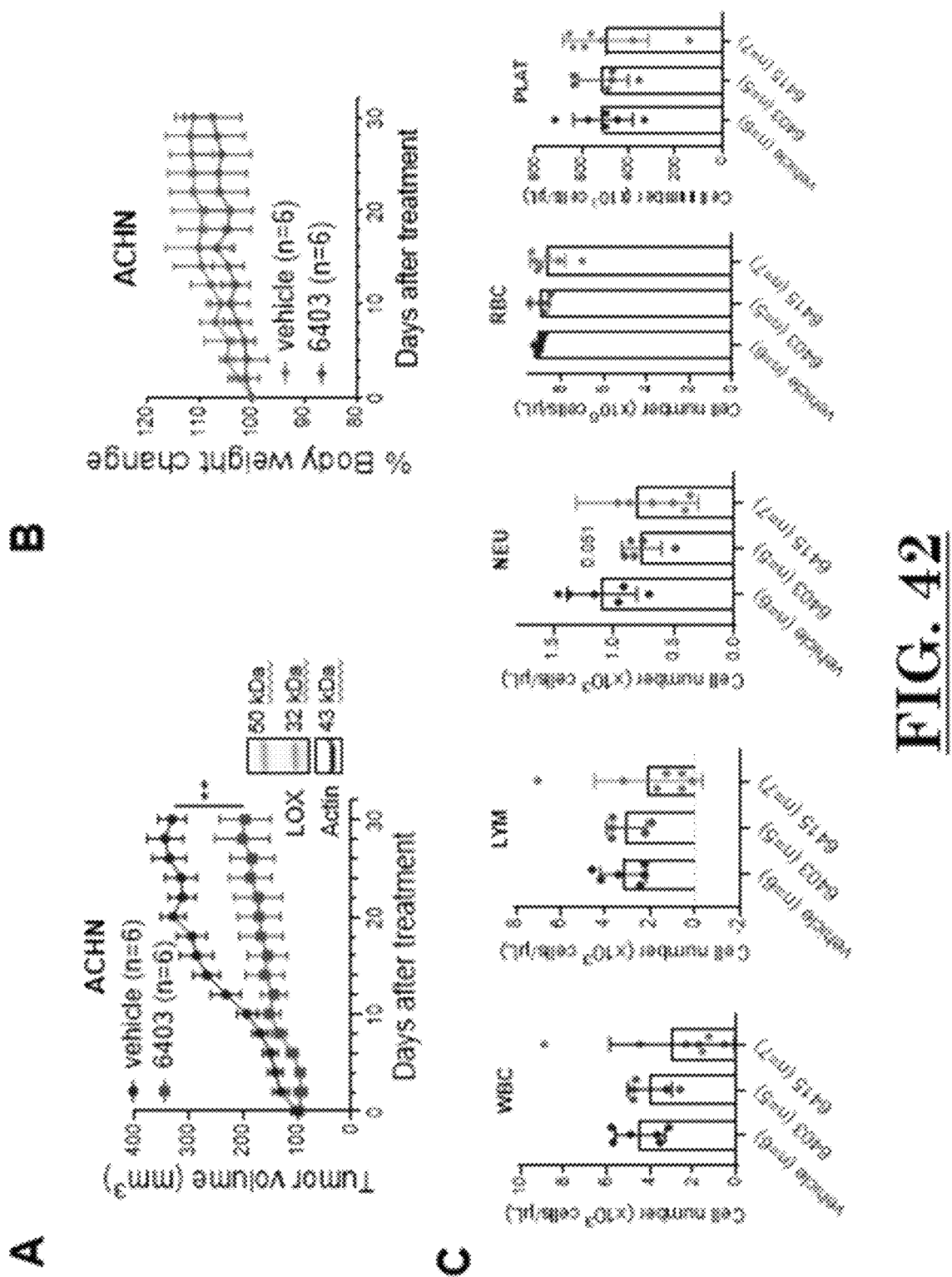
FIG. 42 shows efficacy of 6403 as a single agent in ccRC xenografts.

6403 successfully reduced the tumor growth of LOX-expressing ACHN ccRCC xenografts without impacting body weight and counts of major blood cells, see FIG. 42.

Finally, the inventors tested the chemosensitizing effect of 6403 in a syngeneic TNBC tumor model, 4T1 which has an intact immune system. Combination of 6403 with doxorubicin significantly reduced tumor growth in this LOX-expressing model compared to 6403 and doxorubicin alone groups, see FIG. 43 at A and B, with no significant change in body weights and blood counts after 21-day treatment, see FIG. 43 at C and D.

It has now been found that compounds of this invention, and pharmaceutically acceptable compositions thereof, are effective as inhibitors of LOX or LOX family activity. Such compounds have the general formula I:

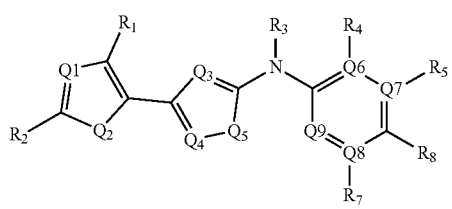

or a pharmaceutically acceptable salt thereof, wherein each variable is as defined and described herein. Compounds of the present invention, and pharmaceutically acceptable compositions thereof, are useful for treating a variety of diseases, disorders, or conditions, associated with LOX activity. Such diseases, disorders, or conditions include those described herein. Compounds provided by this invention are also useful for the study of LOX enzymes in biological and pathological phenomena.

I or a pharmaceutically acceptable salt thereof, wherein:

Q1 is =N— or =CH—

Q2 is NH, O or S

Q3 is =N— or =CH—

Q4 is NH, O or S and Q5 is =N— or =CH—

Q4=N— or =CH— and Q5 is NH, O or S

Q6 is =N— or =CH—R4

Q7 is =N— or =CH—R5

Q8 is =N— or =CH—R6

Q9 is =N— or =CH—R7

R1-R7 is independently halogen, —CN, —$NO_2$, —$NH_2$, —NHR, —$CH_2$R, —OR, —SR, —$NR_2$, —$S(O)_2R$, —$S(O)_2NR_2$, —S(O)R, —C(O)R, —C(O)OR, —$C(O)NR_2$, —C(O)N(R)OR, —N(R)C(O)OR, —N(R)C(O)$NR_2$, or —N(R)S(O)$_2$R;

Where each R is independently hydrogen, or an optionally substituted group selected from C1-6 aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur, see Table 2, FIG. 44.

The chemical structure for 6232 is:

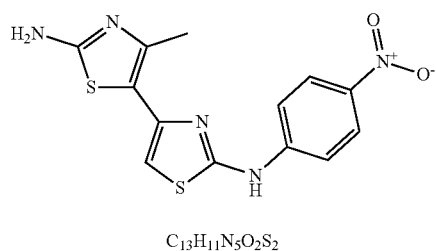 [SMILES: Cc1nc(N)sc1-c1csc(Nc2ccc([N+](=O)[O-])cc2)n1 ; "C13H11N5O2S2"]

$C_{13}H_{11}N_5O_2S_2$

The chemical structure for 6403 is:

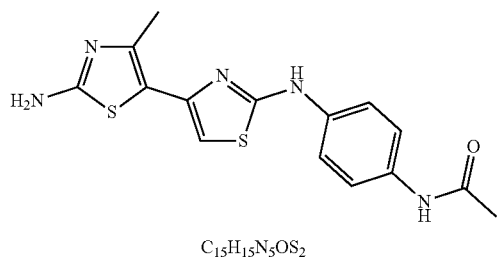 [SMILES: CC(=O)Nc1ccc(Nc2nc(-c3sc(N)nc3C)cs2)cc1 ; "C15H15N5OS2"]

$C_{15}H_{15}N_5OS_2$

The chemical structure for 6405 is:

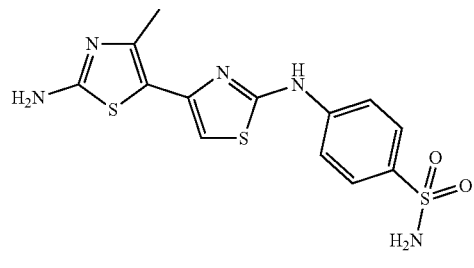

$C_{13}H_{13}N_5O_2S_3$

The chemical structure for 6415 is:

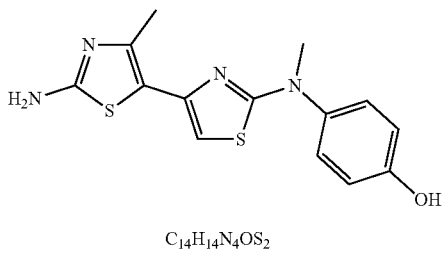 [SMILES: Cc1nc(N)sc1-c1csc(N(C)c2ccc(O)cc2)n1 ; "C14H14N4OS2"]

$C_{14}H_{14}N_4OS_2$

Figure 45:
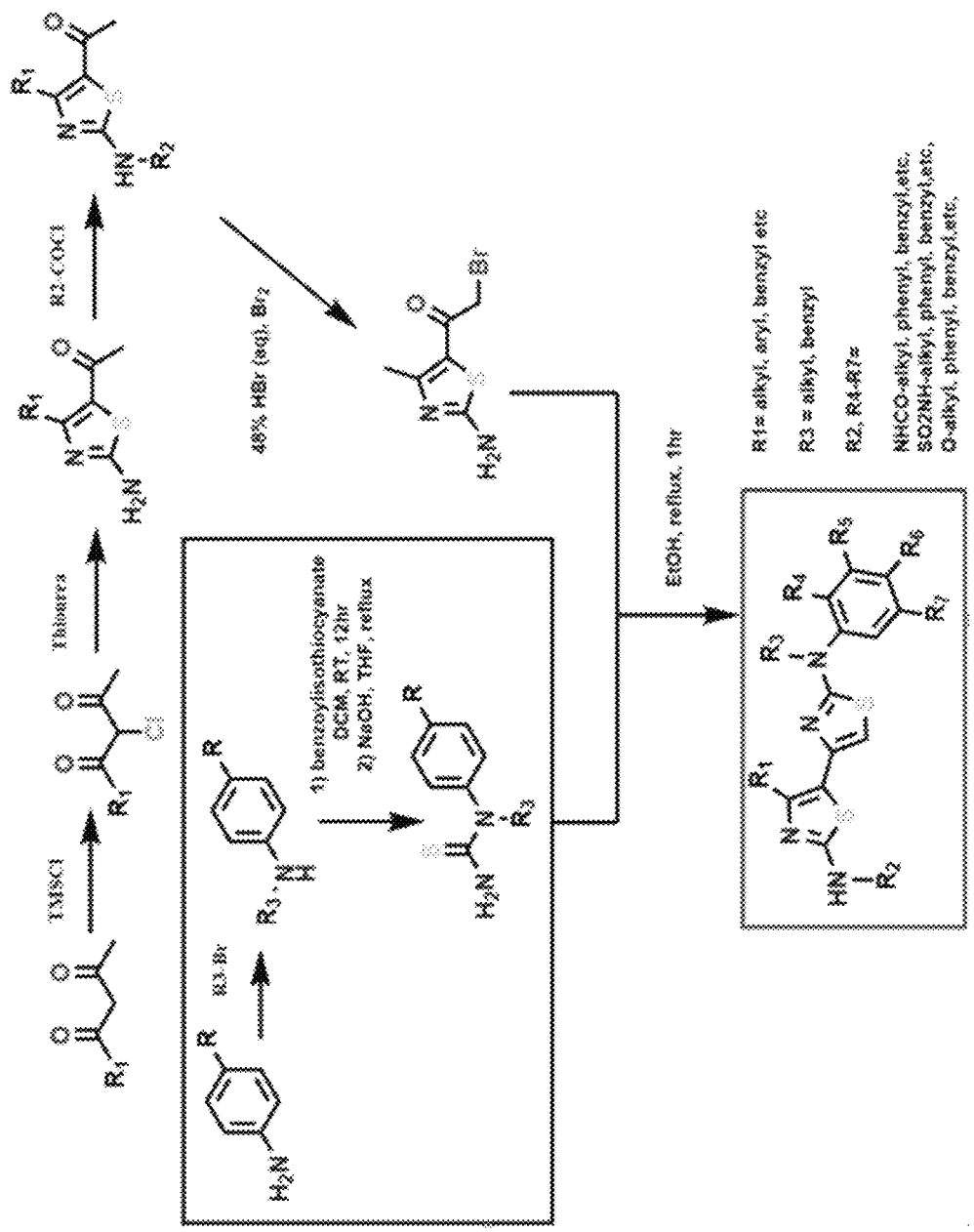
FIG. 45 shows a synthesis scheme for Formula I.
Figure 46:
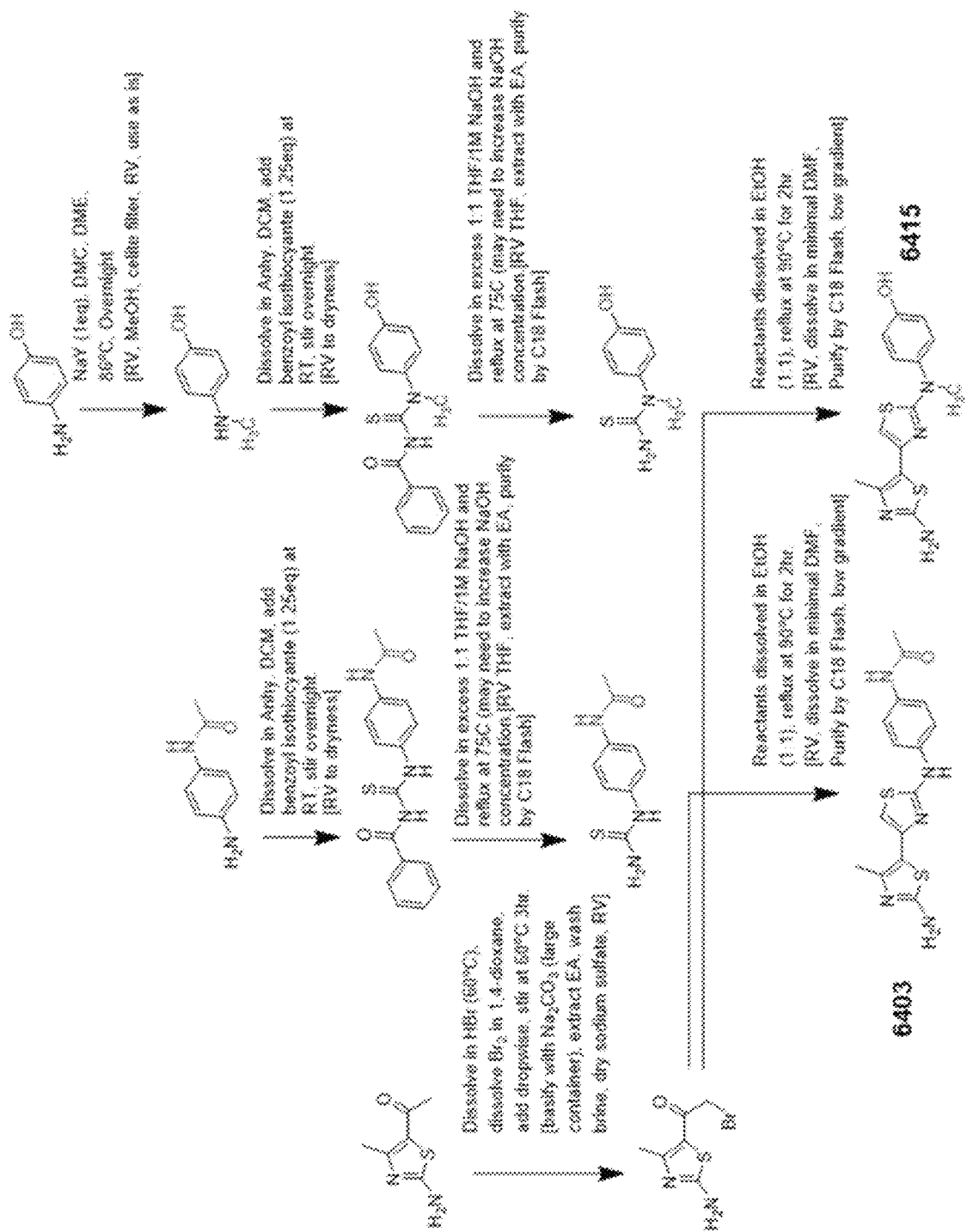
FIG. 46 shows synthesis routes for analogs 6403 and 6415.

FIG. 45 shows a synthesis scheme for Formula I. FIG. 46 shows synthesis routes for analogs 6403 and 6415.

Figure Legends

FIG. 1 shows a diagram of extracellular matrix remodeling (Hung-Yu Lin et al, 2020, *International Journal of Molecular Sciences*).

Figure 2:
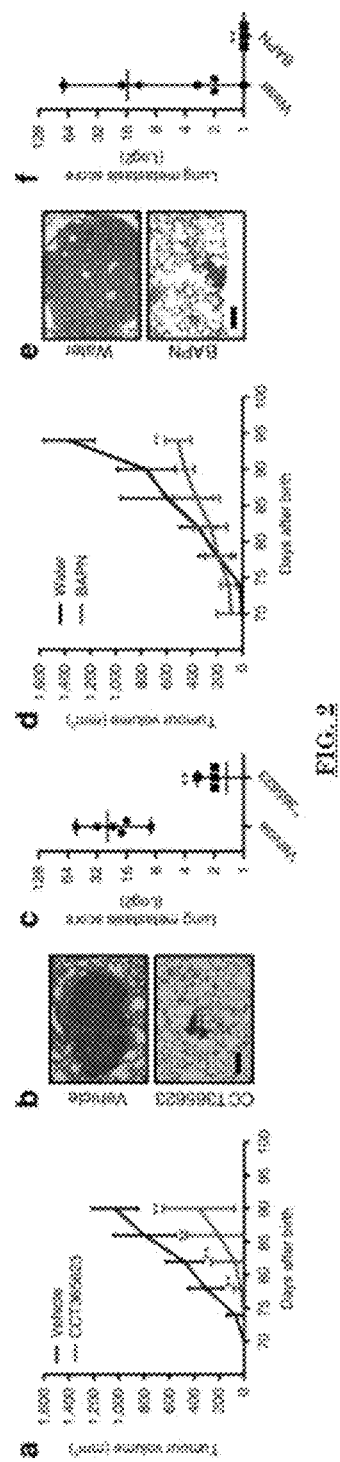
FIG. 2 shows graphical and visual analysis of tumor cell growth after birth and metastasis data resulting from treatment with CCT365623.

FIG. 2 shows graphical and visual analysis of tumor cell growth after birth and metastasis data resulting from treatment with CCT365623 (Tang, HaoRan, et al., 2017, *Nature Communications*). Treatment with CCT365623, daily by oral gavage with 70 mg/kg dose decreased tumor growth and reduced metastasis in breast cancer models.

Figure 3:
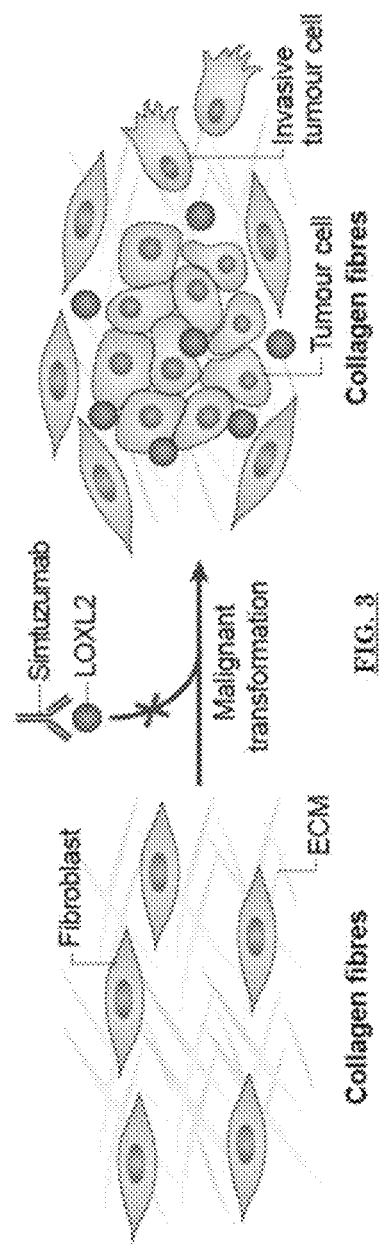
FIG. 3 shows an illustration of interaction between LOXL2, tumor cells and collagen fibers.

FIG. 3 shows an illustration of interaction between LOXL2, tumor cells and collagen fibers (Ferreira, Sandra, et al., 2021, *Antioxidants*).

FIG. 4 shows the molecular structure of PXS-5153A (Schiller H et al, 2018, *J. Cell. Mol. Med*).

FIG. 5 shows one embodiment of a process for identification and characterization of novel LOX/LOXL inhibitors.

FIG. 6 shows the preliminary testing of LOX activity assay for compound screen. Left panel shows the relative lysyl oxidase activity and right panel shows signal-to-background ratio for the general LOX inhibitor, BAPN.

FIG. 7 shows a comparison of percentage cell viability and lysyl oxidase activity for target compounds using MDA-MB-231 cells. 20 compounds from a library of drug-like molecules and bioactive compounds were identified as potential lysyl oxidase inhibitors that cause no major cellular cytotoxicity.

FIG. 8 shows the validation of the effects of 19 short-listed compounds that were freshly obtained on cell viability and lysyl oxidase activity.

FIG. 9 shows a doxorubicin sensitization screen revealing five target compounds as doxorubicin sensitizers. BAPN is used as a positive control.

FIG. 10 shows the effects of 5 compounds on LOX and LOL2 activity. Among 5 candidates, 2 compounds (6232 and 6229) decreased the activity of both the recombinant LOX (A) and LOXL2 (B) proteins, although LOXL2 inhibition was weaker as compared to BAPN.

FIG. 11 shows the effect of 18 different 6232 analogs identified by SAR analysis on lysyl oxidase activity. The analogs were used at a concentration of 5 µM, whereas BAPN was used at 10 mM.

FIG. 12 shows the effects of the short-listed analogs on lysyl oxidase activity and cell proliferation at multiple doses (2.5, 5, 10 and 20 uM). BAPN was used at 10 mM concentration.

FIG. 13 shows Table 1, Structure-Activity Relationship of 4'-methyl-N2-phenyl-[4,5'-bithiazole]-2,2'-diamine Lox Inhibitors.

FIG. 14 shows testing of the shortlisted analogs 6403, 6405, and 6415 for toxicity in normal HUVEC, MCF12A and HFF cells. No significant effect on the viability of normal cell lines was detected.

FIG. 15 shows in vivo toxicity testing for compound 6403. The upper panel shows the body weight of the mice treated with different doses of 6403, administered daily. The lower panel shows the blood cell counts from the vehicle vs. 200 mg/kg 6403-treated mice. No significant effect on body weight and blood counts were detected.

FIG. 16 shows the percentage growth inhibition in the TNBC cell line, MDA-MB-231, embedded in collagen and treated with the combination of doxorubicin and compounds 6232, 6403, 6405 and 6415.

FIG. 17 shows decrease in ECM crosslinking (as assessed by collagen (green) and fibronectin (red) staining) upon BAPN, 6232, 6403, 6405, or 6415 treatments.

FIG. 18 shows the effects of the compound 6415 on LOX and LOXL2 activity. 6415 was used at 5 and 10 uM concentrations in recombinant protein based lysyl oxidase activity assay and inhibited the activity of LOX and LOXL2 recombinant proteins. BAPN was used as a control at 10 mM dose.

FIG. 19 shows the lysyl oxidase activity and cell viability in Caki-1 and ACHN cell lines treated with increasing doses of BAPN and 6232.

FIG. 20 shows the cellular morphology of ACHN and Caki-1 cell lines when treated with 10 µM of the compound 6232.

FIG. 21 shows decrease in ECM crosslinking upon treatment of Caki-1 cells with compound 6232 at 10 uM and BAPN at 10 mM.

FIG. 22. Expression of LOX family members in cancer vs normal tissue by using TCGA dataset. A. Pan-cancer expression of LOX family members in the TCGA dataset. B. Expression of LOX, LOXL1 and LOXL2 in TNBCs vs normal breast. C. Expression of LOX, LOXL1 and LOXL2 in pancreatic tumors vs. normal tissue and kidney cancer vs normal tissue. ACC—Adenoid cystic carcinoma; BLCA—Bladder urothelial carcinoma; BRCA—Breast Cancer; CESC—Cervical squamous cell carcinoma; CHOL—Cholangiocarcinoma; COAD—Colon adenocarcinoma; DLBC-Diffuse large B cell lymphoma; ESCA—Esophageal cancer; GBM—Glioblastoma; HNSC—Head and neck squamous cell carcinoma; KICH—Kidney Chromophobe; KIRC—Kidney renal clear cell carcinoma; KIRP—Kidney renal papillary cell carcinoma; LAML—Acute Myeloid Leukemia; LGG—Low-grade glioma; LIHC—Liver Hepatocellular Carcinoma; LUAD—Lung Adenocarcinoma; LUSC—Lung squamous cell carcinoma; MESO—Mesothelioma; OV—Ovarian Cancer; PAAD—Pancreatic adenocarcinoma; PCPG—Pheochromocytoma and paraganglioma; PRAD—Prostate Adenocarcinoma; READ—Rectum Adenocarcinoma; SARC—Sarcoma; SKCM—Skin cutaneous melanoma; STAD—Stomach adenocarcinoma; TGTC—Tenosynovial giant cell tumors; THCA—Thyroid Cancer; THYM—Thymoma; UCEC—Uterine Corpus Endometrial Carcinoma; UCS—Uterine Carcinosarcoma; UVM—Uveal Melanoma.

FIG. 23. Association of the expression of LOX, LOXL1 and LOXL2 with survival in breast, pancreatic and kidney cancer patients. In the TCGA dataset, the expression of LOX, LOXL1 and LOXL2 associates with worse DFS in KIRC while higher expression of LOX and LOXL2 associates with worse relapse-free survival (RFS) in PAAD (in the TCGA dataset) and in chemotherapy-treated breast cancer (KM plotter database).

FIG. 24. LOX expression is increased in doxorubicin resistance and its high expression is associated with worse survival in chemotherapy treated TNBC patients. A. LOX mRNA expression in sensitive vs. resistant tumor xenografts. B. Picrosirius staining of the tumors from A. C. Kaplan-Meier survival curve representing DFS in chemotherapy-treated TNBC patients (n=77) separated from median LOX protein expression. D. IHC images of TNBC patient tissues with low and high LOX protein expression. *, P<0.05; **, P<0.01 in all figures.

Figure 25:
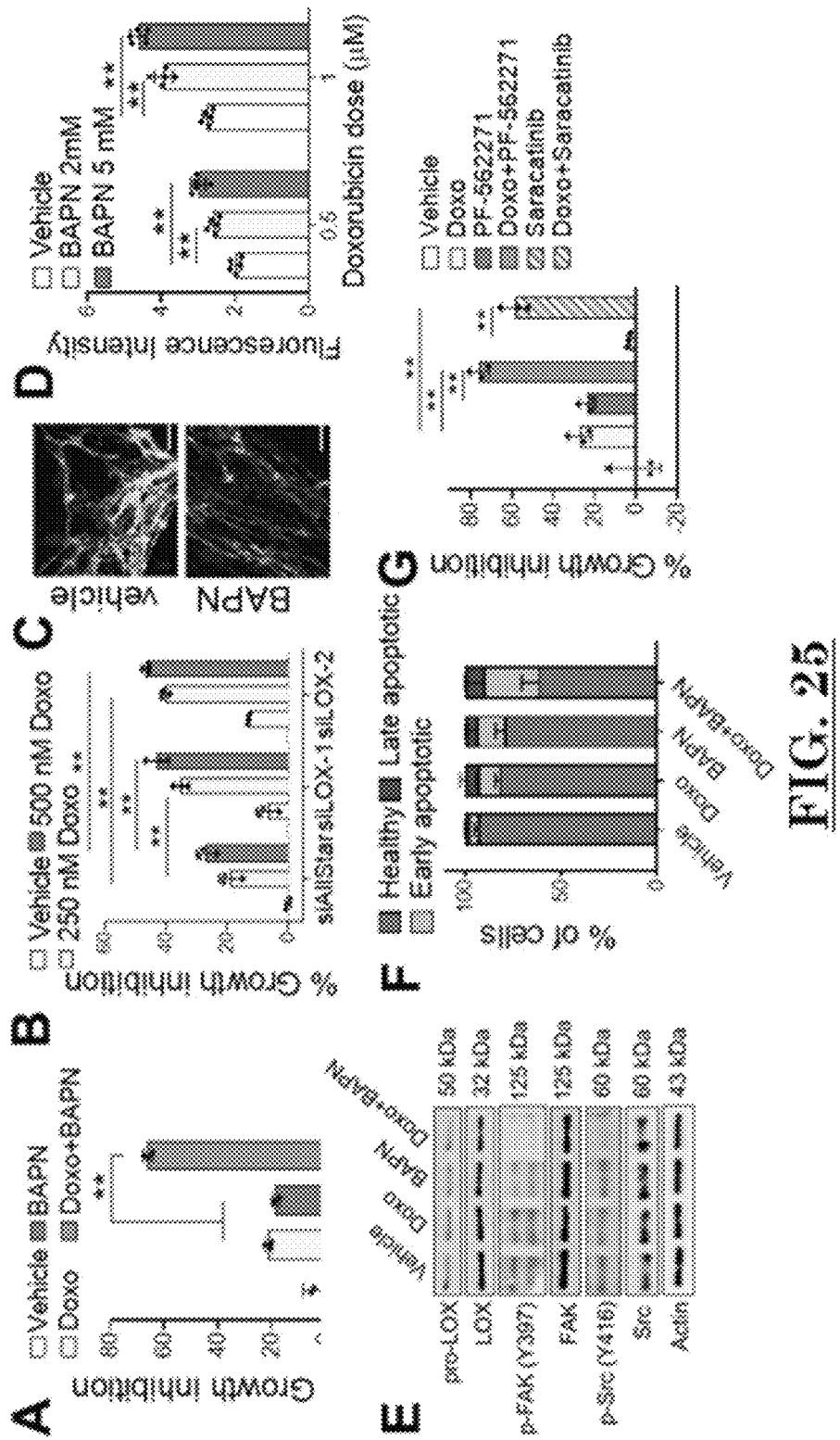
FIG. 25 shows LOX inhibition overcomes doxorubicin resistance in 3D culture.

FIG. 25. LOX inhibition overcomes doxorubicin resistance in 3D culture. A, B. % growth inhibition of 3D collagen I-embedded MDA-MB-231 cells treated with BAPN (A) or transfected with siLOX (B) in combination with doxorubicin. C. IF staining of type I collagen (green) and fibronectin (red) in HFF-derived ECM incubated with vehicle or BAPN-treated MDA-MB-231 cells. D. Relative doxorubicin fluorescence intensity upon BAPN-treatment in collagen I-embedded MDA-MB-231 cells. E. Western blot of LOX and FAK/Src signaling in collagen I-embedded MDA-MB-231 cells upon doxorubicin (1 uM) and BAPN (5 mM) treatment for 24 h. F. Annexin V staining in 3D collagen I-embedded MDA-MB-231 cells treated with Doxo+BAPN combination from E. G. % growth inhibition of 3D collagen I-embedded MDA-MB-231 cells treated with doxorubicin in combination with FAK (500 nM) or Src (500 nM) inhibitors.

Figure 26:
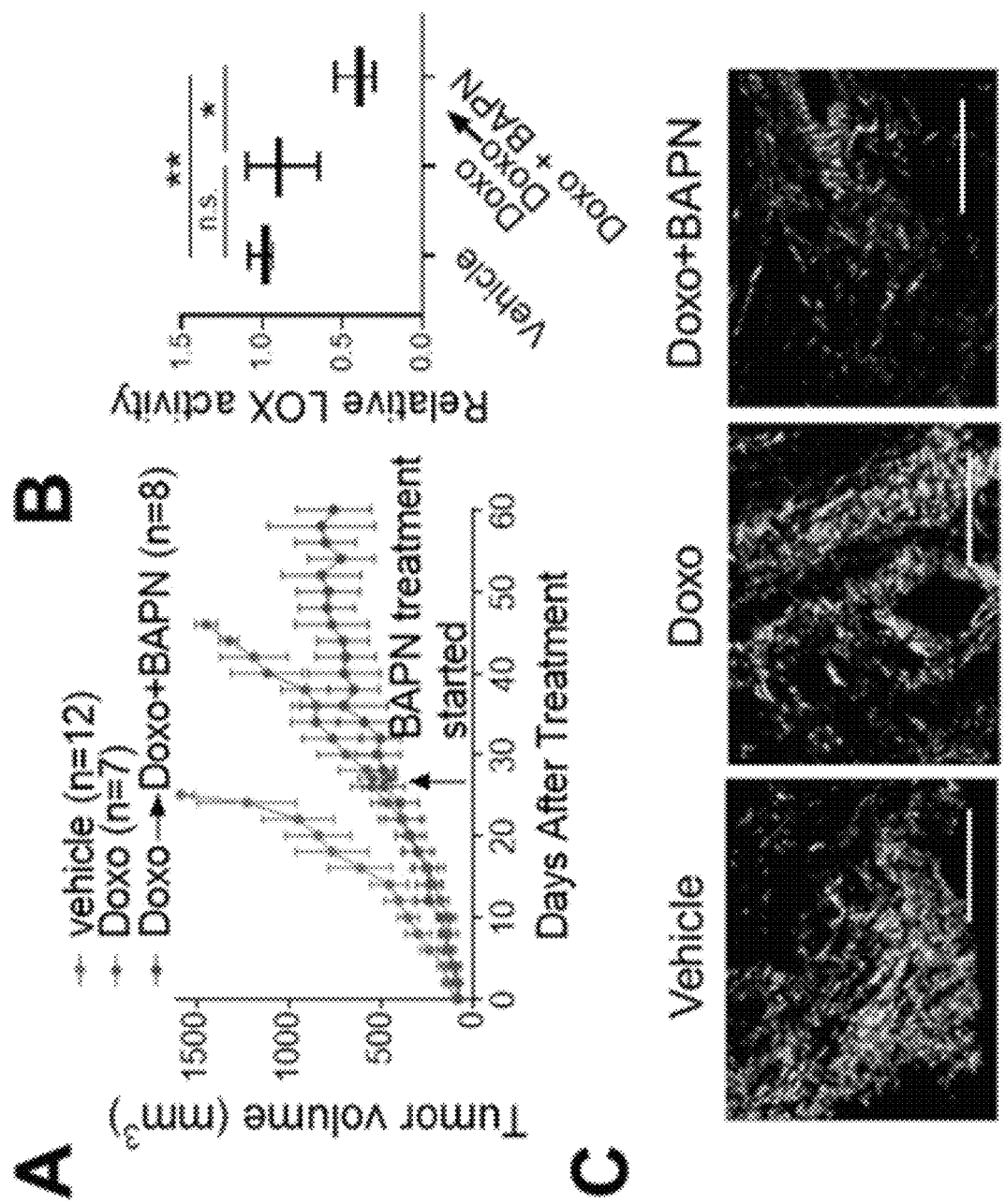
FIG. 26 shows inhibiting LOX overcomes resistance in acquired doxorubicin resistant MDA-MB-231 xenografts.

FIG. 26. Inhibiting LOX overcomes resistance in acquired doxorubicin resistant MDA-MB-231 xenografts. A. Tumor growth in xenografts treated with low dose doxorubicin until resistance develops followed by treatment with the combination of doxorubicin (2.5 mg/kg) and the LOX inhibitor, BAPN (100 mg/kg). B. Relative LOX activity in tumors from A. C. Representative images of Picrosirius red in tumors from A.

FIG. 27. Targeting LOX in TNBC PDX organoids or tumors overcomes resistance. A. Scheme showing the selection pipeline of PDXs for in vivo testing. B. Correlation analysis of LOX mRNA expression with hypoxia and focal adhesion scores in 15 different TNBC PDX models. Red dots show the positions of the selected TM01278. C. Representative images of TM01278 PDX organoids at day 0 and day 9 after treatment with doxorubicin (40 nM) and BAPN (25 mM) treatment, alone or in combination (left) and quantification of organoid diameter upon combination therapy for 9 days (right) (n=12 (vehicle, Doxo, BAPN), n=11 (Doxo+BAPN)). D. Tumor growth of TM01278 PDX upon treatment with doxorubicin (2 mg/kg) and BAPN (100 mg/kg), alone or in combination (n=5). Inset shows LOX expression in PDX tumors. E. Quantification of Picrosirius red staining in PDX tumors from D (n=4). F. Doxorubicin fluorescence quantification in tumors from D (n=6). G. Western Blots of FAK/Src signaling in PDXs treated with doxorubicin and BAPN alone or in combination.

FIG. 28. Summary of our LOX or LOX family inhibitor discovery pipeline.

FIG. 29. Characterization and selection of top hits from the high-throughput screen (HTS) of a diversified small-molecule library to identify novel LOX inhibitors. A. Inhibition of cell-based LOX activity and cell viability upon treatment with top 20 candidate LOX inhibitors at 10 uM. B. Doxorubicin sensitization upon combination of the selected 5 compounds (5 uM) with doxorubicin (1 uM). C, D. LOX activity assay with the recombinant LOX (C) LOXL2 (D) proteins incubated with 10 uM of 6229 and 6232, and 10 mM BAPN. μM=microM.

FIG. 30. LOX inhibitors generated based on SAR analysis.

FIG. 31. Novel 6232 analogs, 6403 and 6415, effectively inhibit lysyl oxidase activity, overcomes doxorubicin resistance and reduce collagen cross-linking and fibronectin assembly. A. Inhibition of LOX activity in MDA-MB-231 cells treated with 5 μM of the LOX inhibitors. B. Doxorubicin sensitization with 6232 and its analogs, 6403 and 6415, in 3D collagen-I culture. C. Collagen and fibronectin staining of vehicle or 6232 or 6403 or 6415-treated MDA-MB-231 cells embedded in collagen I. BAPN is used as a positive control.

Figure 32:
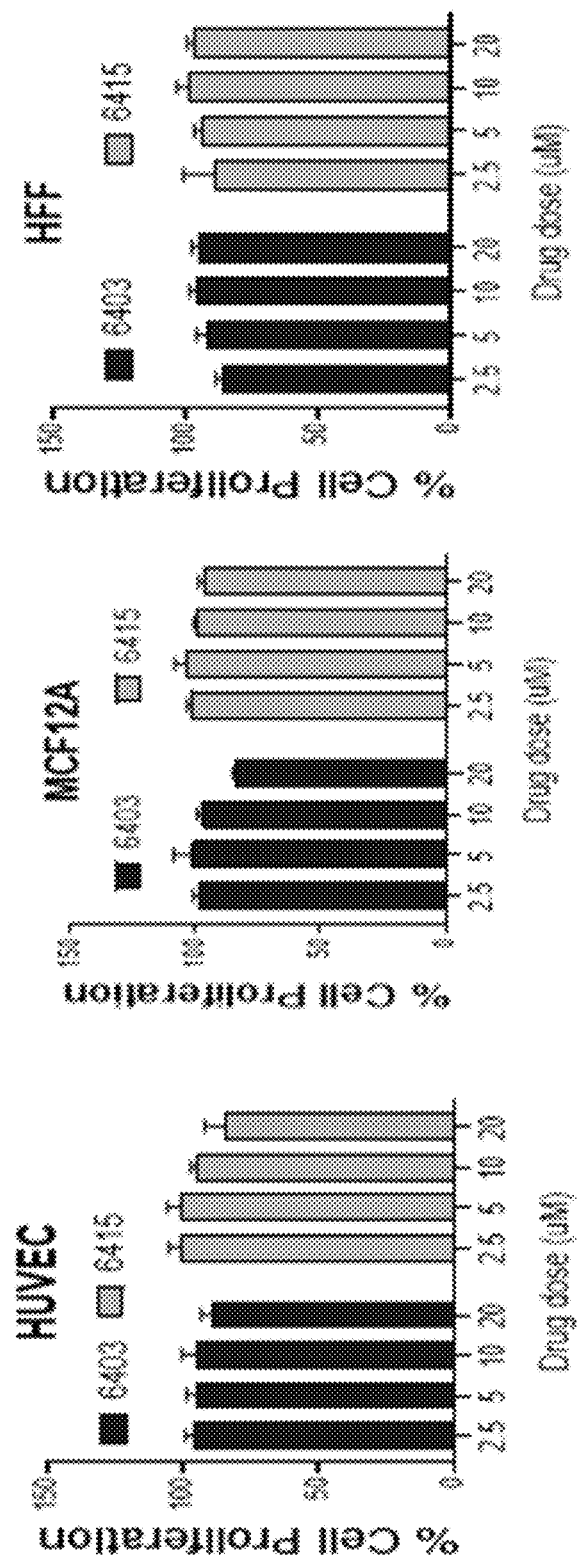
FIG. 32 shows 6232 derivatives, 6403 and 6415, show no cytotoxicity in normal cells.

FIG. 32. 6232 derivatives, 6403 and 6415, show no cytotoxicity in normal cells. Viability assay in normal breast cell line, MCF12A, human foreskin fibroblast cell line, HFF and human endothelial cell line, HUVEC treated with 6403 or 6415.

FIG. 33. While 6403 inhibits LOX recombinant protein, 6415 inhibits both LOX and LOXL2 recombinant proteins. A. Lysyl oxidase activity assay with the recombinant LOX, and LOXL2 proteins in the presence or absence of 10 uM 6403. B. Activity assay with the recombinant LOX, and LOXL2 proteins in the presence or absence of 10 uM 6415.

FIG. 34. 6232, 6403 and 6415 are more potent than LOX family inhibitor, BAPN. IC50 for cellular lysyl oxidase activity upon treatment of MDA-MB-231 cells with different LOX inhibitors. uM=microM.

FIG. 35. 6403 and 6415 led to doxorubicin chemosensitization in 3D culture of TNBC cell lines. Doxorubicin sensitization with 6232 analogs, 6403 and 6415, in 3D collagen-I culture of MDA-MB-231 (Doxo1: 0.75 uM, Doxo2: 1 uM, 6403: 5 μM, 6415:5 μM) (A) and HCC1143 (Doxo1: 1 uM, Doxo2: 2 μM, 6403: 5 μM, 6415:5 μM) (B).

FIG. 36. Combination of 6403 and 6415 with doxorubicin reduced the growth of the TNBC organoids. A. Representative images of TM01278 PDX organoids at day 0 and day 9 after treatment with doxorubicin (50 nM) and 6403 and 6415 treatments, alone or in combination. B. Quantification of organoid diameter and viability upon combination therapy for 9 days.

Figure 37:
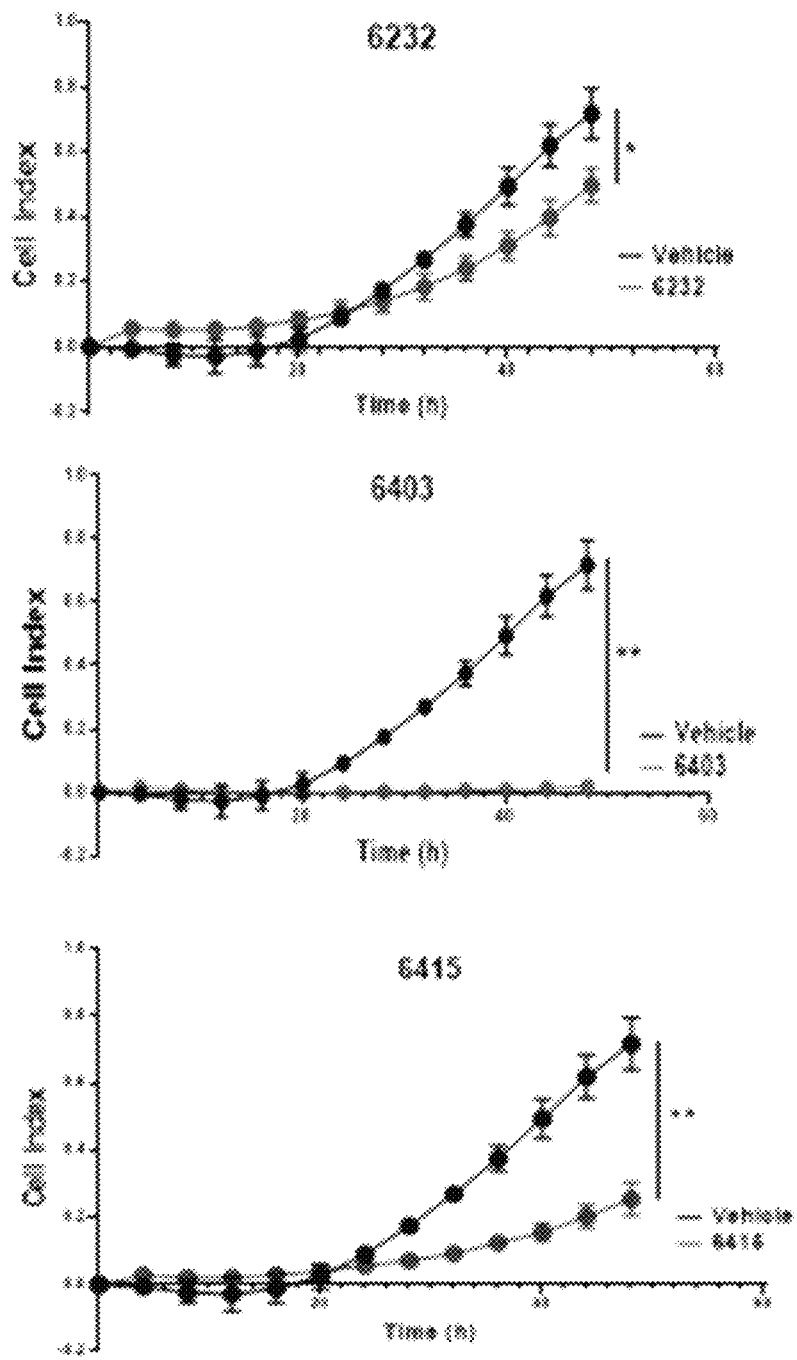
FIG. 37 shows LOX inhibitors, 6232, 6403 and 6415, reduced the migration capacity of the TNBC cell lines.

FIG. 37. LOX inhibitors, 6232, 6403 and 6415, reduced the migration capacity of the TNBC cell lines. RTCA-CIM plate used to measure the real-time migration of MDA-MB-231 cells upon treatment with 20 μM of 6232, 6403 and 6415 for 48 hours. (* p<0.05; ** p<0.01)

FIG. 38. Dose dependent inhibition of cellular LOX activity and growth inhibition in 3D upon treatment with 6232 and its analogs, 6403 and 6415.in ACHN cancer cell line. Inhibition of cell-based LOX activity in ACHN (A) and growth inhibition in collagen:matrigel (1:1) culture (B) cancer cell lines upon treatment with LOX inhibitors 6232, 6403 and 6415 (uM range). BAPN is used as a positive control (mM range) in 3D cell viability assay. Growth inhibition was measured by using 3D Cell Titer Glo kit.

Figure 39:
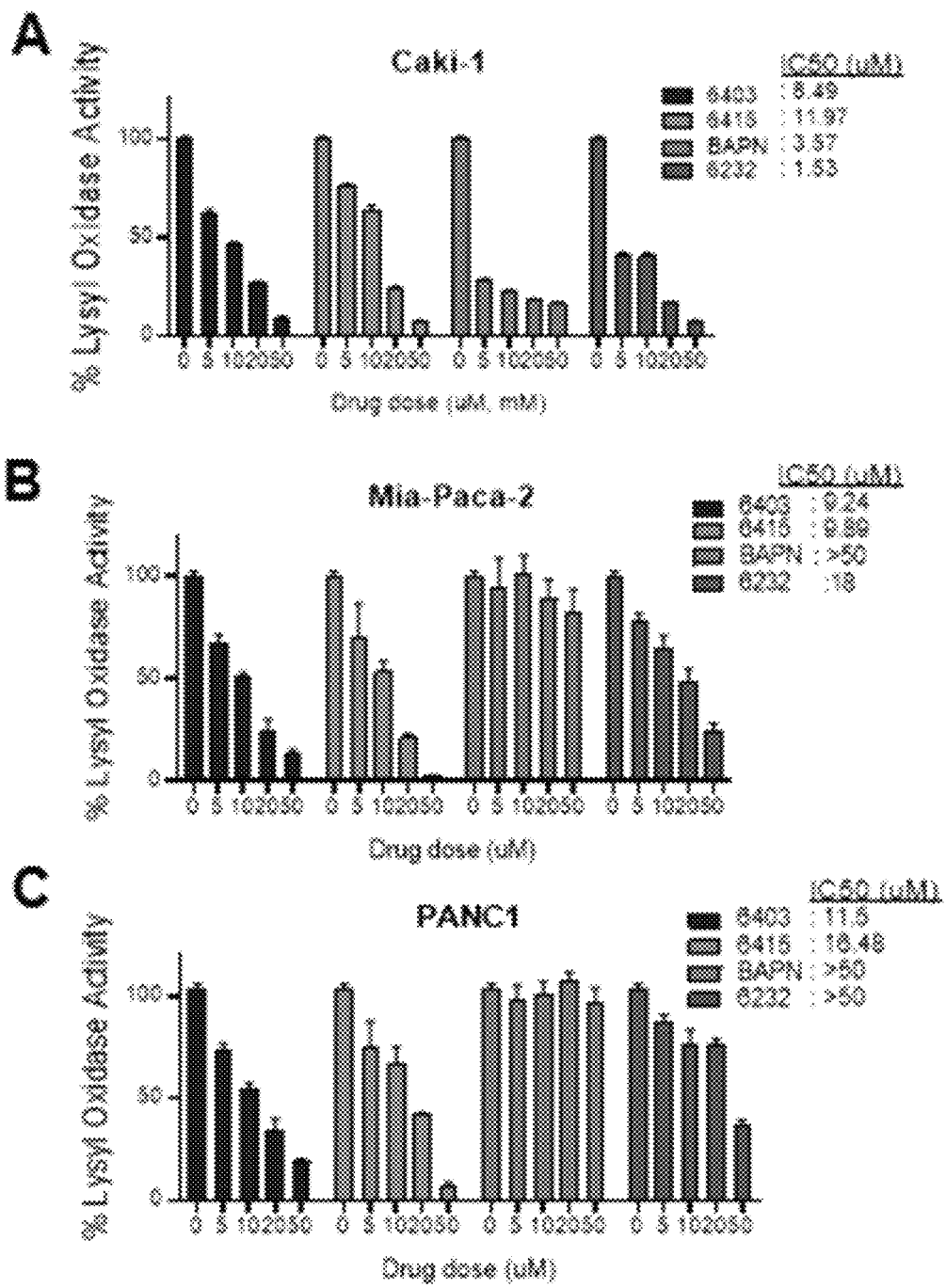
FIG. 39 shows inhibition of cellular LOX activity in pancreatic and kidney cancer cell lines.

FIG. 39. Inhibition of cellular LOX activity in pancreatic and kidney cancer cell lines. Inhibition of cellular LOX activity upon the treatment with BAPN, 6232, 6403 and 6415 in kidney cell line Caki-1 (A) and pancreatic cancer cell lines Mia-Paca-2 (B) and PANC1 (C).

Figure 40:
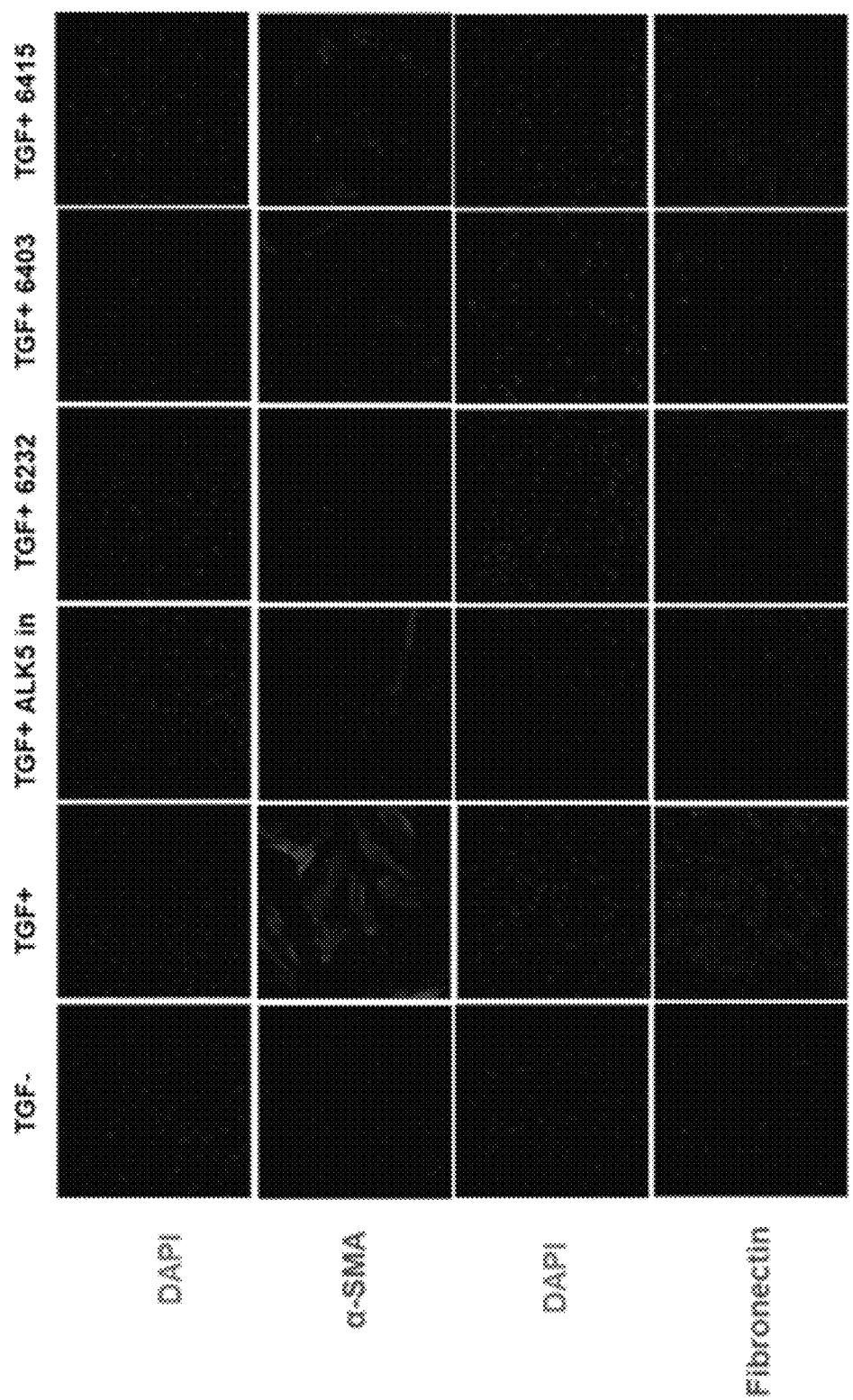
FIG. 40 shows treatment with 6232, and its analogs 6403 and 6415 inhibited the TGF-β-induced fibrosis in HFF cells.

FIG. 40. Treatment with 6232, and its analogs 6403 and 6415 inhibited the TGF-β-induced fibrosis in HFF cells. 24 hours serum-starved HFF cells were pretreated with inhibitors 1 hours. Then, fibrosis was induced by 10 uM of TGF-β for 48 hours in HFF cells. ALK5 (10 μM) inhibitor is used as a negative control. LOX inhibitors 6232, 6403 and 6415 were used at 10 uM concentration. HFF cells were stained with alpha-SMA and fibronectin primary antibodies. Nucleus of the cells was labeled with DAPI.

FIG. 41. In vivo testing of 6403 with respect to PK and toxicity. A. Summary of PK parameters of 6403 given orally with 50 mg/kg, n=3. B. H&E staining of organs of BALB/c mice treated daily with 50 or 200 mg/kg of 6403 for one week. C. Body weight of mice treated with vehicle or 25, 50, 75, 100 or 200 mg/kg of 6403 for 5 days. D. Cell-free enzymatic MAO-A and MAO-B assay.

FIG. 42. Efficacy of 6403 as a single agent in ccRC xenografts. Tumor volume (A), % body weight change (B) and blood count (C) of 6403-treated (50 mg/kg, PO, daily) ACHN xenografts. μg=microgram. LOX expression in ACHN cells is provided by an inset next to the graph in A.

Figure 43:
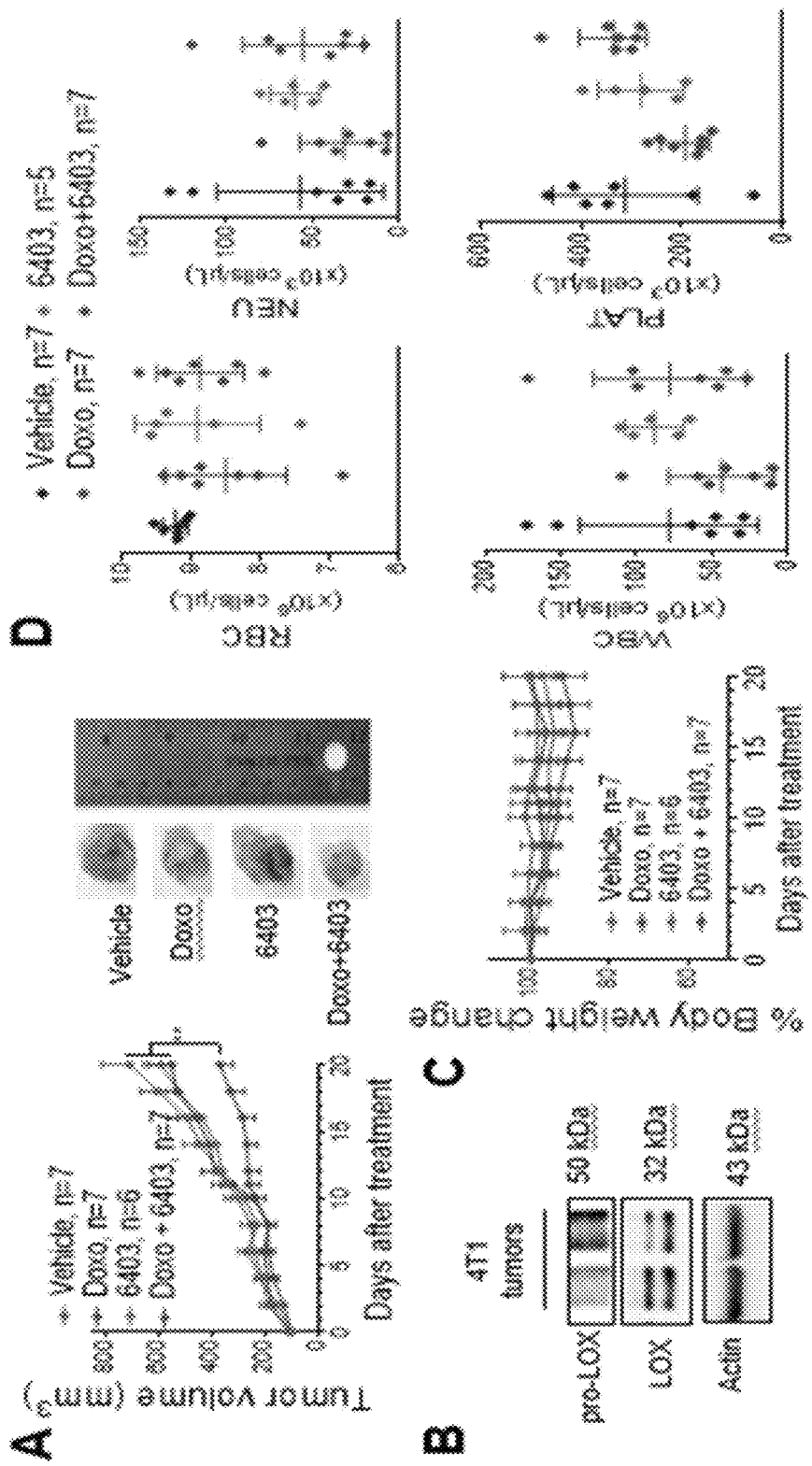
FIG. 43 shows that 6403 overcomes doxorubicin resistance without major toxicity in a syngeneic mouse model, 4T1.

FIG. 43. 6403 overcomes doxorubicin resistance without major toxicity in a syngeneic mouse model, 4T1. A. Tumor growth in 4T1 model treated with doxorubicin (2 mg/kg, I.V, weekly), 6403 (50 mg/kg, P.O, daily) or their combination. Representative pictures of the tumors shown on the right panel. B. Western blot analysis of LOX in 4T1 tumors from A. C. % body weight change of mice from A. D. Blood cell counts in mice from A at the end of the experiment.

Method

Cell Culture and Reagents

Human TNBC cell lines, MDA-MB-231, and HCC1143; Pancreatic cancer cell lines, PANC1, and Mia-PACA-2; Kidney cancer cell lines, ACHN, and Caki-1. All the cells were cultured in Dulbecco Modified Eagle Medium (Gibco, USA) supplemented with 50 U/ml penicillin/streptomycin, 1% non-essential amino acids and 10% fetal bovine serum (Gibco, USA). The cell lines were authenticated and tested for mycoplasma contamination regularly using MycoAlert mycoplasma detection kit (Lonza, NJ, USA). The cumulative culture length of cells between thawing and use in this study was less than 20 passages.

Western Blotting

Protein isolation and Western blotting were done as previously described, see Mishra, R. R. et al. Reactivation of cAMP Pathway by PDE4D Inhibition Represents a Novel Druggable Axis for Overcoming Tamoxifen Resistance in ER-positive Breast Cancer. *Clinical Cancer Research: An Official Journal of The American Association for Cancer Research* 24, 1987-2001, doi:10.1158/1078-0432.CCR-17-2776 (2018) and Saatci, O. et al. Targeting PLK1 overcomes T-DM1 resistance via CDK1-dependent phosphorylation and inactivation of Bcl-2/xL in HER2-positive breast cancer. *Oncogene* 37, 2251-2269, doi:10.1038/s41388-017-0108-9 (2018). Briefly, RIPA buffer was used to isolate total protein lysate in the presence of protease and phosphatase inhibitor cocktails, and protein concentrations were measured using the BCA Protein Assay Reagent Kit (Thermo Fisher Scientific, MA, USA). Equal amounts of protein were separated using 8-10% SDS-PAGE gel. Separated proteins were transferred to PVDF membranes (Bio-Rad, CA, USA) using a Trans-Blot turbo transfer system (Bio-Rad, CA, USA) and incubated with primary antibodies (LOX (Novus), LOXL1 (Santa-Cruz) and LOXL2 (Abcam)). Horseradish peroxidase-conjugated anti-mouse or anti-rabbit antibodies (Cell signaling Technology, MA, USA) were used as secondary antibodies, and signals were detected by enhanced chemiluminescence (Thermo Fisher Scientific, MA, USA). Images were acquired using Image Lab Software (Biorad, CA, USA).

Cell Embedding in Type I Collagen:Matrigel (1:1) Mix

Collagen solution was prepared at a concentration of 0.5-1 mg/ml from the rat tail collagen I (Corning, USA) with a neutralization step including the addition of 1N NaOH solution. Cells were trypsinazed and resuspended in collagen:matrigel mix (1:1). $8 \times 10^3$ cells were seeded into 96-well or µ-Slide 8-well glass bottom chambers. After 1 hour of incubation at room temperature, media was added on top of the solidified collagen:matrigel mix. Drug treatments were done 12 hours after cell seeding.

Immunofluorescence Staining

Immunofluorescence staining of cells was done in µ-Slide 8-well glass bottom chambers (Ibidi, Germany). Cells were fixed with 4% paraformaldehyde for 20 min, permeabilized with 0.5% Triton X-100 for 10 min and blocked in 5% BSA-PBS. Samples were incubated with primary (Collagen I, Fibronectin, F-actin, a-SMA) and secondary Alexa Fluor 647 or 488-labeled antibodies for 1.5 hours at room temperature. Cells were also counterstained with DAPI for 5 min. Images were acquired using ZEN 2012 SP5 (Black) LSM 700 (Carl Zeiss, DE).

Lysyl Oxidase Activity Assay

For cell-based lysyl oxidase activity, fluorometric Lysly Oxidase Activity Assay Kit (Abcam, USA) was used according to manufacturer's instructions. Briefly, after the treatment, 50 µl of supernatant from each well was incubated with reagent mix and fluorescence measured in multimode-reader at Ex/Em=540/590 nm wavelength.

For in vitro lysyl oxidase activity (for recombinant proteins), Lysyl Oxidase Activity kit (Biovision, USA) was used according to manufacturer's instructions. Briefly, 1 µg of LOX (Novus, USA), 0.2 µg of LOXL1 (Abcam, USA) and 0.1 µg of LOXL2 (Abcam, USA) were incubated with the reagent mix in the presence of inhibitors or vehicle. Lysyl oxidase activity of the wells was measured in multimode reader (every 30 sec, total 2.5 hours) in luminescence mode.

Chemosensitization in 3D Culture

Cells were embedded in type I collagen:matrigel mix as described above. Cells were grown in the presence of doxorubicin or LOX inhibitors alone or combination of LOX inhibitors with doxorubicin for 48 hours. After the treatment, cell viability was measured by using 3D Cell Titer Glo (Promega, USA) kit.

PDX-Derived TNBC Organoids

TNBC organoids were established from a fresh surgical tissue by cutting the tumor into small pieces and incubating in collagenase A solution with ROCK inhibitor on a shaker at 37° C. for 30 minutes. The collagenase activity was inhibited by adding FBS, and pipetting was done to ensure the formation of almost a single cell solution. After several washes with PBS, the cell pellet was dissolved in matrigel. Breast organoid media containing ROCK and GSK inhibitors was added after the Matrigel solidified. See, Sachs, N. et al. A Living Biobank of Breast Cancer Organoids Captures Disease Heterogeneity. Cell 172, 373-386 e310, doi: 10.1016/j.cell.2017.11.010 (2018). For drug testing studies, organoids were disrupted to single cells by digesting at 37° C. for 30 mins with TrypLE (A1217701, Gibco, NY, USA) in the presence of 10 µM Rock inhibitor (s1049, Selleckchem, TX, USA). Organoids were plated into wells of 96 well plate (20.000 cells/well) on a collagen-coated surface with media containing 2% Matrigel (356252, Corning, N.Y., USA). Drugs were added 72 hours after plating. Cells were grown in the presence of drug or vehicle for 9 days, and photos were taken from each well to show the organoid size. Organoid viability was measured by using 3D Cell Titer Glo (Promega, USA) kit.

Migration Assay

RTCA CIM Plate was used to assess the migration capacity of the cells upon LOX inhibitor treatment according to manufacturer's instructions. Briefly, 160 µl of 10% FBS containing media was added into each bottom chamber/50 µl of FBS free media into upper chamber and incubated 1 hour at 37° C. After the background measurement, $5 \times 10^4$ cells were seeded in FBS-free media into upper chamber in the presence of LOX inhibitors or vehicle. After the 30 min incubation at RT, real time cell migration was recorded for 48 hours.

Fibrosis Assay

Human foreskin fibroblasts (HFF), see Li, M. et al. Icaritin inhibits skin fibrosis through regulating AMPK and Wnt/β-catenin signaling. Cell Biochemistry and Biophysics 79, 231-238 (2021), cells were seeded into µ-Slide 8-well glass bottom chambers (Ibidi, Germany). Next day, media of the cells were replaced with 0.5% FBS contain media and incubated with 24 hours. Then, cells were pretreated either with ALK5 inhibitor (Sellekchem, USA) or LOX inhibitors for 1 hour and cells were incubated with 10 ng/ml of TGF-beta (R&D Biosystems, USA) for 48 hours. Staining of the markers followed the same procedure described in the Immunofluorescence section above.

PK Analysis

PK profiles of lead LOX inhibitor, 6403 was tested in BALB/c mice. Three mice per group were dosed by oral gavage at 50 mg/kg. Serum samples were collected at time points; 0.25, 0.5, 2, 7 and 24 hours. 6403 was diluted with serum from healthy mice as standard and serum levels of LOX inhibitors were quantified by LC-MS/MS methods, compared to the standard readings and followed by calculation of PK parameters, including $C_{max}$, AUC, $T_{1/2}$ values, clearance (Cl) and oral bioavailability (F %). $C_{max}$ represents the maximum concentration of drug that observed in the serum. AUC is a measure of the total exposure of the drug in the serum, $T_{1/2}$, half life, is the time required to eliminate half of the drug. Cl is defined as the volume of blood from which all drug is removed per minute.

MAO-GLO Assay

MAO-GLO assay (Promega, USA) was used to measure the MAO-A and MAO-B activity upon LOX inhibitor treatment according to the manufacturer's instructions. For the enzyme activity, substrate was used at a concentration of 160 µM and 16 µM for MAO-A and MAO-B, respectively. MAO-A and MAO-B enzymes (Active Motif, USA) were used in 0.2 µg/per well. Reaction mix, enzymes, and drugs (30, 10, 3, 1, 0.3, and 0.1 nM) were mixed and incubated for 3 hours at RT. Then, 50 µl of luciferin was added into wells and incubated for 20 min at RT. Luciferase signals were measured by using a multimode reader.

Syngeneic and Xenograft Mice Tumor Model

For kidney xenografts, $4 \times 10^6$ ACHN cells were mixed with 1:1 DMEM and matrigel and injected into the flank of the BALB/c nude mice. Mouse weight and tumor volumes were measured every second day using calipers. When tumor sizes reach 100 mm$^3$, mice were randomly distributed into vehicle and 6403 treatment group. Mice were treated daily by oral gavage with vehicle v (50% PEG400, 1% Tween 80 in acetate buffer pH=4) or 50 mg/kg of 6403.

500,000 4T1 cells were injected into MFP of 6-8 weeks old female BALB/c mice. When the tumors reach 100 mm3, mice were randomly distributed to 4 groups and treated with vehicle, doxorubicin (2 mg/kg once a week, I.V.), 6403 (50 mg/kg daily, oral gavage) or the combination of doxorubicin with 6403. Tumor volumes were measured using a caliper every two days, and body weights were also recorded. After 3 weeks of treatment, blood was withdrawn, and blood cells were quantified using VetScan HM5 Hematology Analyzer.

Bioinformatic Analyses

Patient data for normal vs. tumor comparisons were retrieved from the NCBI GEO database (accession ID: GSE76250). Patient data for survival analyses were retrieved from TCGA database using cBio Portal, see Cerami, E. et al. Vol. 2 401-404 (AACR, 2012) and Lopes, C. T. et al. Cytoscape Web: an interactive web-based network browser. *Bioinformatics* 26, 2347-2348 (2010), and from online survival analysis tool, KM-plotter. See, Gyorffy, B. et al. An online survival analysis tool to rapidly assess the effect of 22,277 genes on breast cancer prognosis using microarray data of 1,809 patients. *Breast Cancer Research and Treatment* 123, 725-731 (2010). Survival curves were generated based on $25^{th}$ percentile separation using Kaplan-Meier method, and significance between groups was calculated by Log-rank test. Significance between normal vs tumor expression was calculated using unpaired Student's t-test. Boxplots show median number, and the $25^{th}$ to $75^{th}$ quartiles. Upper and lower whiskers denote the minimum and maximum values in the corresponding group. Graphs and curves were drawn using GraphPad software (GraphPad software Inc., La Jolla, Calif., USA). Significance threshold was described as *$P<0.05$; $P<0.01$; *$P<0.001$; ns, not significant.

The compounds of the current disclosure have wide-ranging impact on disease treatment. Indeed, the compounds disclosed herein, and or their pharmaceutically acceptable salts, may be administered in a therapeutically effective amount to inhibit LOX and LOX family members in both a LOX-specific as well as pan-LOX manner. Indeed, the compounds disclosed herein may be administered as anti-cancer agents where cancer is selected from the group consisting of lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; myelofibrosis, kidney cancer; cancer of the head and neck; cancer of the stomach; multiple myeloma; testicular cancer; germ cell tumor; neuroendocrine tumor; cervical cancer; oral cancer, carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

Indeed, compounds 6232, 6403, and 6415, however the current disclosure is not limited to just these compounds and should not be read restrictively or exclusively in this sense, can be used to target cancers and diseases caused by LOX family members as well as to induce metastasis inhibition. The compounds disclosed herein inhibit both cell-based lysyl oxidase activity and recombinant protein based lysyl oxidase activity. The compounds may a pharmaceutically acceptable salt thereof, or a pharmaceutical composition, used in the treatment of fibrosis, neurodegenerative, angiogenesis-related diseases and cancer, which show aberrant LOX family expression and/or lysyl oxidase activity. Indeed, the compounds of the current disclosure may be used as a single agent and/or in combination with standard of care therapies, as well as chemotherapy, immunotherapy or radiotherapy in both adjuvant and neo-adjuvant settings. Further, the compounds of the current disclosure may be used with small molecule treatments to address the diseases/disorders herein. The compounds disclosed herein may be used to treat diabetes-induced fibrosis and retinopathy, Fibrosis may include liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis. The compounds can also be used to treat angiogenesis related diseases. Indeed, the compounds disclosed herein may be administered with or in conjunction with a second therapeutic agent selected from anti-cancer agent, anti-inflammatory, anti-hypertensive, anti-fibrotic, anti-angiogenic agent, and an immunosuppressive agent. The current compounds also may be used to treat kidney disorders such as kidney fibrosis, renal fibrosis, acute kidney injury, chronic kidney disease, diabetic nephropathy, glomerulosclerosis, vesicoureteral reflux, tubulointerstitial renal fibrosis and glomerulonephritis. Further, the compounds of the current disclosure may be directed to healing, remedying hypertrophic scarring, keloids, and diabetic skin and may be used for cosmetic applications. See *Pathol Biol* (Paris) 2005 September; 53(7):448-56. doi: 10.1016/j.patbio.2004.12.033.

Examples Synthesis Routes

Compounds 6232, 6398, 6399, 6400, 6401, 6402, 6403, 6404, 6405, 6406, 6407, 6408, 6409, 6410, 6411, 6412, 6413, 6414, and 6415 were purchased from Chembridge Corporation (San Diego, Calif., USA, 92121) and tested as is. The synthesis of compounds 6424 (synthesized as formate salt of 6403), 6432 (synthesized as formate salt of 6405), 6433 (synthesized as formate salt of 6232) and 6439 (synthesized as formate salt of 6415) are described below. Compounds 6425 and 6426 have not been previously synthesized and are novel. Compounds purchased from Chembridge can be resynthesized using the same general methods. The general scheme is shown below including the synthesis of future derivatives including substitutions on the 4-methylthiazol-2-amine and aniline rings:

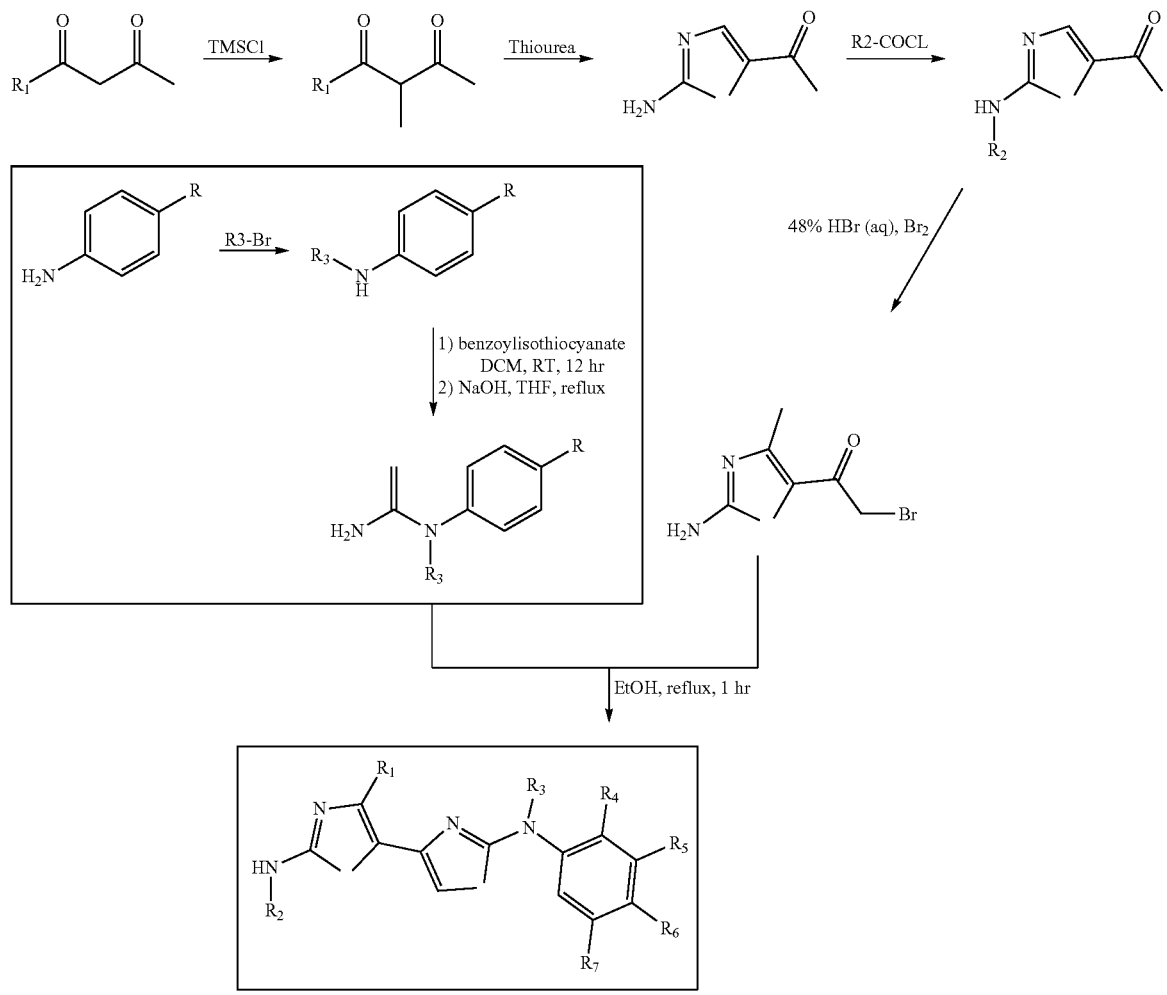

R1 = alkyl, aryl, benzyl etc
R3 = alkyl, benzyl
R2, R4-R7 = NHCO-alkyl, phenyl, benzyl, etc,
SO2NH-alkyl, phenyl, benzyl, etc,
O-alkyl, phenyl, benzyl, etc,

Synthesis of 1-(2-amino-4-methyl-thiazol-5-yl)-2-bromo-ethanone (1)

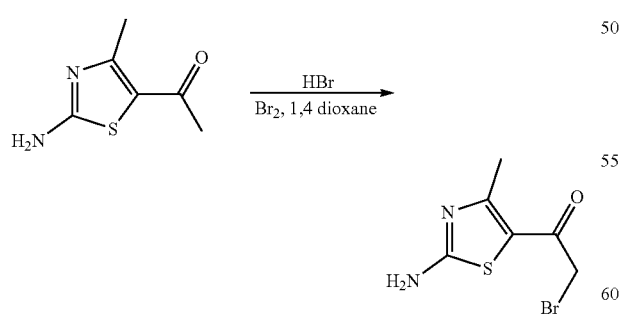

1-(2-amino-4-methyl-thiazol-5-yl)ethanone (5 g) was dissolved in HBr (20 ml) and allowed to warm to 60° C. Br$_2$ (4.6 g) was then dissolved in 1,4-dioxane and was added in a dropwise manner. The reaction was allowed to stir at 60° C. for 3 hours. After cooling to RT, the mixture was basified with Na$_2$CO$_3$ after which solid product came out of solution. The solid was removed by filtration. After extraction of the remaining solution with ethyl acetate, the organic layer was then washed with brine, dried over sodium sulfate, and was rotovapped to dryness. The remaining crude material was combined with the filtered solid and was dried in a vacuum desiccator (7.5 g, 50% purity), ESI-MS (pos): m/z 235 (M+H)$^+$ (expected 235.10).

Synthesis of N-[4-[[4-(2-amino-4-methyl-thiazol-5-yl)thiazol-2-yl]amino]phenyl]acetamide (6403, 6424)

Synthesis of N-[4-(carbamothioylamino)phenyl]acetamide

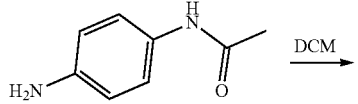

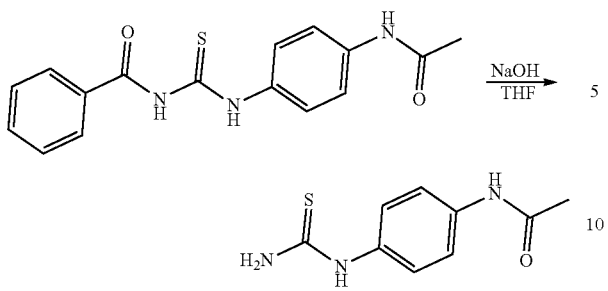

N-(4-aminophenyl)acetamide (6 g) was dissolved in anhydrous DCM and benzoyl isothiocyanate (8.15 g) was added in a dropwise fashion at RT. The reaction was then allowed to stir overnight. The solvent was removed and the products re-dissolved in 1:1 THF/1M NaOH, and then allowed to reflux at 75° C. for 3 hours. The sample was cooled to RT, diluted in water (~150 mL) and was extracted ethyl acetate (4×) to yield N-[4-(carbamothioylamino)phenyl]acetamide (2.2 g, 23% yield, 86% purity) ESI-MS (pos): m/z 210.0309 (M+H)$^+$ (expected 210.06).

Synthesis of N-[4-[[4-(2-amino-4-methyl-thiazol-5-yl)thiazol-2-yl]amino]phenyl]acetamide (6403, 6424)

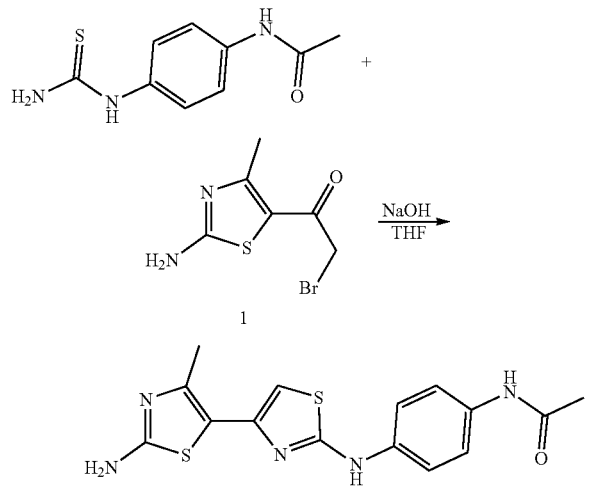

N-[4-(carbamothioylamino)phenyl]acetamide (1.1 g) and 1-(2-amino-4-methyl-thiazol-5-yl)-2-bromo-ethanone (1.85 g) were dissolved in 30 mL ethanol and the solution was heated to 90° C. for 2-3 h. After completion of the starting material the solvent was removed under reduced pressure at 45° C. water bath temperature. The crude material was re-dissolved in 3 mL of DMSO and purified by Medium Pressure Liquid Chromatography using a C18 reverse phase column and acetonitrile-water as eluent with 1% aqueous formic acid additive to obtain the desired product (1.3 g, 99% purity) in good yield (71.6%). $^1$H-NMR (400 MHz, D$_6$ DMSO) δ ppm 10.20 (s, 1H), 9.849 (s, 1H), 8.141 (s, 1H), 7.500-7.731 (m, 6H), 2.353 (s, 3H), 2.025 (s, 3H). ESI-MS (pos): m/z 346.1247 (M+H)$^+$ (expected 346.08).

Synthesis of 4-[[4-(2-amino-4-methyl-thiazol-5-yl)thiazol-2-yl]-methyl-amino]phenol (6415, 6439)

1) Synthesis of 4-(methylamino)phenol

An oven dried 250 mL round bottom flask was charged with 4-aminophenol (5 g), and to 20 mL of dimethylcarbonate (20 ml) was added followed by dimethoxyethane (20 mL) and NaY catalyst (5 g) in a sequential manner. The mixture was heated to 86° C. for 16 h. Then the solvent and excess reagent was evaporated and the crude material re-dissolved in 70-80 mL of Methanol and solid catalyst was filtered through celite pad and the methanol was concentrated under reduced pressure at 45° C. water bath temperature to obtained the product (5.6 g, yield 14%). ESI-MS (pos): m/z 124 (M+H)$^+$. Expected 124.

2) Synthesis of 1-(4-aminophenyl)-1-methylthiourea

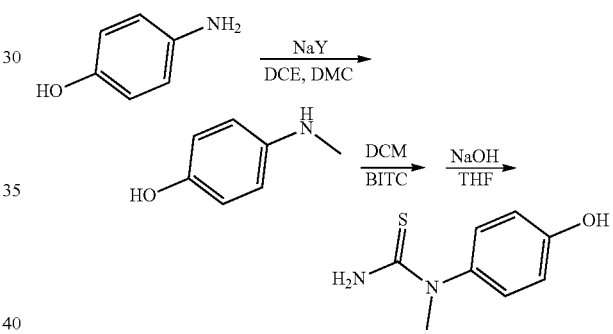

Crude 4-(methylamino)phenol (2.5 g) was dissolved in anhydrous DCM, then the Benzoyl isothiocyanate (5.0 g) was added in a dropwise fashion at room temperature (25° C.). During the process of addition the reaction mixture was slightly warmed. The reaction was then allowed to stir at room temperature overnight. After 16 h, the DCM was evaporated to dryness, then a 1:1 THF/1M NaOH solution was added until the solids were completely dissolved. The reaction was then allowed to reflux at 75° C. for 8 hr. The organic and aqueous layers were separated, aqueous layer was acidified with conc. HCl (pH=3-4) and then extracted with ethyl acetate, the solids were filtered and the organic layer was concentrated under reduced pressure. LCMS showed the desired mass peak at 183.

3) Synthesis of 4-[[4-(2-amino-4-methyl-thiazol-5-yl)thiazol-2-yl]-methyl-amino]phenol (6415, 6435)

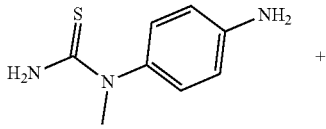

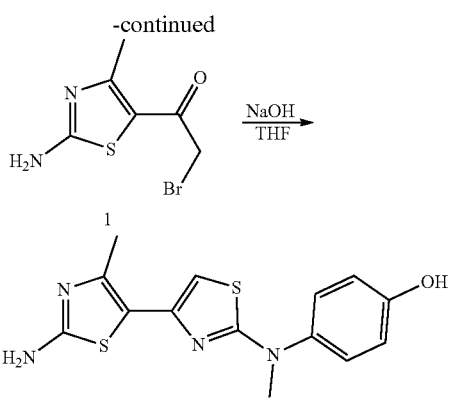

1-(4-aminophenyl)-1-methylthiourea (1.8 g) and 1-(2-amino-4-methyl-thiazol-5-yl)-2-bromo-ethanone (3.48 g) were dissolved in 30 mL ethanol and the solution was heated to 90° C. for 2-3 h. After completion of the starting material the solvent was removed under reduced pressure at 45° C. water bath temperature. The crude material was re-dissolved in 3 mL of DMSO and purified by Medium Pressure Liquid Chromatography using a $C_{18}$ reverse phase column and acetonitrile-water as eluent with 1% aqueous formic acid additive to obtain the desired product (2.5 g, 99% purity) in good yield (79.5%). $^1$H-NMR (400 MHz, $D_6$ DMSO) δ ppm 7.235-7.258 (m, 2H), 6.900 (s, 1H), 6.818-6.850 (m, 2H), 3.379 (s, 3H), 2.2848 (s, 3H). ESI-MS (pos): m/z 319.1 (M+H)$^+$ (expected 319.1).

Synthesis of N-[4-[[4-(2-amino-4-methyl-thiazol-5-yl)thiazol-2-yl]amino]phenyl]-3-methoxy-propanamide (6425)

1) Synthesis of N-[4-(carbamothioylamino)phenyl]-3-methoxy-propanamide

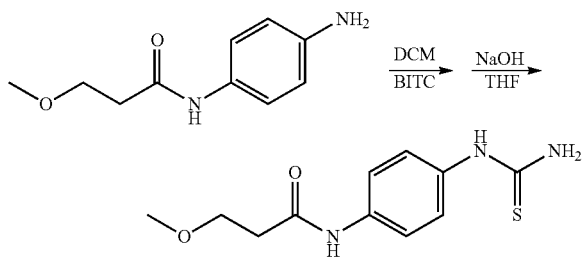

N-(4-aminophenyl)-3-methoxy-propanamide (0.24 g) was suspended in 2 mL of dry DCM and the benzoyl isothiocyanate (0.26 g) was separately dissolved in 1 mL of dry DCM. The benzoyl isothiocyanate was then added to the aniline dropwise over the course of 1 min with stirring. The solution was then rotovapped to dryness and dissolved in a solution of THF/1M NaOH (1:1). The solution was then refluxed at 75° C. for 3 hours. The sample was then cooled to room temperature, diluted with water, and extracted 3× with ethyl acetate. The organic solution was then dried over sodium sulfate, filtered, and rotovapped to dryness and purified with medium pressure liquid flash chromatography to yield the product (0.053 g, 16.6% yield, 99% purity). ESI-MS (pos): m/z 254.1 (M+H)$^+$ (expected 254.1).

2) Synthesis of N-[4-[[4-(2-amino-4-methyl-thiazol-5-yl)thiazol-2-yl]amino]phenyl]-3-methoxy-propanamide (6425)

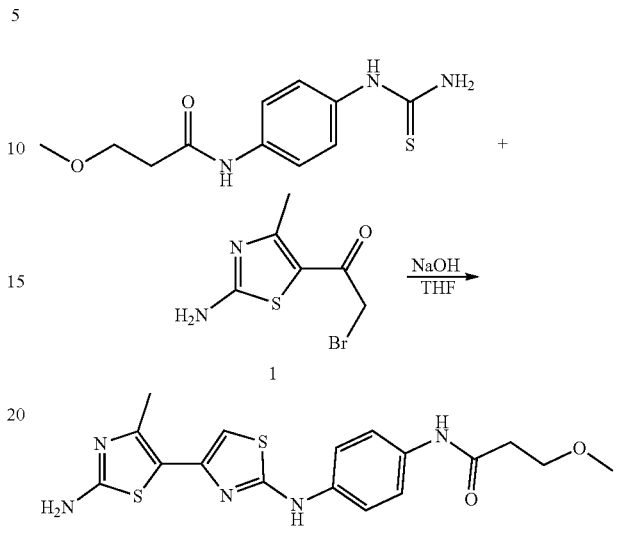

N-[4-(carbamothioylamino)phenyl]-3-methoxy-propanamide (0.019 g) and 1 (0.023 g) were dissolved in ethanol and were allowed to reflux for 90 min after which the sample was then rotovapped to dryness, dissolved in DMSO, and was purified by reverse-phase flash chromatography to yield the product (0.029 g, 99% purity). ESI-MS (pos): m/z 390.1 (M+H)$^+$ (expected 390.1).

Synthesis of N-[4-[[4-(2-amino-4-methyl-thiazol-5-yl)thiazol-2-yl]amino]phenyl]pentanamide (6526)

1) Synthesis of N-[4-(carbamothioylamino)phenyl]pentanamide

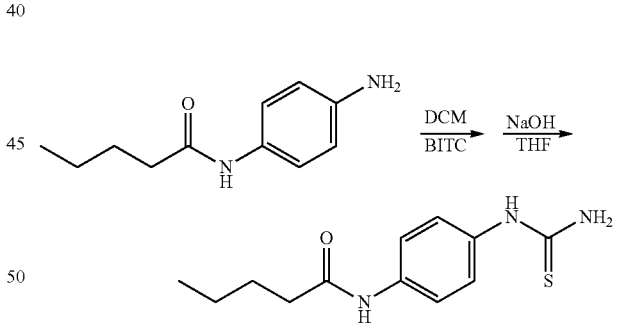

N-(4-aminophenyl)pentanamide (0.044 g) was suspended in 2 mL of dry DCM and the benzoyl isothiocyanate (0.047 g) was separately dissolved in 1 mL of dry DCM. The benzoyl isothiocyanate was then added to the aniline dropwise over the course of 1 min with stirring. The solution was then rotovapped to dryness and dissolved in a solution of THF/1M NaOH (1:1). The solution was then refluxed at 75° C. for 3 hours. The sample was then cooled to room temperature, diluted with water, and extracted 3× with ethyl acetate. The organic solution was then dried over sodium sulfate, filtered, and rotovapped to dryness and purified with medium pressure liquid flash chromatography to yield the product (0.007 g). ESI-MS (pos): m/z 252.1 (M+H)$^+$ (expected 252.1).

2) Synthesis of N-[4-[[4-(2-amino-4-methyl-thiazol-5-yl)thiazol-2-yl]amino]phenyl]pentanamide (6526)

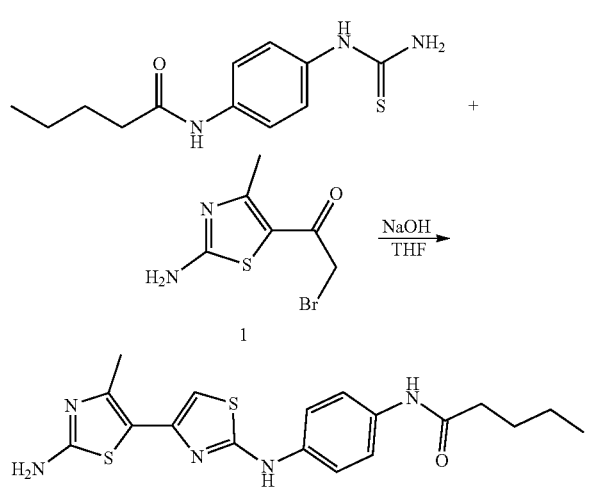

N-[4-(carbamothioylamino)phenyl]pentanamide (0.0073 g) and 1 (0.0047 g) were dissolved in ethanol and were allowed to reflux for 90 min after which the sample was then rotovapped to dryness, dissolved in DMSO, and was purified by reverse-phase flash chromatography to yield the product (0.038 g, 99% purity). ESI-MS (pos): m/z 388.1 (M+H)$^+$ (expected 388.1).

Synthesis of 4-methyl-5-[2-(4-nitroanilino)thiazol-4-yl]thiazol-2-amine (6232, 6433)

1) Synthesis of (4-nitrophenyl)thiourea

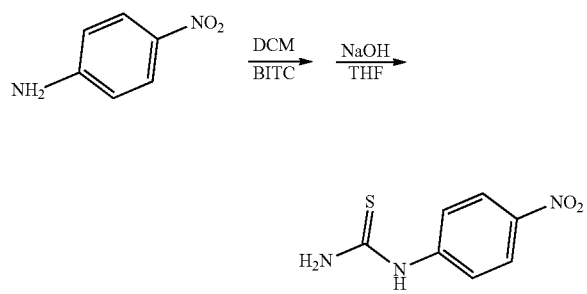

4-nitroaniline (2.0 g) was suspended in 2 mL of dry DCM and the benzoyl isothiocyanate (2.95 g) were separately dissolved in 1 mL of dry DCM. The benzoyl isothiocyanate was then added to the aniline dropwise over the course of 1 min with stirring. The solution was then rotovapped to dryness and dissolved in a solution of THF/1M NaOH (1:1). The solution was then refluxed at 75° C. for 1 hour. The sample was then cooled to room temperature, diluted with water, and extracted 3× with ethyl acetate. The organic solution was then dried over sodium sulfate, filtered, and rotovapped to dryness and purified with medium pressure liquid flash chromatography to yield the product (0.181 g). ESI-MS (pos): m/z 198.0 (M+H)+(expected 198.0).

2) Synthesis of 4-methyl-5-[2-(4-nitroanilino)thiazol-4-yl]thiazol-2-amine (6232, 6433)

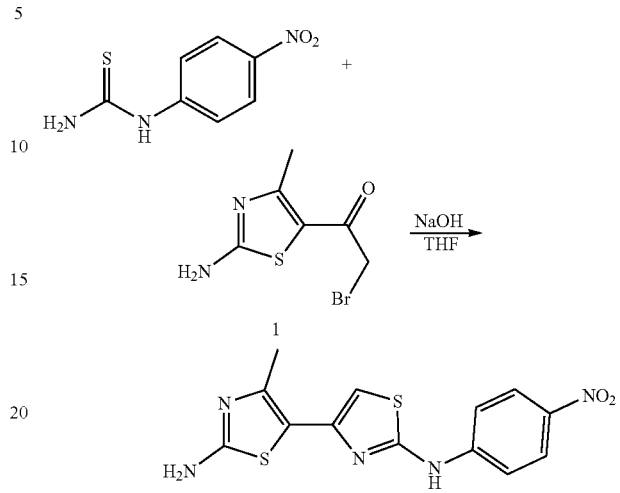

(4-nitrophenyl)thiourea (0.18 g) and 1 (0.30 g) were dissolved in ethanol and were allowed to reflux for 90 min after which the sample was then rotovapped to dryness, dissolved in DMSO, and was purified by reverse-phase flash chromatography to yield the product (0.041 g, 99% purity). (expected 334.0). $^1$H-NMR (400 MHz, D$_3$ Methanol) 6 ppm 8.027-8.124 (m, 3H), 7.742-7.766 (d, 2H), 6.667 (s, 1H), 2.326 (s, 3H). ESI-MS (pos): m/z 334.0 (M+H)$^+$ expected 334.0.

Synthesis of 4-((2'-amino-4'-methyl-[4,5'-bithiazol]-2-yl)amino)benzenesulfonamide (6405, 6432)

1) Synthesis of (4-sulfamoylphenyl)thiourea

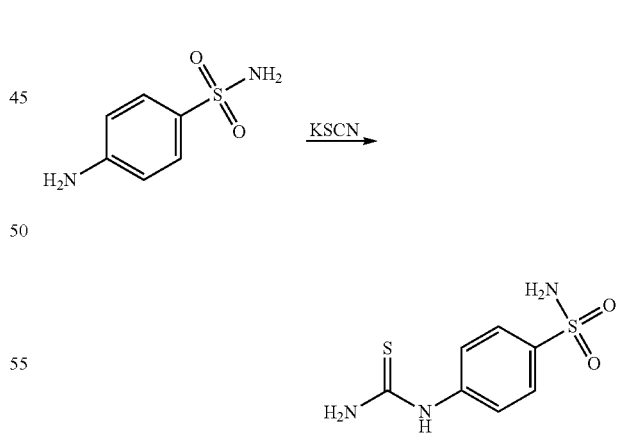

4-aminobenzenesulfonamide (0.10 g) was dissolved in HCl with warming and was then allowed to cool to RT. Potassium thiocyanate (0.056 g) was then added and the sample irradiated in the microwave at 90° C. for 2 hours. The sample was then transferred to a vial, chilled on ice and scratched to precipitate, and was filtered, leaving a white solid (0.006 g, 99% pure) ESI-MS (pos): m/z 232.0 (M+H)$^+$ (expected 232.3).

2) Synthesis of 4-((2'-amino-4'-methyl-[4,5'-bithiazol]-2-yl)amino)benzenesulfonamide (6405, 6432)

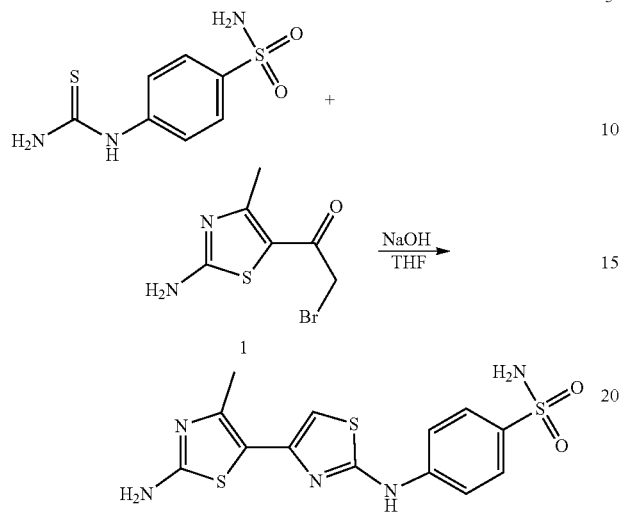

(4-sulfamoylphenyl)thiourea (0.13 g) and 1 (0.12 g) were dissolved in ethanol and were allowed to reflux for 90 min after which the sample was then rotovapped to dryness, dissolved in DMSO, and was purified by reverse-phase flash chromatography to yield the product (0.064 g, 99% purity). ESI-MS (pos): m/z 368.0 (M+H)+ (expected 368.0).

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

What is claimed is:

1. A method for inhibiting lysyl oxidases comprising:
administering a therapeutically effective amount of a compound or its pharmaceutically acceptable salt having formula I;

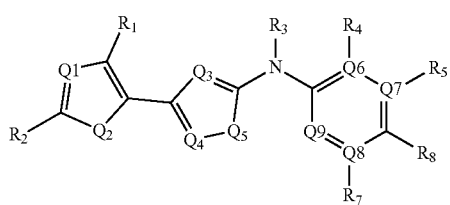

Wherein:
R1 is CH3;
R2 is H, NH2, or NHR;
R3 is H or CH3;
R4 is H;
R5 is H;
R6 is NHCOCH3, NO2, C2OH, or OH;
R7 is H;
Q1 is N;
Q2 is S;
Q3 is N;
Q4 is CH;
Q5 is S;
Q6 is CH;
Q7 is CH;
Q8 is C; and
Q9 is CH;
wherein the compound or its pharmaceutically acceptable salt inhibits cell-based lysyl oxidase activity and/or recombinant protein based lysyl oxidase activity assays.

2. The method of claim 1, wherein the therapeutically effective amount of the compound or its pharmaceutically acceptable salt is administered to treat a neurodegenerative disease, an angiogenesis-related disease, Alzheimer's disease, fibrosis including: liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis, diabetes, cerebral hemorrhage with amyloidosis, cardiac hypertrophy, Hutchinson-Gilford Progeria Syndrome, retinopathy, chemoresistance, and/or a kidney disorder including: kidney fibrosis, renal fibrosis, acute kidney injury, chronic kidney disease, diabetic nephropathy, glomerulosclerosis, vesicoureteral reflux, hypertrophic scarring, keloids, diabetic skin, tubulointerstitial renal fibrosis and/or glomerulonephritis.

3. The method of claim 2, wherein the cancer is selected from the group comprising lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; myelofibrosis, kidney cancer; cancer of the head and neck; cancer of the stomach; multiple myeloma; testicular cancer; germ cell tumor; neuroendocrine tumor; cervical cancer; oral cancer, carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma and/or a leiomysarcoma.

4. The method of claim 1, wherein the compound or its pharmaceutically acceptable salt has formula:

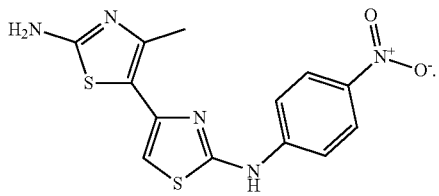

5. The method of claim 1, wherein the compound or its pharmaceutically acceptable salt has formula:

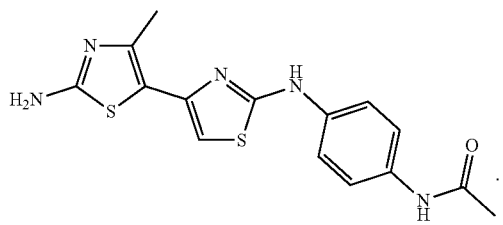 [SMILES: CC(=O)Nc1ccc(Nc2nc(-c3sc(N)nc3C)cs2)cc1]

6. The method of claim 1, wherein the compound or its pharmaceutically acceptable salt has formula:

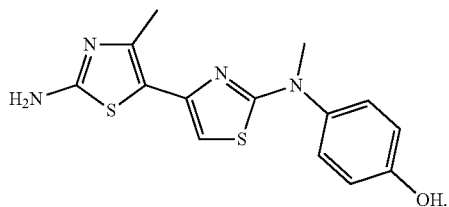 [SMILES: Cc1nc(N)sc1-c1csc(N(C)c2ccc(O)cc2)n1]

7. The method of claim 1, wherein the compound or its pharmaceutically acceptable salt has formula:

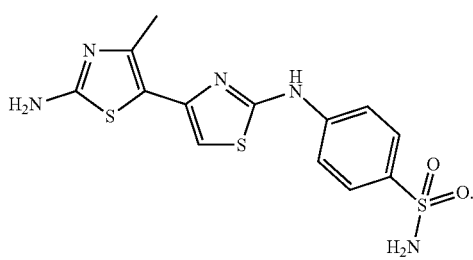 [SMILES: Cc1nc(N)sc1-c1csc(Nc2ccc(S(N)(=O)=O)cc2)n1]

8. The method of claim 1, wherein the therapeutically effective amount of a compound or its pharmaceutically acceptable salt is employed as an anti-cancer agent wherein cancer is selected from the group comprising lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; myelofibrosis, kidney cancer; cancer of the head and neck; cancer of the stomach; multiple myeloma; testicular cancer; germ cell tumor; neuroendocrine tumor; cervical cancer; oral cancer, carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma and/or a leiomysarcoma.

9. The method of claim 1, wherein the therapeutically effective amount of the compound or its pharmaceutically acceptable salt is administered to reduce cardiotoxicity side effects of chemotherapy and/or immunotherapy.

10. The method of claim 1, wherein the therapeutically effective amount of the compound or its pharmaceutically acceptable salt is administered as a single agent or in combination with chemotherapy, immunotherapy and/or radiotherapy in both adjuvant and neo-adjuvant settings.

11. The method of claim 1, wherein the therapeutically effective amount of the compound or its pharmaceutically acceptable salt is administered to induce metastasis inhibition.

12. The method of claim 1, wherein the therapeutically effective amount of the compound or its pharmaceutically acceptable salt is administered with a second therapeutic agent selected from an anti-cancer agent, an anti-inflammatory agent, an anti-hypertensive agent, an anti-fibrotic agent, an anti-angiogenic agent, and/or an immunosuppressive agent.

13. A compound for inhibiting lysyl oxidases having formula:

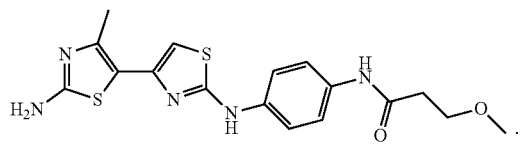 [SMILES: COCCC(=O)Nc1ccc(Nc2nc(-c3sc(N)nc3C)cs2)cc1]

14. The compound of claim 13 or its pharmaceutically acceptable salt administered in a therapeutically effective amount to treat a neurodegenerative disease, an angiogenesis-related disease, Alzheimer's disease, fibrosis including: liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis, diabetes, cerebral hemorrhage with amyloidosis, cardiac hypertrophy, Hutchinson-Gilford Progeria Syndrome, retinopathy, chemoresistance, and/or a kidney disorder including: kidney fibrosis, renal fibrosis, acute kidney injury, chronic kidney disease, diabetic nephropathy, glomerulosclerosis, hypertrophic scarring, keloids, diabetic skin, vesicoureteral reflux, tubulointerstitial renal fibrosis and/or glomerulonephritis.

15. The compound of claim 13 or its pharmaceutically acceptable salt administered as a single agent or in combination with chemotherapy, immunotherapy and/or radiotherapy in both adjuvant and neo-adjuvant settings.

16. The compound of claim 13 or its pharmaceutically acceptable salt administered with a second therapeutic agent selected from an anti-cancer agent, an anti-inflammatory agent, an anti-hypertensive agent, an anti-fibrotic agent, an anti-angiogenic agent, and/or an immunosuppressive agent.

17. A compound for inhibiting lysyl oxidases having formula:

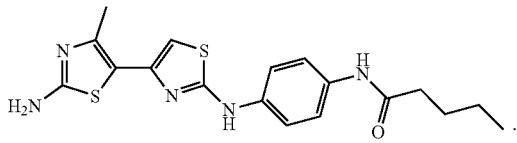 [SMILES: CCCCC(=O)Nc1ccc(Nc2nc(-c3sc(N)nc3C)cs2)cc1]

18. The compound of claim 17 or its pharmaceutically acceptable salt administered in a therapeutically effective amount to treat a neurodegenerative disease, an angiogenesis-related disease, Alzheimer's disease, fibrosis including: liver fibrosis, pulmonary fibrosis, renal fibrosis, myocardial fibrosis, cystic fibrosis, idiopathic pulmonary fibrosis, radiation-induced fibrosis, ocular fibrosis, Peylony's disease and scleroderma, or respiratory disorders, abnormal wound healing and repair, postoperative surgery, cardiac arrest-related fibrosis, excess or abnormal deposition of fibrotic material, all associated with disorders such as Crohn's disease and inflammatory bowel disease, liver, kidney and pancreas fibrosis, diabetes, cerebral hemorrhage with amyloidosis, cardiac hypertrophy, Hutchinson-Gilford Progeria Syndrome, retinopathy, chemoresistance, and/or a kidney disorder including: kidney fibrosis, renal fibrosis, acute kidney injury, chronic kidney disease, diabetic nephropathy, glomerulosclerosis, vesicoureteral reflux, tubulointerstitial renal fibrosis and/or glomerulonephritis.

19. The compound of claim 17 or its pharmaceutically acceptable salt administered as a single agent or in combination with chemotherapy, immunotherapy and/or radiotherapy in both adjuvant and neo-adjuvant settings.

20. The compound of claim 17 or its pharmaceutically acceptable salt administered with a second therapeutic agent selected from an anti-cancer agent, an anti-inflammatory agent, an anti-hypertensive agent, an anti-fibrotic agent, an anti-angiogenic agent, and/or an immunosuppressive agent.

* * * * *